US009085616B2

(12) United States Patent
Aderem et al.

(10) Patent No.: US 9,085,616 B2
(45) Date of Patent: *Jul. 21, 2015

(54) TOLL-LIKE RECEPTOR 5 LIGANDS AND METHODS OF USE

(75) Inventors: Alan Aderem, Seattle, WA (US); Fumitaka Hayashi, North Quincy, MA (US); Kelly D. Smith, Seattle, WA (US); David M. Underhill, Seattle, WA (US); Adrian Ozinsky, Seattle, WA (US)

(73) Assignees: THE UNIVERSITY FOR SYSTEMS BIOLOGY, Seattle, WA (US); UNIVERSITY OF WASHINGTON, Seattle, WA (US)

( * ) Notice: Subject to any disclaimer, the term of this patent is extended or adjusted under 35 U.S.C. 154(b) by 715 days.

This patent is subject to a terminal disclaimer.

(21) Appl. No.: 13/191,093

(22) Filed: Jul. 26, 2011

(65) Prior Publication Data
US 2012/0269855 A1 Oct. 25, 2012

Related U.S. Application Data

(63) Continuation of application No. 12/546,593, filed on Aug. 24, 2009, now abandoned, which is a continuation of application No. 10/125,692, filed on Apr. 17, 2002, now Pat. No. 7,915,381.

(60) Provisional application No. 60/285,477, filed on Apr. 20, 2001.

(51) Int. Cl.
| *A61K 39/39* | (2006.01) |
| *C07K 14/21* | (2006.01) |
| *C07K 14/195* | (2006.01) |
| *C07K 14/24* | (2006.01) |
| *C07K 14/255* | (2006.01) |
| *A61P 31/04* | (2006.01) |
| *C07K 14/25* | (2006.01) |
| *C07K 14/20* | (2006.01) |
| *C07K 14/32* | (2006.01) |
| *C07K 14/33* | (2006.01) |
| *A61K 39/02* | (2006.01) |
| *A61P 37/04* | (2006.01) |
| *C07K 14/28* | (2006.01) |
| *C07K 14/245* | (2006.01) |
| *A61K 39/00* | (2006.01) |

(52) U.S. Cl.
CPC ............ *C07K 14/195* (2013.01); *C07K 14/255* (2013.01); *A61K 39/00* (2013.01); *A61K 2039/55516* (2013.01); *C07K 2319/00* (2013.01)

(58) Field of Classification Search
CPC ............... C07K 14/195; C07K 14/255; C07K 2319/00; A61K 2039/55516; A61K 39/00
See application file for complete search history.

(56) References Cited

U.S. PATENT DOCUMENTS

| 5,194,254 | A | 3/1993 | Barber et al. |
| 5,420,109 | A | 5/1995 | Suto et al. |
| 5,612,035 | A | 3/1997 | Howell |
| 5,614,192 | A | 3/1997 | Vandenbark |
| 5,618,533 | A | 4/1997 | Flavell et al. |
| 5,677,427 | A | 10/1997 | Goldenberg et al. |
| 5,817,308 | A | 10/1998 | Scott et al. |
| 5,837,825 | A | 11/1998 | Meinersmann et al. |
| 6,030,624 | A | 2/2000 | Russell et al. |
| 6,130,082 | A | 10/2000 | Majarian et al. |
| 6,548,295 | B2 | 4/2003 | Andre et al. |
| 6,610,298 | B2 | 8/2003 | Hasan et al. |
| 6,610,661 | B1 | 8/2003 | Carson et al. |
| 6,685,935 | B1 | 2/2004 | Pawelek et al. |
| 6,703,487 | B2 | 3/2004 | Bird et al. |
| 6,740,487 | B1 | 5/2004 | Schwartz et al. |
| 6,753,166 | B2 | 6/2004 | Sims et al. |
| 6,797,813 | B2 | 9/2004 | De Waal Malefyt et al. |
| 2003/0232055 | A1 | 12/2003 | Medzhitov |

FOREIGN PATENT DOCUMENTS

| WO | WO-02/09748 | 2/2002 |
| WO | WO-02/085933 | 10/2002 |

OTHER PUBLICATIONS

Adachi et al., Immunity (1998) 9:143-150.
Aderem and Ulevitch, Nature (2000) 406:782-787.
Ahlers et al., J. Immunol. (1997) 158:3947-58.
Blackburn et al., Nature Structural Biology (2000) 7:847-849.
Bowie et al., Science (1990) 257:1306-1310.
Brem et al., J. Neurosurg. (1991) 74:441-446.
Brightbill and Modlin, Immunology (2000) 101:1-10.
Brightbill et al., Science (1999) 285:732-736.
Brostoff et al., Immunol. Ser. (1993) 59:203-218.
Cario and Podolsky, Infect. Immun. (2000) 68:7010-7017.
Chaudhary et al., Blood (1998) 91:4020-4027.
Ciacci-Woolwine et al., Infect. Immun. (1998) 66:1127-1134.
Ciacci-Woolwine et al., Infect. Immun. (1999) 67:5176-5185.
Collins et al., PNAS (1995) 92:8036-8040.
Cookson et al., The American Association of Immunologists (1997) 158:4310-4319.
Das Gracas Luna et al., Res. Microbiol. (2000) 151:575-582.
De Vries et al., Appl Environ Microbiol (1998) 64(12):5033-5038.

(Continued)

*Primary Examiner* — Robert A Zeman
(74) *Attorney, Agent, or Firm* — Morrison & Foerster LLP

(57) ABSTRACT

The invention provides methods to elicit an immune response with an immunomodulatory flagellin polypeptide having toll-like receptor 5 (TLR5) binding, and further comprising an ADCC targeting molecule.

8 Claims, 18 Drawing Sheets

(56) References Cited

OTHER PUBLICATIONS

Dorland's Medical Dictionary, definition of immunomodulator and immunomodulation, retrieved online at <http://www.mercksource.com> on Jun. 27, 2007.
Eaves-Pyles et al., J of Immunol (2001) 167:7009-7016.
Eaves-Pyles et al., The Journal of Immunology (2001) 166:1248-1260.
Eroshkin et al., Comput Appl Biosci (1993) 9:491-497.
Feghali and Wright, Frontiers in Bioscience (1997) 2:D12-D26.
Felix et al., Plant Journal (1999) 18(3):265-276.
Fujita and Yamaguchi, J. Gen. Microbiol. (1973) 76:127-134.
Gewirtz et al., The Journal of Clinical Investigation (2001) 107:99-109.
Goodlett et al., Anal Chem (2000) 72:1112-1118.
Gomez-Gomez and Boller, Mol. Cell (2000) 5:1003-11.
Hayashi, Nature (2001) 410(6832):1099-1103.
Herlyn and Birebent, Ann Med (1999) 31:66-78.
Ibrahim et al., J. Clin. Microbiol. (1985) 22:1040-1044.
Joys and Schodel, Infect. Immun. (1991) 59:3330-3332.
Joys and Street, Infect. Immun. (1993) 61:1146-1148.
Joys, Journal of Biological Chemistry (1985) 260(29) 15758-15761.
Kopp et al., Current Opinion in Immunology (1999) 11:13-18.
Kuwajima et al., Bacteriol. (1988) 170:3305-3309.
Kuwajima et al., PNAS USA (1989) 86:4953-4957.
Lazar et al., Molecular and Cellular Biology (1988) 8(3):1247-1252.
Logan et al., J. Bacteriology (1989) 171:3031-3038.
Major, J Receptor and Signal Transduction Res (1995) 15:595-607.
McDermott et al., Infect. Immun. (2000) 68:5525-9.
McEwen et al., Vaccine (1992) 10:405-411.
McSorley et al., J. Immunol. (2000) 164:986-993.
Means et al., Cytokine Growth Factor Rev. (2000) 11:219-232.
Medzhitov et al., Nature (1997) 388:394-397.
Medzhitov et al., Mol. Cell (1998) 2:253-268.
Mellentin-Micelotti et al., Anal Biochem (1999) 272:P182-190.
Mimori-Kiyosue et al., J. Mol. Biol. (1997) 270:222-237.
Muzio et al., J. Immunol. (2000) 164:5998-6004.
Namba et al., Nature (1989) 342:648-654.
Newton et al., Vaccines (1990) 90:439-445.
Newton et al., Science (1989) 244:70-72.
Ozinsky et al., PNAS USA (2000) 97:13766-13771.
Peel et al., J. Gen. Microbiol. (1988) 134:2171-2178.
Roberts and Vellacio, The Peptides: Analysis, Synthesis, Biology, Eds., Gross and Meinhofer (1983) 5:341, New York, NY, Academic Press, Inc.
Rock et al., PNAS USA (1998) 95:588-593.
Samakovlis et al., Biochem. Biophys. Res. Commun. (1992) 188:1169-1175.
Samatey et al., J. Struct. Biol. (2000) 132:106-111.
Samatey et al., Nature (2001) 410:331-337.
Scanga and Legros, Drugs (2000) 59(6):1217-1221.
Sebastiani et al., Genomics (2000) 64:230-240.
Sequence alignment for SEQ ID No. 8, 44-50.
Smith et al., Nature Immunol (2003) 4(12):1247-1253.
Steidler et al., Infect Immun (1998) 66:3183-3189.
Steiner et al., J. Clin. Invest. (2000) 105:1769-77.
Stocker and Newton, Int. Rev. Immunol. (1994) 11:167-178.
Sutton and Lee, Aliment Pharmacol (2000) 14:1107-1118.
Sztein et al., Journal of Infectious Diseases (1994) 170(6):1508-1517.
Underhill et al., Nature (1999) 401:811-815.
Uniprot/Swissprot Database, Accession No. FLIC_SALRU, 2 pages.
Urban et al., Cell (1988) 54:577-592.
Van Asten et al., Journal of Bacteriology (1995) 177(6):1610-1613.
Von Herrath and Whitton, Ann Med (2000) 32:285-292.
Wei et al., Nucleic Acids Research (1986) 14:8227.
Wilson and Czarnick, Eds., Combinatorial Chemistry (1997) 11:235, New York, NY, John Wiley & Sons.
Wolff, Ed., Burger's Medicinal Chemistry and Drug Discovery (1995) 15:619-620, New York, NY, John Wiley & Sons.
Wyant et al., Infect. Immun. (1999) 67:3619-24.
Wyant et al., Infect. Immun. (1999) 67:1338-46.
Xu et al., The American Association of Immunologists (1998) 160:1285-1289.
Youngkin, Nat Med (2001) 7(1):18-19.
Zhang et al., Anal Biochem (1999) 268:134-142.
Zuck et al., PNAS USA (1999) 96:11122-11127.

MKVNTNIISLKTQEYLRKNNEGMTQAQERLASGKRINSSLDD
AAGLAVVTRMNVKSTGLDAASKNSSMGIDLLQTADSALSSMS
SILQRMRQLABQSSNGSFSDEDRKQYTAEFGSLIKELDHVAD
TTNYNNIKLLDQTATGAATQVSIQASDKANDLINIDLFNAKG
LSAGTITLGSGSTVAGYSALSVADADSSQEATEAIDELINNI
SNGRALLGAGMSRLSYNVSNVNNQSIATKASASSIEDADMAA
EMSEMTKYKILTQTSISMLSQANQTPQMLTQLINS

| | | |
|---|---|---|
| C.jejuni | 1 | MGFRINTNVAALNAKANADINSKSLDASLSRLSSGLRINSAADDASGMAIADTLRSQANT |
| H.pylori | 1 | MAFQVNTNINAMNAHVQSALTQNALKTSLERLSSGLRINKAADDASGMTVADSLRSQASS |
| V.cholerae | 1 | MTINVNTNVSAMTAQRYLTKATGELNTSMERLSSGNRINSAKDDAAGLQISNRLTAQSRG |
| P.aeruginosa | 1 | MALTVNTNIASLNTQRMLNNSSASLNTSLQRLSTGSRINSAKDDAAGLQIANRLTSQVNG |
| R.sphaeroides | 1 | -MTTINTNIGAIAAQANMTKVNDQFNTAMTRLSTGLRINAAKDDAAGMAIGEKMTAQVMG |
| P.mirabilis1 | 1 | MAQVINTNYLSLVTQNNMLNKSQGTLGSAIERLSSGLRINSAKDDAAGQAIANRFTSNVNG |
| P.mirabilis2 | 1 | MAQVINTNYLSLVTQNMLNRSQSALGNAIERLSSGMRINSAKDDAAGQAIANRFTSNING |
| S.typhimurium2 | 1 | MAQVINTNSLSLLTQNNMLNKSQSALGTAIERLSSGLRINSAKDDAAGQAIANRFTANIKG |
| S.typhimurium1 | 1 | MAQVINTNSLSLLTQNNMLNKSQSALGTAIERLSSGLRINSAKDDAAGQAIANRFTANIKG |
| S.marcesens | 1 | MAQVINTNSLSLLTQNNMLNKSQSSLGTAIERLSSGLRINSAKDDAAGQAISNRFTANIKG |
| E.coli | 1 | MAQVINTNSLSLLITQNNINKNQSALSSSIERLSSGLRINSAKDDAAGQAIANRFTSNIKG |
| S.flexneri | 1 | MAQVINTNSLSLITQNNINKNQSALSSSIERLSSGLRINSAKDDAAGQAIANRFTSNIKG |
| T.pallidumA | 1 | --MIINHNMSAMFAQRTLGHTNVQVGKGIEKLSSGYRINRAGDDASGLAVSEKMRSQIRG |
| T.pallidumB | 1 | --MIINHNMSAMFAQRTLGNTNLSVQKNMEKLSSGLRINRAGDDASGLAVSEKMRSQIRG |
| L.pneumophila | 1 | --MIINHNLSAVNAHRSLKFNELAVDKTMKALSSGMRINSAADDASGLAVSEKLRTQVNG |
| B.burgdorferei | 1 | --MIINHNTSAINASRNNGINAANLSKTQEKLSSGYRINRASDDAAGMGVSGKINAQIRG |
| B.subtilus | 1 | --MRINHNIAALNTLNRLSSNNSASQKNMEKLSSGLRINRAGDDAAGLAISEKMRGQIRG |
| C.difficile | 1 | --MRVNTNVSALIANNQMGRNVSGQSKSMEKLSSGLRIKRAADDAAGLAISEKMRAQLKG |
| R.meliloti | 1 | -MTSILTNNSAMAALSTLRSISSSMEDTQSRISSGLRVGSASDNAAYWSIATTMRSDNQA |
| A.tumefaciens | 1 | -MASILTNNNAMAALSTLRSIASDLSTTQDRISSGLKVGSASDNAAYWSIATTMRSDNKA |
| R.lupini | 1 | -MASVLTNINAMSALQTLRSISSNMEDTQSRISSGMRVGSASDNAAYWSIATTMRSDNAS |
| L.monocytogenes | 1 | --MKVNTNIISLKTQEYLRKNNEGMTQAQERLASGKRINSSLDDAAGLAVVTRMNVKSTG |
| B.clarridgeiae | 1 | MGTSLLTNKSAMTALQTLRSIDANLDRSKDRVSTGLRISNASENTAYWSISSMMRHDSNT |
| consensus | 1 | m   intNv  al aq nl k q  l  slerlssGlrinsa ddaagmaia rl sqvrg |

FIG. 7AA

```
C.jejuni         61  LGQAISNGNDAIGILQTADKAMDEQLKILDTIKTKATQAAQD--GQSLKTRTMLQADINR
H.pylori         61  LGQAIANTNDGMGIIQVADKAMDEQLKILDTVKVKATQAAQD--GQTTESRKAIQSDIVR
V.cholerae       61  LDVAMRNANDGISIAQTAEGAMNESTSILQRMRDLALQSANG--TNSASERQALNEESVA
P.aeruginosa     61  LNVATKNANDGISLAQTAEGALQQSTNILQRMRDLSLQSANG--SNSDSERTALNGEAKQ
R.sphaeroides    60  LNQAIRNAQDGKNLVDTTEGAHVEVSSMLQRLRELAVQSSND--TNTAADRGSLAAEGKQ
P.mirabilis1     61  LTQASRNANDGISIAQTTEGALNEINNNLQRIRELTVQAKNG--TNSNSDITSIQNEVKN
P.mirabilis2     61  LTQASRNANDGISVSQTTEGALNEINNNLQRIRELTVQAKNG--TNSNSDINSIQNEVNQ
S.typhimurium2   61  LTQASRNANDGISIAQTTEGALNEINNNLQRVRELAVQSANS--TNSQSDLDSIQAEITQ
S.typhimurium1   61  LTQASRNANDGISIAQTTEGALNEINNNLQRVRELAVQSANS--TNSQSDLDSIQAEITQ
S.marcesens      61  LTQASRNANDGISLAQTTEGALNEVNDNLQNIRRLTVQAQNG--SNSTSDLKSIQDEITQ
E.coli           61  LTQAARNANDGISVAQTTEGALSEINNNLQRIRELTVQATTG--TNSDSDLDSIQDEIKS
S.flexneri       61  LTQAARNANDGISVAQTTEGALSEINNNLQRIRELTVQASTG--TNSDSDLDSIQDEIKS
T.pallidumA      59  LNQASTNASNGVNFIQVTEAYLQETTDIMQRIRELAIQAANG--IYSAEDRMQIQVEVSQ
T.pallidumB      59  LNQASTNAQNGISFIQVAESYLQETTDVIQRIRELSVQSANG--IYSAEDRMYIQVEVSQ
L.pneumophila    59  LRQAERNTEDGMSFIQTAEGFLEQTSNIIQRIRVLAIQTSNG--IYSNEDRQLVQVEVSA
B.burgdorferei   59  LSQASRNTSKAINFIQTTEGNLNEVEKVLVRMKELAVQSGNG--TYSDADRGSIQIEIEQ
B.subtilus       59  LEMASKNSQDGISLIQTAEGALTETHAILQRVRELVVQAGNTGTQDKATDLQSIQDEISA
C.difficile      59  LDQAGRNVQDGISVVQTAEGALEETGNILTRMRTLAVQASNET--NSKDERAKIAGEMEQ
R.meliloti       60  LSAVQDALGLGAAKVDTAYSGMESAIEVVKEIKAKLVAATED----GVDKAKIQEEITQ
A.tumefaciens    60  LGAVSDALGMGAAKVDTASAGMDAAIKVVTDIKAKVVAAKEQ----GVDKTKVQEEVSQ
R.lupini         60  LSAVQDAIGLGAAKVDTASAGMDAVIDVVKQIKNKLVTAQES----SADKTKIQGEVKQ
L.monocytogenes  59  LDAASKNSSMGIDLLQTADSALSSMSSILQRMRQLAVQSSNG--SFSDEDRKQYTAEFGS
B.clarridgeiae   61  MSAIVDAINLGKEQVGIADTAIGLTKEALDDIQKSMVSAREK---GSDDIAKIQDSIIG
consensus        61  l qatrnandgisilqtaegal e    ilqrirdl vga ng  tqs  dr iq ei q
```

FIG. 7AB

```
C.jejuni          119 LMEELDNIANTTSFNGKQLLSGNFINQEFQIGASSN-QTVKATIGATQSSKIGLTRFETG
H.pylori          119 LIQGLDNIGNTTYNGQALLSGQFTNKEFQVGAYSN-QSIKASIGSTTSDKIGQVRIATG
V.cholerae        119 LQDELNRIAETTSFGGRKLLNGSFGEASFQIGSSSG-EAIMGLTSVRADDFR-------
P.aeruginosa      119 LQKELDRISNTTFGGRKLLDGSFGVASFQVGSAAN-EIISVGIDEMSAESLNGTYFKAD
R.sphaeroides     118 LIAEINRVAESTTFNGMKVLDGSFTGKQLQIGADSG-QTMAINVDSAAATDIGA-----
P.mirabilis1      119 VLDEINRISEQTQFNGVKVLSGEKSEMVIQVGTNDN-ETIKFNLDKVDNDTLGVASDKLF
P.mirabilis2      119 RLDEINRVSEQTQFNGVKVLSGEKSKMTIQVGTNDN-EVIEFNLDKIDNDTLGVASDKLF
S.typhimurium2    119 RLNEIDRVSGQTQFNGVKVLA-QDNTLTIQVGANDG-ETIDIDLKQINSQTLGLDSLNVQ
S.typhimurium1    119 RLNEIDRVNGQTQFSGVKVLA-QDNTLTIQVGANDG-ETIDIDLKQINSQTLGLDTLNVQ
S.marcesens       119 RLSEINRISEQTDFNGVKVLS-SDQKLTIQVGANDG-ETTDIDLKKIDAKQLGMDTFDVT
E.coli            119 RLDEIDRVSGQTQFNGVNVLS-KDGSMKIQVGANDG-ETITIDLKKIDSDTLNLAGFNVN
S.flexneri        119 RLDEIDRVSGQTQFNGVNVLA-KDGSMKIQVGANDG-QTITIDLKKIDSDTLGLNGFNVN
T.pallidumA       117 LVAEVDRIASSAQFNGMNLLTGRFSRTEG---------------ENVIGGSMWFH
T.pallidumB       117 LVAEIDRIASHAQFNGMNMLTGRFARETG---------------ENTVTASMWFH
L.pneumophila     117 LVDEVDRIASQAEFNKFKLFEGQFARGS----------------R---VASMWFH
B.burgdorferei    117 LTDEINRIADQAQYNQMHMLSNKSASQNVRTAEELGMQPAKINTPASLSGSQASWTLRVH
B.subtilus        119 LTDEIDGISNRTEFNGKKLLDGTYKVDTATP-----------------ANQKNLVFQ
C.difficile       117 LRSEVDRIADSTKFNGENLLS-SDKKIALQVG-------------------AEAVSNNVIEVS
R.meliloti        115 LKDQLTSIAEAASFSGENWLQADLSGGPVTKSVVGGFVRDSSGAVSVKKVDYSLNTDTVL
L.lupini          115 LLDQLKSIGTSASFNGENWLVSSAN---ATKTVVSGFVRDAGGTVSVKTTDYALDANSML
A.tumefaciens     115 LQEQLKGIVDSASFSGENWLKGDLS-TTTTKSVVGSFVRE-GGTVSVKTIDYALNASKVL
L.monocytogenes   117 LIKELDHVADTTNYNNIKLLDQTATGAATQVS-----------IQASDKANDLINID
B.clarridgeiae    117 NMKNISNAVQSASFGGKNILSNGGQTVGMAAGYRREGTAVVDMDVGGSELNFGTIGSD
consensus         121 lmeeidria  t fngmkll g         qig          v  i v   igl   l

FIG. 7BA
```

| | | |
|---|---|---|
| C.jejuni | 178 | GRISTSGEVQFTLKNYNGIDDFQFQKVVISTSVGTGLGALADEINKNADKTG----VRAT |
| H.pylori | 178 | ALITASGDISLTFKQVDGVNDVTLESVKVSSSAGTGIVLAEVINKNSNRTG----VKAY |
| V.cholerae | 171 | MGGQSFIAEQPKTKEWGVP------ |
| P.aeruginosa | 178 | GGGAVTAATASGTVDIAIG------ |
| R.sphaeroides | | ------ |
| P.mirabilis1 | 178 | DTKTEKKGVTAAG------ |
| P.mirabilis2 | 178 | DAKTEKKGVTAAG------ |
| S.typhimurium2 | 177 | KAYDVKDTAVTTKAYANNGTTLDVSGLDDAAIKAATGGTNGTASVT------GGAVKFD |
| S.typhimurium1 | 177 | QKYKVSDTAATVTGYADTTIALDNS----TFKASATGLGGTDEKI------DGDLKFD |
| S.marcesens | 177 | TKSAKAGAEIATG------ |
| E.coli | 177 | GEGETANTAATLKDMVGLKLDNTGVTTAGVNRYIADKAVASSTDILNAVAGVDGSKVSTE |
| S.flexneri | 177 | GGGAVANTAASKADLVAANATVVGNKYTVSAGYDAAKASDLLAGVS----D---GDTVQAT |
| T.palliduma | 157 | IGANMDQRMR------VY------ |
| T.pallidumB | 157 | IGANMDQRTR------AY------ |
| L.pneumophila | 153 | MGPNQNQRER------FY------ |
| B.burgdorferei | 177 | VGANQDEAIA------VN------ |
| B.subtilus | 159 | IGANATQQIS------VN------ |
| C.difficile | 160 | LINTKGVLTT------RN------ |
| R.meliloti | 175 | FDTTGN----TGILDKVYN------ |
| A.tumefaciens | 172 | YTEG------ |
| R.lupini | 173 | VDTRATGKTGILDTAYTG------ |
| L.monocytogenes | 163 | LFNAKGLSAG------ |
| B.clarridgeiae | 177 | GTIDMSQGVLGGIFGTSKG------ |
| consensus | 181 | |

*FIG. 7BB*

| | | |
|---|---:|---|
| C.jejuni | 234 | FTVETRGIAAVRAGATSDTFAINGVKIGKVDYKDGDANGALVAAINSVKDTTGVEASIDA |
| H.pylori | 234 | ASVITTSDVAVQSGSLSNLTLNGIHLGNIADIKKNDSGRLVAAINAVTSETGVEAYTDQ |
| V.cholerae | 190 | ----------------------------------------------PTARDLKFEFTKK |
| P.aeruginosa | 197 | ----------------------------------------------ITGGSAVNVKVDM |
| R.sphaeroides | | |
| P.mirabilis1 | 191 | ----------------------------------------AG----------VTDAKKINA |
| P.mirabilis2 | 191 | ----------------------------------------DA----------IDANALGIS |
| S.typhimurium2 | 230 | ADNNKYFVTIGGFTGADAAKNG--DYEVNVATDGTVTLAAGATKTTMPAGATTKTEVQEL |
| S.typhimurium1 | 225 | DTTGKYYAKVTVTG--GTGKDG--YYEVSVDKTNGEVTLAAVTPATVTTATALSGKMYSA |
| S.marcesens | 190 | ----------------------------------T-----------KITVDS--DA |
| E.coli | 237 | ADVGFGAAAPGTPVEYTYHKDTNTYTASASVDATQLAAFLNPEAGGTTAATVSIGNGTTA |
| S.flexneri | 231 | INNGFGTAASATNYKYDSASKS-YSFDTTTASAADVQKYLTPGVGDTAKGTITIDG---S |
| T.palliduma | 169 | ----------------------------------------------IGTMTAVA |
| T.pallidumB | 169 | ----------------------------------------------IGTMTAAA |
| L.pneumophila | 165 | ----------------------------------------------IGTMTSKA |
| B.burgdorferei | 189 | ----------------------------------------------IYAANVAN |
| B.subtilus | 171 | ----------------------------------------------IEDMGADA |
| C.difficile | 172 | ----------------------------------------------VNSANIDA |
| R.meliloti | 190 | ------------------------------------------VSQASVTLPVNV |
| A.tumefaciens | 176 | -----------------------------------------------------T- |
| R.lupini | 192 | --------------------------------------------LNANTVTVDINK |
| L.monocytogenes | 173 | |
| B.clarridgeiae | 196 | ----------------------------------------DEGEDVVGKGIGA |
| consensus | 241 | |

*FIG. 7CA*

```
C.jejuni          294  NGQLLLTSREGRGIKIDGNIGGAFINADMKENYGRLSLVKNDGKDILISGSNLSSAGFG
H.pylori          294  KGRLNLRSIDGRGIEIK---------TDSVSNGPSALTMVNGGQDLTKGSTNYGRLSLT
V.cholerae        203  DG------EAVVLDIIAKDGD------------------DIEELA---------TYINGQTD
P.aeruginosa      210  KGNETAEQAAAKIAAAVND-------------------ANVGIG---------AFSDGDTI
R.sphaeroides     
P.mirabilis1      202  AATLDMMVSLVKEFNLDG------------------------KPVTDK-------FIVTKGGKD
P.mirabilis2      202  GSKKYVTGISVKEYKVDG------------------------KVSSDK-------VVLNDGSDD
S.typhimurium2    288  KDTPAVVSADAKNALIAGGV--------DATDANGAELVKMSYTDKNGKTIEGGYALKAGDK
S.typhimurium1    281  NPDSDIAKAALTAAGVTG----------TASVVKMSYTDNNGKTIDGGLAVKVGDD
S.marcesens       199  T-----KQADADVTGLAKG-----------------------QTLVSG------TDADGKSA
E.coli            297  QEQKVIIAKDGSLTAADDG--------AALYLDDTGNLSKTN-AGTDTQAKLS
S.flexneri        287  -AQDVQISSDGKITASNG---------DKLYIDTTGRLTKNGSGASLTEASLS
T.pallidumA       177  LG
T.pallidumB       177  LG
L.pneumophila     173  LK
B.burgdorferei    197  LFSGEGAQAAQTAPVQEGA
B.subtilus        179  LGIKEADG
C.difficile       180  MS
R.meliloti        202  NGTTSEYTVGAYNVDDLID--------ASATFDGDYANVGAGALAGDYVKVQG
A.tumefaciens     177
R.lupini          204  GGVITQASVRAYSTDEMLS--------LGAKVDGANSNVAVGGGSAFVKVDGS
L.monocytogenes   173
B.clarridgeiae    209  FSAAHATYKGLEDTLRN----------AEADLAKAIAKYGESPEDEPGKAI
consensus         301
```

FIG. 7CB

```
C.jejuni         354 ATQFISQASVSLRESKGQIDANIADAMGFGSANKGVVLGGYSSVSAYMSSAGSGFSSGSG
H.pylori         344 RLDAKSINVVSAS-----DS---------------Q-----HLGFTAIGFGESQV
V.cholerae       232 LFKASVDQEGKLQ-----------------------------IFVAEPNIEGNFN
P.aeruginosa     243 SYVSKAGKDGSGA-----------------------------ITSAVSGVVIADT
R.sphaeroides
P.mirabilis1     235 YVATKSDFELDAT-----------------------------GTK--LGLKASAT
P.mirabilis2     235 YIVSKSDFTLKSG-----------------------------TTTGEVEFTGSKT
S.typhimurium2   342 YYAADYDEATGAI-----------------------------KAKTTSYTAADGT
S.typhimurium1   327 YYSATQDKDG-SI-----------------------------SIDTTKYTADNGT
S.marcesens      227 YFIATKDDATGDV-----------------------------AYTKAKVADDGKV
E.coli           341 DLMANNANAKTVI-----------------------------TT-DKGTFTANTT
S.flexneri       330 TLAANNTKATTID-----------------------------IGGTSISFTGNST
T.pallidumA      179 ------------------------------------------VRNGVDESIMSIE
T.pallidumB      179 ------------------------------------------VRDVGDESILNID
L.pneumophila    175 ------------------------------------------LVKADGR-PIAIS
B.burgdorferei   216 QQEGAQQPAPVTA-----------------------------PSQGGVNSPVNVT
B.subtilus       187 ---SIAALHSVND-----------------------------LDVTKFADNAADT
C.difficile      182 -------------------------------------------VS---GSI
R.meliloti       247 SWVKAVDVAATGQEVVYDD-----------------GTTKWGVDTTVTGAPATNVA
A.tumefaciens    177 --PGTIDANS--------------------------------GILNATGATTVG
R.lupini         249 WVKGSVDAAASITASTPVAGK--------FAAAYTAAEAGTAAAAGDAIIVDETNSGAGAV
L.monocytogenes  173 ------------------------------------------TITLGSGSTVAGYS
B.clarridgeiae   250 IEKAKQAVETAKTG----------------------------LKDGQEAYNKAKG
consensus        361                                                             m
```

FIG. 7DA

```
C.jejuni         414  YSVGSGKNYSTGFANAIAISAASQLSTVYNVSAGSGFSSGSTLSQFA-----T-----
H.pylori         374  AETTVNLRDVTGNFNANVKSASGANYNAVIASGNQSLGSG------------------
V.cholerae       258  ISGGLATELGLN----------------------------------------------
P.aeruginosa     269  GSTGVGTAAGVAPSA-------------------------------------------
R.sphaeroides         ----------------------------------------------------------
P.mirabilis1     259  TEFKVDAGKDVKTLN-------------------------------------------
P.mirabilis2     261  TKFTADAGKDVKVLN-------------------------------------------
S.typhimurium2   368  TKTAANQLGGVDGKTEVVTIDGKTYNAS------------------------------
S.typhimurium1   352  SKTALNKLGGADGKTEVVTIDGKTYNAS------------------------------
S.marcesens      253  TDSGTDAG--------------------------------------------------
E.coli           366  KFDGVDISVDASTFANAVKNETYTATVG---VTLPATYTVNNGTAASAYLVDGKVSKTP-
S.flexneri       356  TPDTITYSVTGAKVDQAAFDKAVSTSGNNVDFTTAGYSVNGTTGAVTKGVDSVYVDNNEA
T.pallidumA      192  --TADSAN--------------------------------------------------
T.pallidumB      192  --DPEKAN--------------------------------------------------
L.pneumophila    187  --SPGEAN--------------------------------------------------
B.burgdorferei   242  --TTVDAN--------------------------------------------------
B.subtilus       210  --ADIGFD--------------------------------------------------
C.difficile      187  --GTEAAS--------------------------------------------------
R.meliloti       286  APASIATIDITIAAQ-------------------------------------------
A.tumefaciens    198  AKTYTQISVLDMNVG-------------------------------------------
R.lupini         302  NLTQSVLTMDVSSMS-------------------------------------------
L.monocytogenes  187  ALSVADAD--------------------------------------------------
B.clarridgeiae   277  EFQTVLDGMTLADFTELKG---------------------------------------
consensus        421
```

*FIG. 7DB*

```
C.jejuni          462  ---------------------------------------MKTTAFGVKDETAGVTTLKGAMAVMDIAETATT
H.pylori          414  ------------------------------------------------VTTLRGAMVVIDIAESAMK
V.cholerae        270  ---------------------------------------GGPGVKTTVQDIDITSVGGSQNAVGIDAALK
P.aeruginosa      284  --------------------------------------TAFAKTNDTVAKIDISTAKALSRRAGDRTTAIK
R.sphaeroides     274  ---------------------------------------------------------VKDDALATLDKAIN
P.mirabilis1      276  ---------------------------------------------------------VKDDALATLDNAIS
P.mirabilis2      396  -----------------------------------KAAGHDFKAQPELAEAAAKTTENPLQKIDAALA
S.typhimurium2    380  -----------------------------------KAAGHDFKAEPELAEQAAKTTENPLQKIDAALA
S.typhimurium1    261  ---------------------------------------------------------VKNPLATLDKALA
S.marcesens       422  -----AEYFAQADGTITSGENAATSKAIYVSANGNLTNTTSESEATTNPLAALDDAIA
E.coli            416  --SGKAVYKDADGKLTTDAETKAATTADPLKALDEAIS
S.flexneri        198  ---------------------------------------------------------KSIGTIDAALK
T.pallidumA       198  ---------------------------------------------------------RAIGTLDEAIK
T.pallidumB       193  ---------------------------------------------------------DVIGLADAALT
L.pneumophila     248  ---------------------------------------------------------TSLAKIENAIR
B.burgdorferei    216  ---------------------------------------------------------AQLKVVDEAIN
B.subtilus        193  ---------------------------------------------------------KMIVNLDSSLA
C.difficile       301  ---------------------------------------------------------AGNLDALIAGVDEALT
R.meliloti        213  ---------------------------------------------------------TDDLDNALYSVETALT
A.tumefaciens     317  ---------------------------------------------------------STDVGSYLTGVEKALT
R.lupini          195  ---------------------------------------------------------SSQEATEAIDELIN
L.monocytogenes   296  ---------------------------------LGELHSDIQRMIMTSVQNTVRDAVN
B.clarridgeiae    481
consensus                                                                       m     id   am
```

*FIG. 7EA*

```
C.jejuni         495  NLDQIRADIGSVQNQVTSTINNITVTQVNVKAAESQIRDVDFAAAESANYSKANILAQSGS
H.pylori         433  MLDKVRSDLGSVQNQMISTVNNISITQVNVKAAESQIRDVDFAEESANFNKNNILAQSGS
V.cholerae       302  YVDSQRADLGAKQNRLSHSISNLSNIQENVEASKSRIKDTDFAKETTQLTKSQILQQAGT
P.aeruginosa     317  QIDASVPTSVAVQNRFDNTINNLKNIGENVSAARGRIEDTDFAAAETANLTKNQVLQQAGT
R.sphaeroides         ------------------------------------------------------------
P.mirabilis1     288  TIDESRSKLGAIQNRFESTINNLNNTVNNLSASRSRILDADYATEVSNMSRGQILQQAGT
P.mirabilis2     290  KVDESRSKLGAIQNRFQSTINNLNNTVNNLSASRSRILDADYATEVSNMSKNQILQQAGT
S.typhimurium2   429  QVDALRSDLGAVQNRFNSAITNLGNTVNNLSEARSRIEDSDYATEVSNMSRAQILQQAGT
S.typhimurium1   413  QVDTLRSDLGAVQNRFNSAITNLGNTVNNLSARSRIEDSDYATEVSNMSRAQILQQAGT
S.marcesens      274  QVDGLRSSLGAVQNRFDSVINNLNSTVNNLSASQSRIQDADYATEVSNMSRANILQQAGT
E.coli           476  SIDKFRSSLGAIQNRLDSAVTNLNNTTTNLSEAQSRIQDADYATEVSNMSKAQIIQQAGN
S.flexneri       472  SIDKFRSSLGAVQNRLDSAVTNLNNTTTNLSEAQSRIQDADYATEVSNMSKAQIIQQAGN
T.pallidumA      209  RINKQRADLGGYQNRMEYTVVGLDIAAENLQAAESRIRDANIAKQMVEYTKNQVLTQSGT
T.pallidumB      209  KINKQRADLGAYQNRLEYTVGVNVAAENLQAAESRIRDVDMAKEMVDYTKNQILVQSGT
L.pneumophila    204  KIMKQRADMGAYYNRLEYTAKGLMGAYENMQASESRIRDADMAEEVVSLTTKQILVQSGT
B.burgdorferei   259  MISDQRANLGAFQNRLESIKDSTEYAIENLKASYAQIKDATMTDEVVAATTNSILTQSAM
B.subtilus       227  QVSSQRAKLGAVQNRLEHTINNLSASGENLTAAESRIRDVDMAKEMSEFTKNNILSQASQ
C.difficile      204  DINSARALLGAQQNRLESTQNNLNNTVENVTAAESRIRDTDVASEMVNLSKMNILVQASQ
R.meliloti       317  DMTSAAASLGSISSRIDLQSDFVNKLSDSIDSGVGRLVDADMNEESTRLKALQTQQQLAI
A.tumefaciens    229  KMTSAGAKLGSLSARIDLQSGFADKLSDTIEKGVGRLVDADMNEESTKLKALQTQQQLAI
R.lupini         333  SLTSAGAELGSIKQRIDLQVDFASKLGDALAKGIGRLVDADMNEESTKLKALQTQQQLAI
L.monocytogenes  209  NISNGRALLGAGMSRLSYNVSNVNNQSIATKASASSIEDADMAAEMSEMTKYKILTQTSI
B.clarridgeiae   321  VTLTAGSKIGAAVNLVNIQLNFVKKLLDNVEVGIGALVDADMNAESAKLAALQVQQLGI consensus        541  1    ra  lgavqnrvd  i nl       enl  aa sri dad a evtnlsk qilqq gs
```

FIG. 7EB

```
C.jejuni         555  YAMAQANSVHQNVLRLLQ--
H.pylori         493  YAMSQANTVQQNILRLLT--
V.cholerae       362  SILAQAKQLPNSAISLLQ--
P.aeruginosa     377  AILAQANQLPQSVLSLLR--
R.sphaeroides         --------------------
P.mirabilis1     348  SVLAQANQVPQTVLSLLR--
P.mirabilis2     350  AVLAQANQVPQTVLSLLR--
S.typhimurium2   489  SVLAQANQVPQNVLSLLR--
S.typhimurium1   473  SVLAQANQVPQNVLSLLR--
S.marcesens      334  SVLAQANQSTQNVLSLLR--
E.coli           536  SVLAKANQVPQQVLSLQQG-
S.flexneri       532  SVLAKANQVPQQVLSLLQG-
T.pallidumA      269  AMLAQANTSAQSILSILR--
T.pallidumB      269  AMLAQANQATQSVLSLLR--
L.pneumophila    264  AMLARANMKPNSVLKLLQHI
B.burgdorferei   319  AMIAQANQVPQYVLSLLR--
B.subtilus       287  AMLAQANQQPQNVLQLLR--
C.difficile      264  SMLSQANQQPQGVLQLLG--
R.meliloti       377  QALSIANSDSQNVLSLFR--
A.tumefaciens    289  QALSIANSDSQNILSLFR--
R.lupini         393  QSLSIANSDSQNILSLFR--
L.monocytogenes  269  SMLSQANQTPQMLTQLINS-
B.clarridgeiae   381  QALSIANQGSQNILALFRN-
consensus        601   ilaqanq pqnvlsllr
```

TOLL-LIKE RECEPTOR 5 LIGANDS AND METHODS OF USE

CROSS-REFERENCE TO RELATED APPLICATIONS

This application is a continuation of U.S. Ser. No. 12/546,593 filed 24 Aug. 2009, which is a continuation of U.S. Ser. No. 10/125,692 filed 17 Apr. 2002 and now U.S. Pat. No. 7,915,381, which claims benefit under 35 U.S.C. §119(e) to provisional application 60/285,477 filed 20 Apr. 2001. The contents of these applications are incorporated herein by reference.

STATEMENT OF RIGHTS TO INVENTIONS MADE UNDER FEDERALLY SPONSORED RESEARCH

This invention was made with government support under grant numbers 5R37AI025032 and 5R01AI032972, awarded by the National Institutes of Health. The United States Government has certain rights in this invention.

BACKGROUND OF THE INVENTION

Cancer is the second leading cause of death in the United States, accounting for one in every four deaths. This year, it is expected that over 1500 Americans will die of cancer each day and that a million new cases of cancer will be diagnosed. The most common treatments for cancer are surgery, radiation and chemotherapy. According to the American Cancer Society, immunotherapy can be considered as the "fourth modality" in the treatment of cancer. Immunotherapy is treatment that stimulates one's own immune system to fight cancer.

Cancer is a group of diseases characterized by uncontrolled growth of abnormal cells of the body. All types of cancer involve the malfunction of genes that control cell growth and division. Some of these genes become incorrectly regulated, resulting in over- or under-production of a particular protein, while others become mutated, resulting in unusual or abnormal proteins that alter normal cellular functions. These abnormal proteins, referred to as "tumor cell antigens," should be recognized and destroyed by an individual's immune system as "foreign" antigens.

However, the immune system of a cancer patient may ignore these tumor antigens and be unresponsive to the growing tumor. Using immunotherapy approaches, such as cancer vaccines and immune system modulators, an individual's immune system can be induced to mount a potent immune response against tumor cell antigens, resulting in elimination of cancer cells. A cancer vaccine can contain a tumor cell antigen that stimulates the immune system to recognize and destroy cells which display that antigen. Treating an individual with such a cancer vaccine can result in a humoral response, which involves producing antibodies that recognize and target tumor cells for destruction and a cellular response, which involves producing cytotoxic T cells that recognize and destroy tumor cells directly, or both responses. It can be desirable to obtain both a humoral and cellular immunity response during immunotherapy because both arms of immune response have been positively correlated with beneficial clinical responses. To help stimulate either or both humoral and cellular immune responses, a cancer vaccine can be combined with an adjuvant, which is a substance that stimulates a general immune response.

The potency of cancer vaccines is greatly enhanced by the use of adjuvants. The selection of an adjuvant for use with a particular vaccine can have a beneficial effect on the clinical outcome of vaccination. Some vaccines are ineffective in the absence of an adjuvant. Effectiveness of a vaccine may be particularly troublesome when the vaccine is produced from self antigens such as those required for cancer vaccines or other non-infectious disease vaccines. In view of the beneficial effects of adjuvants in vaccine formulations, it is surprising that only one type of adjuvant, aluminum-salt based adjuvants, are currently in wide use in United States-licensed vaccines.

Thus, there exists a need for more and improved immunological adjuvants. The present invention satisfies this need and provides related advantages as well.

SUMMARY OF THE INVENTION

The invention provides an immunomodulatory flagellin peptide having at least about 10 amino acids of substantially the amino acid sequence GAVQNRFNSAIT, or a modification thereof, and having toll-like receptor 5 (TLR5) binding. Methods of inducing an immune response are also provided.

BRIEF DESCRIPTION OF THE DRAWINGS

FIGS. 7AA-F show a comparison of flagellin amino acid sequences from 22 species of bacteria (SEQ ID NOS:11-33) and a consensus sequence of amino acid residues conserved across species (SEQ ID NO:34).

DETAILED DESCRIPTION OF THE INVENTION

Figure 1A:
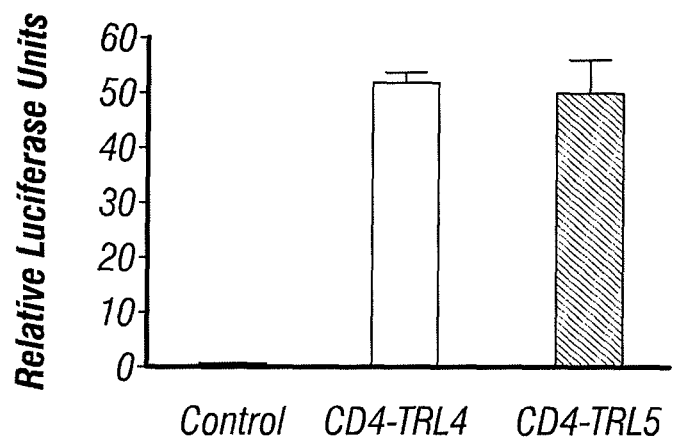
FIGS. 1A-B show NF-kB activation and TNFa production in cells expressing CD4-TLR4 or CD4-TLR5.

The invention is directed to flagellin derived peptides that exhibit immunomodulatory activity and to methods of inducing an immune response through activation of toll-like receptor 5 (TLR5). The identification of active flagellin peptides and their corresponding receptor, TLR5, expands the available treatment methods for inducing an immune response. Moreover, the identification of active flagellin peptides and their cognate receptor allows the identification of immunomodulatory compounds.

In one embodiment, the invention is directed to immunomodulatory flagellin peptides that bind to TLR5 and induce a TLR5-mediated activity. The peptides can be used, for example, to effectively stimulate an immune response or ameliorate a pathological condition by administration of immunomodulatory flagellin peptides and combinations of such peptides with antigens and other immunomodulatory molecules. Full length flagellin polypeptides are also used in the methods of the invention to stimulate an immune response. An advantage of the immunomodulatory flagellin peptides of the invention is that they provide the specificity of flagellin together with the availability of rapid and efficient methods for recombinant and chemical synthesis of peptides. The immunomodulatory flagellin peptides of the invention can therefore be combined with numerous well known modes of administration for the treatment of a wide variety of pathological conditions.

In another embodiment, the invention provides a method of inducing an immune response in an individual by administering a vaccine containing an immunomodulatory flagellin peptide of the invention and an antigen. An immunomodulatory flagellin peptide of the invention functions to stimulate an innate immune response. The innate immune response involves the production of immunomodulatory molecules that beneficially promote the adaptive immune response. The adaptive immune response includes both humoral and cell-mediated immune responses to antigen. Thus, a flagellin peptide functions to boost either or both humoral and cell-mediated immune responses against the antigen. A boost in an immune response causes a general increase in immune system activity that can result in the destruction of foreign or pathologically aberrant cells that otherwise could have escaped the immune response.

As used herein, the term "flagellin" is intended to mean a flagellin polypeptide contained in a variety of Gram-positive or Gram-negative bacterial species. The nucleotide and amino acid sequences of flagellin from 22 bacterial species are depicted in FIG. 7. The nucleotide sequences encoding the listed flagellin polypeptides are publicly available in the NCBI Genbank database. The flagellin sequences from these and other species are intended to be encompassed by the term flagellin as used herein. Therefore, the sequence differences between species is included within the meaning of the term.

As used herein, the term "peptide" is intended to mean two or more amino acids covalently bonded together. The term "flagellin peptide" is intended to mean a peptide or fragment encoded by a portion of the nucleotide sequence or having a portion of the amino acid sequence which exhibits substantially the same sequence identity to the flagellin sequences as described above and identified in FIG. 7 and binds to toll-like receptor 5 (TLR5). For example, a flagellin peptide amino acid sequence is about 65% or greater in sequence identity to a portion of the S. Typhimurium1 sequence, GAVQNRFNSAIT, identified as SEQ ID NO:2, encoded by the nucleic acid sequence identified as SEQ ID NO:1. Therefore, flagellin peptides having amino acid substitutions that do not substantially alter TLR5 binding are included within the definition of a flagellin peptide. For example, flagellin peptides which contain one or more alanine substitutions and have substantially the same TLR5 binding activity as the flagellin peptide identified as SEQ ID NO:2 are included within the definition of a flagellin peptide. Exemplary flagellin peptides containing alanine substitutions and having substantially the same TLR5 binding activity as the flagellin peptide identified as SEQ ID NO:2 include, for example, GAVANRFNSAIT (SEQ ID NO:3) and GAVQNAFNSAIT (SEQ ID NO:4). Flagellin peptides consisting of greater than twelve amino acids and having TLR5 binding activity can similarly contain amino acid substitutions, so long as such substituted peptides retain substantially the same TLR5 binding activity. Examples of such flagellin peptides containing substitutions of various amino acid residues with alanine include ADTRDLGAVQNRFNSAIT (SEQ ID NO:37), VDARDLGAVQNRFNSAIT (SEQ ID NO:38) and VDTADLGAVQNRFNSAIT (SEQ ID NO:39). A flagellin peptide of the invention does not include a full length flagellin polypeptide. A flagellin peptide is intended to include molecules which contain, in whole or in part, non-amide linkages between amino acids, amino acid analogs and mimetics. Similarly, a flagellin peptide also includes cyclic peptides and other conformationally constrained structures. A flagellin peptide of the invention includes polypeptides having several hundred or more amino acid residues and can contain a heterologous amino acid sequence.

The term flagellin peptide specifically excludes fragments of flagellin described in Newton et al. *Science,* 244:70-72 (1989); Kuwajima, G., *J. Bacteriol.* 170:3305-3309 (1988); McSorley et al., *J. Immunol.* 164:986-993 (2000); and Samatey et al. *J. Struct. Biol.* 132:106-111 (2000).

As used herein, term "immunomodulatory flagellin peptide," is intended to mean a peptide or fragment having a portion of the amino acid sequence which exhibits substantially the same sequence identity to the flagellin sequences as described above and shown in FIG. 7 and binds to toll-like receptor 5 (TLR5). For example, an immunomodulatory flagellin peptide amino acid sequence is about 65% or greater in sequence identity to a portion of the S. Typhimurium1 sequence, GAVQNRFNSAIT, identified as SEQ ID NO:2, encoded by the nucleic acid sequence identified as SEQ ID NO:1. Therefore, immunomodulatory flagellin peptides having amino acid substitutions that do not substantially alter TLR5 binding are included within the definition of an immunomodulatory flagellin peptide. For example, immunomodulatory flagellin peptides which contain one or more alanine substitutions and have substantially the same TLR5 binding activity as the flagellin peptide identified as SEQ ID NO:2 are included within the definition of a flagellin peptide. Exemplary immunomodulatory flagellin peptides containing alanine substitutions and having substantially the same TLR5 binding activity as the flagellin peptide identified as SEQ ID NO:2 include, for example, GAVANRFNSAIT (SEQ ID NO:3) and GAVQNAFNSAIT (SEQ ID NO:4). Immunomodulatory flagellin peptides consisting of greater than twelve amino acids and having TLR5 binding activity can similarly contain amino acid substitutions, so long as such substituted peptides retain substantially the same TLR5 binding activity. Examples of such immunomodulatory flagellin peptides containing substitutions of various amino acid residues with alanine include ADTRDLGAVQNRFNSAIT (SEQ ID NO:37), VDARDLGAVQNRFNSAIT (SEQ ID NO:38) and VDTADLGAVQNRFNSAIT (SEQ ID NO:39). An immunomodulatory flagellin peptide of the invention does not include a full length flagellin polypeptide. An immunomodulatory flagellin peptide is intended to include molecules which contain, in whole or in part, non-amide linkages between amino acids, amino acid analogs and mimetics. Similarly, an immunomodulatory flagellin peptide also includes cyclic peptides and other conformationally constrained structures. An immunomodulatory flagellin peptide of the invention includes polypeptides having several hundred or more amino acid residues and can contain a heterologous amino acid sequence.

An immunomodulatory flagellin peptide, polypeptide or modification thereof, of the invention binds to toll-like receptor 5 (TLR5) and induces a TLR5-mediated response. It is understood that minor modifications can be made without destroying the TLR5 binding activity, TLR5-mediated response stimulating activity or immune response modulating activity of an flagellin peptide or polypeptide and that only a portion of the primary structure may be required in order to effect activity. Such modifications are included within the meaning of the terms flagellin polypeptide and flagellin peptide so long as TLR5 binding activity, TLR5 response stimulating or immune response stimulating activities are retained. Further, various molecules can be attached to flagellin polypeptides and peptides, including for example, other polypeptides, carbohydrates, nucleic acids or lipids. Such modifications are included within the definition of the term.

Minor modifications of flagellin polypeptide and peptides having at least about the same TLR5 binding activity, TLR5 response stimulating or immune response stimulating activity as the referenced polypeptide or peptide include, for example, conservative substitutions of naturally occurring amino acids and as well as structural alterations which incorporate non-naturally occurring amino acids, amino acid analogs and functional mimetics. For example, a Lysine (Lys) is considered to be a conservative substitution for the amino acid Arg. Similarly, a flagellin peptide containing mimetic structures having similar charge and spatial arrangements as reference amino acid residues would be considered a modification of the reference polypeptide or peptide so long as the peptide mimetic exhibits at least about the same activity as the reference peptide.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like. Amino acid analogs include modified forms of naturally and non-naturally occurring amino acids. Such modifications can include, for example, substitution or replacement of chemical groups and moieties on the amino acid or by derivitization of the amino acid. Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the $\epsilon$-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

Specific examples of amino acid analogs and mimetics can be found described in, for example, Roberts and Vellaccio, *The Peptides: Analysis, Synthesis, Biology*, Eds. Gross and Meinhofer, Vol. 5, p. 341, Academic Press, Inc., New York, N.Y. (1983), the entire volume of which is incorporated herein by reference. Other examples include peralkylated amino acids, particularly permethylated amino acids. See, for example, *Combinatorial Chemistry*, Eds. Wilson and Czarnik, Ch. 11, p. 235, John Wiley & Sons Inc., New York, N.Y. (1997), the entire book of which is incorporated herein by reference. Yet other examples include amino acids whose amide portion (and, therefore, the amide backbone of the resulting peptide) has been replaced, for example, by a sugar ring, steroid, benzodiazepine or carbo cycle. See, for instance, *Burger's Medicinal Chemistry and Drug Discovery*, Ed. Manfred E. Wolff, Ch. 15, pp. 619-620, John Wiley & Sons Inc., New York, N.Y. (1995), the entire book of which is incorporated herein by reference. Methods for synthesizing peptides, polypeptides, peptidomimetics and proteins are well known in the art (see, for example, U.S. Pat. No. 5,420,109; M. Bodanzsky, *Principles of Peptide Synthesis* (1st ed. & 2d rev. ed.), Springer-Verlag, New York, N.Y. (1984 & 1993), see Chapter 7; Stewart and Young, *Solid Phase Peptide Synthesis*, (2d ed.), Pierce Chemical Co., Rockford, Ill. (1984), each of which is incorporated herein by reference).

As used herein, the term "immune response" is intended to mean to a measurable or observable reaction to an antigen or immunomodulatory molecule mediated by one or more cells of the immune system. An immune response begins with an antigen or immunomodulatory molecule binding to an immune system cell and terminates with destruction of antigen and cells containing antigen or alteration in immune cell function. A reaction to an antigen or immunomodulatory molecule is mediated by many cell types, including a cell that initially binds to an antigen or immunomodulatory molecule and cells that participate in mediating an innate, humoral, cell-mediated immune response. An innate immune response involves binding of pathogen-associated molecular patterns (PAMPs) to cell surface receptors, such as toll-like receptors. Activation of toll-like receptors in response to PAMPs leads to the production of immunomodulatory molecules, such as cytokines and co-stimulatory molecules, that induce an immune response. A humoral response involves interaction of B cells with antigen and B cell differentiation into antibody-secreting cells. A cell-mediated response involves various subpopulations of T cells that recognize antigen presented on self-cells, including helper T cells that respond to antigen by producing cytokines and cytotoxic T cells that respond to antigen by developing into cytotoxic T lymphocytes, which mediate killing of altered self-cells. The term immune response includes measurable or observable reactions produced by any cell type that participates in the processes through which immune system cells are activated and antigen containing cells are destroyed. Such measurable reactions include, for example, production of immunomodulatory molecules, migration and proliferation.

An "immunomodulatory molecule" is a molecule that alters an immune response. An immunomodulatory molecule can be, for example, a compound, such as an organic chemical; a polypeptide, such as an antibody or cytokine; a nucleic acid, such as a DNA or RNA molecule; or any other type of molecule that alters an immune response. An immunomodulatory molecule can alter an immune response by directly or indirectly altering an activity of a cell that mediates an immune response. An immunomodulatory molecule can act directly on an immune system cell, for example, by binding to a cell surface receptor and stimulating or inhibiting proliferation, differentiation, or expression, secretion or receptor binding of immune system regulatory molecules such as co-stimulatory receptors and ligands, cytokines, and chemokines. Examples of naturally occurring molecules that act directly on immune system cells to alter an immune response include PAMPs, cytokines, chemokines and growth factors. Other examples of molecules that act directly on immune system cells to alter an immune response include molecules that alter receptor functions, such as antibodies to receptors, soluble cytokine receptors, receptor agonists and antagonists, molecules that alter the production of immunomodulatory molecules, such as inhibitors of converting enzymes and molecules involved in the intracellular transport and secretion of immunomodulatory molecules.

An immunomodulatory molecule can indirectly alter the activity of a particular immune system cell by altering the amount or activity of a molecule that regulates a cellular activity of the cell. For example, a cytokine, chemokine, or growth factor produced by an immune system cell, such as a macrophage, can stimulate or inhibit various cellular activities of B and T lymphocytes. Immune cell functions that can be stimulated or inhibited by an immunomodulatory molecule include, for example, immune cell activation, co-activation, proliferation, production of cytokines, cellular interactions and migration. An immunomodulatory molecule can therefore act on a variety of immune cell types and can alter a variety of cellular functions. An immunomodulatory flagellin peptide, polypeptide or modifications thereof used in the methods of the invention are examples of immunomodulatory molecules useful for inducing an immune response, for example, by binding to TLR5 and inducing a TLR5-mediated increase in macrophage production of TNFα, IL-1 and IL-6. The flagellin polypeptides, peptides and modifications thereof, are also useful for indirectly inducing an immune response because immunomodulatory molecules produced by a TLR5-expressing cell in response to flagellin will alter the activities of immune system cells that respond to the particular immunomodulatory molecules produced.

An immunomodulatory molecule can mediate an immune response that is specific for a target antigen or nonspecific. A specific immunomodulatory molecule alters an immune response to a particular target antigen. Examples of specific immunomodulatory molecules include monoclonal antibodies, including naked monoclonal antibodies, drug-, toxin- or radioactive compound-conjugated monoclonal antibodies, and ADCC targeting molecules. Such immunomodulatory molecules stimulate an immune response by binding to antigens and targeting cells for destruction. An immunomodulatory molecule can be used to suppress an immune response to an antigen. For example, a tolerogenizing molecule can be used to suppress an immune response to a self-antigen.

Nonspecific immunomodulatory molecules stimulate or inhibit the immune system in a general manner through various mechanisms that can include, for example, stimulating or suppressing cellular activities of immune system cells. Nonspecific immunomodulatory molecules useful for stimulating an immune responses include, for example, agents that stimulate immune cell proliferation, immune cell activation and production of cytokines and co-stimulatory molecules. Well known immunomodulatory molecules that stimulate an immune response are, for example, interleukins, interferons, levamisole and keyhole limpet hemocyanin. Nonspecific immunomodulatory molecules useful for suppressing immune responses include, for example, agents that inhibit cytokines synthesis or processing, specific cytokine receptor blocking reagents such as soluble receptors and receptor antagonists, and cytokines that down-regulate or inhibit the production of other immunomodulatory molecules. Well known immunomodulatory molecules for suppressing an immune response include, for example, cyclosporin, rapamycin, tacrolimus, azathioprine, cyclophosphamide and methotrexate.

Immunomodulatory molecules can be contained in a mixture of molecules, including a natural or man-made composition of molecules. Exemplary natural compositions of immunomodulatory compounds include, for example, those contained in an organism such as Bacille Calmette-Guerin (BCM) or *Corynbacterium parvum*. Exemplary man-made compositions of immunomodulatory molecules include, for example, QS-21, DETOX and incomplete Freund's adjuvant.

As used herein, the term "adjuvant" when used in reference to a vaccine, is intended to mean a substance that acts generally to accelerate, prolong, or enhance the quality of specific immune responses to a vaccine antigen. An adjuvant can advantageously reduce the number of immunizations or the amount of antigen required for protective immunization.

As used herein, the term "antigen-specific immune response" is intended to mean a reaction of one or more cells of the immune system to a particular antigen that is not substantially cross-reactive with other antigens.

As used herein, the term "antigen" is intended to mean a molecule which induces an immune response. An antigen can be a crude mixture of molecules, such as a cell, or one or more isolated molecules. Examples of crude antigens include attenuated organisms, inactivated organisms, viral particles and tumor cells. Examples of isolated antigens include a polypeptide, lipoprotein, glycoprotein, lipid, anti-idiotype antibody, toxoid, polysaccharide, capsular polysaccharide and nucleic acid. Such isolated antigens can be naturally occurring, recombinantly produced, or synthesized. Exemplary naturally occurring antigens include purified microbial macromolecules. Exemplary recombinantly produced antigens include cloned microbial and tumor cell antigens. Exemplary synthesized antigens include synthetic peptides and nucleic acids.

As used herein, the term "vaccine" is intended to mean a compound or formulation which, when administered to an individual, stimulates an immune response against an antigen. A vaccine is useful for preventing or ameliorating a pathological condition that will respond favorably to immune response modulation. A vaccine can contain isolated or crude antigen, and can contain one or more antigens. A vaccine can contain one or more adjuvants.

As used herein, the term "immunogenic amount" is intended to mean an amount of an immunomodulatory flagellin polypeptide, peptide or modifications thereof, or combinations thereof with one or more molecules, such as an antigen or other immunomodulatory molecule, required to effect an immune response. The dosage of an immunomodulatory flagellin polypeptide, peptide, or modifications thereof, independently or in combination with one or more molecules, will depend, for example, on the pathological condition to be treated, the weight and condition of the individual and previous or concurrent therapies. The appropriate amount considered to be an immunogenic dose for a particular application of the method can be determined by those skilled in the art, using the guidance provided herein. For example, the amount can be extrapolated from in vitro or in vivo assays as described below. Those skilled in the art will understand that the condition of the patient needs to be monitored through the course of therapy and that the amount of the composition that is administered can be adjusted according to patient response to therapy.

The term "pathologically aberrant cell" is intended to mean a cell that is altered from a normal physiological or cellular state. Such alteration can be due to changes in physiology or phenotype associated with a disease or abnormal condition of a mammalian cell or tissue. Pathologically aberrant cells include cells lacking normal control of cellular functions, such as growth, differentiation, and apoptosis, resulting in altered gene and protein expression. Cells that lack normal growth control proliferate in the absence of appropriate growth signals, resulting in damage in structure or function of surrounding tissues. Cells that lack normal differentiation undergo inappropriate phenotypic or physiological changes that do not normally characterize the cell type, resulting in damage in structure and function or surrounding tissues. Cells that lack normal apoptosis fail to undergo, or inappropriately undergo the process of cell death, resulting in damage in structure or function of surrounding tissues. Altered protein expression is an example of a phenotype change that renders such cells distinguishable from normal. For example, increased or decreased expression of a polypeptide normally expressed on a cell, expression of a mutated polypeptide and expression of a polypeptide not normally expressed on a cell are phenotypic changes that can alter a cell from normal. Examples of pathologically aberrant cells include tumor cells and degenerating cells.

As used herein, the term "pathological condition" is intended to mean a disease, abnormal condition or injury of a mammalian cell or tissue. Such pathological conditions include, for example, hyperproliferative and unregulated neoplastic cell growth, degenerative conditions, inflammatory diseases, autoimmune diseases and infectious diseases. Pathological conditions characterized by excessive or unregulated cell growth include, for example, hyperplasia, cancer, autoimmune disease and infectious disease. Hyperplastic and cancer cells proliferate in an unregulated manner, causing destruction of tissues and organs. Specific examples of hyperplasias include benign prostatic hyperplasia and endometrial hyperplasia. Specific examples of cancer include prostate, breast, ovary, lung, uterus, brain and skin cancers. Abnormal cellular growth can also result from infectious diseases in which foreign organisms cause excessive growth. For example, human papilloma viruses can cause abnormal growth of skin cells. The growth of cells infected by a pathogen is abnormal due to the alteration of the normal condition of a cell resulting from the presence of a foreign organism. Specific examples of infectious diseases include DNA and RNA viral diseases, bacterial diseases, parasitic diseases. Similarly, the growth of cells mediating autoimmune and inflammatory diseases are aberrantly regulated which results in, for example, the continued proliferation and activation of immune mechanisms with the destruction of tissues and organs. Specific examples of autoimmune diseases include, for example, rheumatoid arthritis and systemic lupus erythmatosis. Specific examples of degenerative disease include osteoarthritis and Alzheimer's disease.

By specific mention of the above categories of pathological conditions, those skilled in the art will understand that such terms include all classes and types of these pathological conditions. For example, the term cancer is intended to include all known cancers, whether characterized as malignant, benign, soft tissue or solid tumor. Similarly, the terms infectious diseases, degenerative diseases, autoimmune diseases and inflammatory diseases are intended to include all classes and types of these pathological conditions. Those skilled in the art will know the various classes and types of proliferative, infectious, autoimmune and inflammatory diseases.

As used herein the term "toll-like receptor 5" or "TLR5" is intended to mean a toll-like receptor 5 of any species, such as the murine and human polypeptides containing the amino acid sequences set forth as SEQ ID NOS:6 and 8, respectively, encoded by the nucleic acid sequence identified as SEQ ID NOS:5 and 7, respectively. A TLR5 is activated upon binding to flagellin, an immunomodulatory flagellin peptide, or modifications thereof, and other TLR5 agonists. Upon activation, a TLR5 induces a cellular response by transducing an intracellular signal that is propagated through a series of signaling molecules from the cell surface to the nucleus. For example, the intracellular domain of TLR5 recruits an adaptor protein, MyD88, which recruits the serine kinase IRAK. IRAK forms a complex with TRAF6, which then interacts with various molecules that participate in transducing the TLR signal. These molecules and other TRL5 signal transduction pathway components stimulate the activity of transcription factors, such as fos, jun and NF-κB, and the corresponding induction of gene products of fos-, jun- and NF-κB-regulated genes, such as, for example, TNFα, IL-1 and IL-6. The activities of signaling molecules that mediate the TLR5 signal, as well as molecules produced as a result of TLR5 activation are TLR5 activities that can be observed or measured. Therefore, a TLR5 activity includes binding to a flagellin polypeptide, immunomodulatory flagellin peptide, or a modification thereof, recuitment of intracellular signaling molecules, as well as downstream events resulting from TLR5 activation, such as transcription factor activation and production of immunomodulatory molecules. A TLR5 cellular response mediates an innate immune system response in an animal because cytokines released by TLR5-expressing cells regulate other immune system cells to promote an immune response in an animal. Therefore, as used herein the term "TLR5-mediated response" is intended to mean the ability of a flagellin polypeptide, immunomodulatory peptide or modification thereof to induce a TLR5-mediated cellular response. Exemplary TLR5-mediated cellular responses include activation of transcription factors such as fos, jun and NF-κB, production of cytokines such as IL-1, IL-6 and TNFα, and the stimulation of an immune response in an animal.

A TLR5 also encompasses polypeptides containing minor modifications of a native TLR5, and fragments of a full-length native TLR5, so long as the modified polypeptide or fragment retains one or more biological activities of a native TLR5, such as the abilities to stimulate NF-κB activity, stimulate the production of cytokines such as TNFα, IL-1, and IL-6 and stimulate an immune response in response to TLR5 binding to flagellin polypeptide, immunomodulatory peptide or modifications thereof. A modification of a TLR5 can include additions, deletions, or substitutions of amino acids, so long as a biological activity of a native TLR5 is retained. For example, a modification can serve to alter the stability or activity the polypeptide, or to facilitate its purification. Modifications of polypeptides as described above in reference to flagellin polypeptides and peptides are applicable to TLR5 polypeptides of the invention. A "fragment" of a TLR5 is intended to mean a portion of a TLR5 that retains at least about the same activity as a native TLR5.

As used herein, the term "TLR5 agonist" refers to a compound that selectively activates or increases normal signal transduction through TLR5. As used herein, the term "TLR5 antagonist" refers to a compound that selectively inhibits or decreases normal signal transduction through TLR5. A TLR5 agonist or antagonist can alter normal signal transduction through TLR5 indirectly, for example, by modifying or altering the native conformation of TLR5 or a TLR5 ligand. For therapeutic applications, a TLR5 agonist or antagonist has an EC50 of less than about $10^{-7}$ M, such as less than $10^{-8}$ M and less than $10^{-9}$ M, although a TRL5 agonist with a higher EC50 can be therapeutically useful. As used herein, the term "TLR5 ligand" refers to a compound that binds a TLR5 polypeptide with high affinity. A TLR5 ligand can further be an agonist or antagonist of TLR5, as described above, or can be a compound having little or no effect on TLR5 signaling.

As used herein, the term "detectably labeled" refers to derivitization with, or conjugation to, a moiety that is detectable by an analytical or qualitative method. A detectable moiety can be, for example, a radioisotope, such as $^{14}C$, $^{131}I$, $^{32}P$ or $^{3}H$, fluorochrome, ferromagnetic substance, or luminescent substance.

As used herein the term "ADCC targeting molecule" is intended to mean an antigen binding protein containing a Fc receptor binding domain capable of inducing antibody-dependent cell cytotoxicity (ADCC). An ADCC targeting molecule can also contain other domains that augment induction of ADCC. The flagellin polypeptides and peptides, immunomodulatory peptides, and modifications described herein, can be domains of an ADCC targeting molecule that augment induction of ADCC. The ADCC targeting molecule can include multiple valencies for either or both the antigen binding domain or the Fc receptor binding domain. Additionally, an ADCC targeting molecule also can have multiple different antigen binding domains combined with a single or multiple copies of an Fc receptor binding domain or combined with different Fc receptor binding domains. The antigen binding domain or domains can be derived from essentially any molecule that has selective or specific binding activity to a target antigen so long as it can be fused or attached to one or more Fc receptor binding domains while still maintaining antigen binding activity. The Fc receptor binding domain can be derived from an antibody constant region of, for example, the IgG class, including subclasses IgG1, IgG3 and IgG4. Such Fc receptor binding domains can be used in their native form or the amino acid sequence can be modified so as to enhance or optimize the Fc receptor binding or ADCC activity. Moreover, the Fc receptor binding domains can be derived from constant regions which recognize either stimulatory or inhibitory Fc receptors. The Fc receptor binding domain is located within the hinge region of an antibody constant region where the cognate receptors bound by this domain include, for example, the Fc RI, Fc RIIA and Fc RIII. Therefore, ADCC targeting molecules include, for example, antibodies selective for a target antigen and functional variants thereof as well as fusion proteins and chemical conjugates containing both an antigen binding domain and a Fc receptor binding domain in functionally active forms. ADCC targeting molecules and the use of ADCC targeting molecules in the treatment of disease are described in detail in U.S. patent application Ser. No. 09/618,176, which is incorporated herein by reference.

The term "about" when used in reference to a particular activity or measurement is intended to refer to the referenced activity or measurement as being within a range values encompassing the referenced value and within accepted standards of a credible assay within the art, or within accepted statistical variance of a credible assay within the art.

As used herein, the term "substantially" or "substantially the same" when used in reference to an amino acid sequence is intended to mean that the amino acid sequence shows a considerable degree, amount or extent of sequence identity when compared to the reference sequence. Such considerable degree, amount or extent of identity is further considered to be significant and meaningful and therefore exhibit characteristics which are definitively recognizable or known as being derived from or related to flagellin. For example, an amino acid sequence which is substantially the same amino acid sequence as an flagellin peptide, including fragments thereof, refers to a sequence which exhibits characteristics that are definitively known or recognizable as being sufficiently related to flagellin so as to fall within the classification of flagellin sequences as defined above. Minor modifications thereof are included so long as they are recognizable as an flagellin sequence as defined above.

As used herein, the term "individual" is intended to mean any animal in which an immune response can be induced by a flagellin polypeptide, peptide or modifications thereof including a human, non-human primate, cow, pig, chicken, rabbit, ferret, rat or mouse.

An immunomodulatory flagellin polypeptide, peptide or modifications thereof can be used to induce an immune response in an individual having a pathological condition, promoting the individual's own immune system to function more effectively and thereby ameliorate the pathological condition. An individual's immune system may not recognize cancer cells and other types of pathologically aberrant cells as foreign because the particular antigens are not different enough from those of normal cells to cause an immune reaction. In addition, the immune system may recognize cancer cells, but induce a response insufficient to destroy the cancer. By stimulating an innate immune response, immunomodulatory flagellin peptide, polypeptide or modification thereof, promote humoral and cell-mediated responses to antigens on foreign cells or pathologically aberrant cells, such as cancer cells. Administered independently or in combination with an antigen, such as a tumor antigen, a flagellin polypeptide, peptide or modification thereof, can be used to boost the immune system's recognition of cancer cells and other pathologically aberrant cells, and target such cells for destruction.

Flagellin is a pathogen-associated molecular pattern (PAMP) recognized by toll-like receptor 5 (TRL5). Toll-like receptor 5 is a member of a family of at least 10 receptors involved in mediated the innate immune response. Toll-like receptors recognize PAMPs that distinguish infectious agents from self and mediating the production of immunomodulatory molecules, such as cytokines, necessary for the development of effective adaptive immunity (Aderem, A. and Ulevitch, R. J. Nature 406:782-787 (2000) and Brightbill, H. D., Immunology 101: 1-10 (2000)). Members of the toll-like receptor family recognize a variety of antigen types and can discriminate between pathogens. For example, TLR2 recognizes various fungal, Gram-positive, and mycobacterial components, TLR4 recognizes the Gram-negative product lipopolysaccharide (LPS), and TLR9 recognizes nucleic acids such as CpG repeats in bacterial DNA. TLR5 has now been identified as a receptor for bacterial flagellin.

Flagellin induces an innate immune response by binding to and activating TLR5. Activation of TLR5 by binding to flagellin induces the production of immunomodulatory molecules, such as cytokines and co-stimulatory molecules, by a TLR5-expressing cell. For example, activation of TLR5 in macrophages results in the expression of the cytokines TNFα, IL-1 and IL-6. These cytokines directly and indirectly alter the activities of immune system cells that participate in both humoral (TH2) and cell-mediated (TH1) adaptive immune responses. In this manner, an immunomodulatory flagellin peptide, polypeptide or modification thereof, acts as an adjuvant to stimulate a general immune response.

Altering the balance of TH1- versus TH2-associated cytokines can be used to favorably alter an immune response to treat certain diseases. For example, in the use of cancer vaccines, it can be favorable to induce both TH1 and TH2 responses (Herlyn and Birebent, Ann. Med., 31:66-78, (1999)). Different sets of cytokines orchestrate TH1 and TH2 immune responses. For example, TH1 immune responses are associated with the cytokines IL-2, IFN-γ, and TNFα while TH2 immune responses are associated with the cytokines IL-4, IL-5, IL-6 and IL-10. TLR5 stimulates the production of cytokines associated with both TH1- and TH2-associated cytokines. For example, TNFα is associated with the stimulation of a TH1 type immune response (Ahlers, J D et al. J. Immunol, 158:3947-58 (1997)), and IL-6 is associated with the stimulation of a TH2 type response (Steidler, L. et al. Infect. Immun., 66:3183-9, (1998)). Therefore, an immunomodulatory flagellin peptide, polypeptide or modification thereof, can be used to advantageously elicit TH1 and TH2 type immune responses.

An immunomodulatory flagellin peptide, polypeptide or modification thereof can also be used to generally alter the particular cytokines involved in an immune response in an individual. Alterations from normal levels of cytokines are observed in many disease states. For this reason, it can be desirable to increase or decrease the amounts or activities of specific cytokines involved in particular pathological conditions. The cytokines produced in response to TLR5 activation can both stimulate and down-regulate the production of other cytokines. Therefore, an immunomodulatory flagellin peptide, polypeptide or modification thereof, or combination of a flagellin molecule with an immunomodulatory molecule or antigen can be used to alter levels of cytokines associated with a pathological condition. For example, an immunomodulatory flagellin peptide can increase TLR5-expressing macrophage production of TNFα, IL-1 and IL-6. TNFα and IL-1 generally function as pro-inflammatory cytokines. IL-6 generally functions as an anti-inflammatory cytokine and induces a variety of anti-inflammatory activities in immune system cells. For example, IL-6 stimulates the production of many anti-inflammatory anti-proteases. Those skilled in the art will be able to determine if a pathological condition in an individual could be ameliorated by inducing TLR5-stimulated cytokine production and will be able to determine appropriate combinations of flagellin and immunomodulatory molecules suitable for inducing a beneficial immune response.

The invention provides an immunomodulatory flagellin peptide comprising at least about 10 amino acids of substantially the amino acid sequence GAVQNRFNSAIT (SEQ ID NO:2), or a modification thereof, that binds to toll-like receptor 5 (TLR5).

The flagellin peptide identified by SEQ ID NO:2 is a peptide of *S. Typhimurium*1 flagellin which is encoded by the nucleic acid sequence identified by SEQ ID NO:1. A flagellin peptide of the invention also includes peptides from other bacterial species, such as *H. Pylori* (SEQ ID NO:12), *V. Cholera* (SEQ ID NO:13), *S. marcesens* (SEQ ID NO:20), *S. flexneri* (SEQ ID NO:22), *T. Pallidum* (SEQ ID NO:23 or SEQ ID NO:24), *L. pneumophila* (SEQ ID NO:25), *B burgdorferei* (SEQ ID NO:26), *C. difficile* (SEQ ID NO:28), *R. meliloti* (SEQ ID NO:29), *A. tumefaciens* (SEQ ID NO:30), *R. lupini* (SEQ ID NO:31), *B. clarridgeiae* (SEQ ID NO:33), *P. Mirabilis* (SEQ ID NO:16), *B. subtilus* (SEQ ID NO:27), *L. monocytogenes* (SEQ ID NO:32), *P. aeruginosa* (SEQ ID NO:14) and *E. coli* (SEQ ID NO:21), which contain amino acid sequences having 21-71% identity over the 12 amino acid sequence of SEQ ID NO:2. A flagellin peptide of the invention also includes flagellin peptides from other bacterial species, including peptides contained within the flagellin amino acid sequences shown FIG. 7. Thus, a flagellin peptide of the invention can have greater than about 65% identity, such as greater than about 75%, greater than about 85%, greater than about 95%, greater than about 98% identity with the peptide identified by SEQ ID NO:2.

A flagellin peptide of the invention is derived from a conserved region of a flagellin polypeptide. Conserved regions of flagellin are well known in the art and have been described, for example, in Mimori-Kiyosue, et al., *J. Mol. Viol.* 270:222-237, (1997). Whereas T cell receptors which mediate the adaptive immune response recognize random portions of antigen amino acid sequences, toll-like receptors recognize conserved portions of antigen amino acid sequences. Therefore, the flagellin peptides of the invention and immunomodulatory flagellin peptides used in the methods of the invention contain amino acid sequences derived from conserved regions of flagellin.

A flagellin peptide of the invention excludes a portion of flagellin described in Newton et al. (supra, 1989), which consists of an *S. meunchen* flagellin fragment containing a deletion of amino acids 207-223, portions of *E. coli* (strain K12) flagellin described in Kuwaijima et al. (supra, 1998), which consist of *E. coli* flagellin fragments containing deletions of amino acids 239-254, 259-278, 237-262, 194-379, 201-318, 218-326, 211-347, 210-299, 245-301, and 220-299, a portion of flagellin described in Samatey et al. (supra, 2000), which consists of an *S. typhimurium* flagellin fragment lacking 52 N-terminal amino acid residues and lacking 44 C-terminal amino acid residues, and portions of flagellin described in McSorley et al. (supra, 2000) which consist of *S. typhimurium* flagellin fragments having the following amino acid sequences: RSDLGAVQNRFNSAI (SEQ ID NO:40), DLGAVQNRFNSAITN (SEQ ID NO:41), GAVQNRFNSAITNLG (SEQ ID NO:42) AND VQNRFNSAITNLGNT (SEQ ID NO:43).

An immunomodulatory flagellin peptide of the invention can contain a heterologous amino acid sequence that imparts structural or functional characteristics onto the flagellin peptide. For example, chimeric flagellin peptides or modifications can be used to impart a targeting function. Targeting of a flagellin peptide or modification to a particular site, such as a mucosal surface for example, confers additional therapeutic advantage of inducing an immune response at a site of pathological condition or a site favored for inducing an antigen-specific immune response, for example by a vaccine. Further, chimeric flagellin peptides can include a sequence that facilitates detection, purification or enhances immunomodulatory activity of the flagellin peptide. A flagellin peptide can be contained, for example, in an ADCC targeting molecule used to treat a pathological condition. A flagellin peptide can augment the effectiveness of an ADCC targeting molecule by, for example, stimulating an innate immune response through TLR5, such as the induction of cytokines such as TNFα, IL-1 and IL-6. Similarly, a flagellin peptide can contain amino acid sequences of a variety of antigen polypeptides, such as those described above in reference to antigens contained in vaccines used in the methods of the invention. A chimeric flagellin peptide containing amino acid sequences of an antigen or containing an antigenic molecule such as a carbohydrate, nucleic acid, or lipid, can be used analogously to a vaccine, as described above, as well as in a vaccine formulation, to induce an immune response in an individual. As such, a chimeric flagellin peptide can be a vaccine that induces both innate and adaptive immune system responses.

An immunomodulatory flagellin peptide of the invention can be prepared by a variety of methods well-known in the art, for example, by recombinant expression systems described below, and biochemical purification methods described below, as well as by synthetic methods well known in the art. Methods for recombinant expression and purification of polypeptides in various host organisms are described, for example, in Sambrook et al., *Molecular Cloning: A Laboratory Manual*, Cold Spring Harbor Laboratory, New York (1992) and in Ansubel et al., *Current Protocols in Molecular Biology*, John Wiley and Sons, Baltimore, Md. (1998), both of which are incorporated herein by reference. Similarly, flagellin peptide modifications can be generated using recombinant mutagenesis, such as site directed mutagenesis and PCR mutagenesis, and expression of the flagellin peptide modification. Numerous methods of constructing, modifying, expressing and purifying peptides are known to those skilled in the art. A specific example of a method for purifying flagellin is described below in Example III. The choice of recombinant methods, expression and purification systems will be known by those skilled in the art and will depend on the user and the particular application for the immunomodulatory flagellin peptide or modification thereof.

A flagellin peptide of the invention induces an innate immune response in an individual by binding to an stimulating TLR5. Therefore, the invention provides methods for inducing an immune response in an individual having a pathological condition that can be ameliorated by immune system activity. The methods involve administering an immunomodulatory flagellin peptide or modification thereof to induce an immune response, administering a combination of an immunomodulatory flagellin peptide and an antigen to induce an antigen-specific immune response, and administering a combination of an immunomodulatory flagellin peptide and an immunomodulatory molecule to modulate an immune response. The selection of a particular method for inducing an immune response will depend on the particular pathological condition to be ameliorated or prevented in an individual. As described herein, the methods are applicable to a wide variety of pathological conditions. Those skilled in the art will be able to determine if an immune response can be beneficially modulated by administering an immunomodulatory flagellin peptide or combination thereof with an antigen or immunomodulatory molecule.

The invention provides method of inducing an antigen-specific immune response in an individual. The method involves administering to an individual an immunogenic amount of a vaccine, comprising an antigen and an immunomodulatory flagellin peptide having at least about 10 amino acids of substantially the amino acid sequence of SEQ ID NO:2, or a modification thereof.

As an adjuvant in a vaccine formulation, the immunomodulatory flagellin peptides of the invention can contribute to the effectiveness of the vaccine by, for example, enhancing the immunogenicity of weaker antigens such as highly purified or recombinant antigens, reducing the amount of antigen required for an immune response, reducing the frequency of immunization required to provide protective immunity, improve the efficacy of vaccines in individuals with reduced or weakened immune responses, such as newborns, the aged, and immunocompromised individuals, and enhance the immunity at a target tissue, such as mucosal immunity, or promote cell-mediated or humoral immunity by eliciting a particular cytokine profile. An immunomodulatory flagellin peptide, polypeptide or modification thereof induces an innate immune response through activation of TLR5. The innate immune response increases the immune response to an antigen by stimulating the adaptive immune response. Therefore, a combination of an immunomodulatory flagellin peptide, polypeptide or modification thereof with one or more antigens provides an effective vaccine for inducing an immune response in an individual.

The methods of the invention for inducing an antigen-specific immune response can be used to treat individuals having a variety of pathological conditions. For example, cancer vaccines have been used effectively for treating melanoma and breast cancers. Vaccines have been used for treatment of inflammatory diseases such as asthma (Scanga C. B and Le Gros, G., *Drugs* 59(6), 1217-1221 (2000)), infectious diseases of pathogenic bacteria such as *H. pylori*, pathogenic viruses such as human papilloma virus and HIV (Sutton P. and Lee, A, *Aliment Pharmacol.* 14:1107-1118 (2000)), protozoa, autoimmune diseases such as diabetes (von Herrath and Whitton, *Ann. Med.* 32:285-292 (2000)) and degenerative diseases such as Alzheimer's disease (Youngkin, S. G., *Nat. Med.,* 7(1):18-19 (2001)). Therefore, a vaccine used in the methods of the invention for inducing an antigen-specific immune response can be administered to an individual for treatment of a variety of pathological conditions, including proliferative disease, infectious disease, inflammatory disease and degenerative disease.

A variety of antigens can be used in combination with an immunomodulatory flagellin peptide of the invention for preparing a vaccine. Microorganisms such as viruses, bacteria and parasites contain substances that are not normally present in the body. These substances can be used as antigens to produce an immune response to destroy both the antigen and cells containing the antigen, such as a bacterial cell or cancer cell.

For example, isolated or crude antigens of microbial pathogens can be used in vaccines to treat infectious disease; isolated or crude tumor cell antigens can be used in vaccines to treat cancer; isolated or crude antigens known to be associated with a pathologically aberrant cell can be used to treat a variety of diseases in which it is beneficial to target particular cells for destruction.

A variety of substances can be used as antigens in a vaccine compound or formulation. For example, attenuated and inactivated viral and bacterial pathogens, purified macromolecules, polysaccharides, toxoids, recombinant antigens, organisms containing a foreign gene from a pathogen, synthetic peptides, polynucleic acids, antibodies and tumor cells can be used to prepare a vaccine useful for treating a pathological condition. Therefore, an immunomodulatory flagellin peptide of the invention can be combined with a wide variety of antigens to produce a vaccine useful for inducing an immune response in an individual. Those skilled in the art will be able to select an antigen appropriate for treating a particular pathological condition and will know how to determine whether a crude or isolated antigen is favored in a particular vaccine formulation.

An isolated antigen can be prepared using a variety of methods well known in the art. A gene encoding any immunogenic polypeptide can be isolated and cloned, for example, in bacterial, yeast, insect, reptile or mammalian cells using recombinant methods well known in the art and described, for example in Sambrook et al., *Molecular Cloning: A Laboratory Manual*, Cold Spring Harbor Laboratory, New York (1992) and in Ansubel et al., *Current Protocols in Molecular Biology*, John Wiley and Sons, Baltimore, Md. (1998). A number of genes encoding surface antigens from viral, bacterial and protozoan pathogens have been successfully cloned, expressed and used as antigens for vaccine development. For example, the major surface antigen of hepatitis B virus, HbsAg, the β subunit of choleratoxin, the enterotoxin of *E. coli*, the circumsporozoite protein of the malaria parasite, and a glycoprotein membrane antigen from Epstein-Barr virus, as well as tumor cell antigens, have been expressed in various well known vector/host systems, purified and used in vaccines. An immunomodulatory flagellin peptide, polypeptide or modification thereof induces an innate immune response through TLR5 that can beneficially enhance an immune response to a recombinant antigen.

A pathologically aberrant cell to be used in a vaccine can be obtained from any source such as one or more individuals having a pathological condition or ex vivo or in vitro cultured cells obtained from one or more such individuals, including a specific individual to be treated with the resulting vaccine.

Those skilled in the art will be able to determine if a vaccine compound or formulation induces an innate, humoral, cell-mediated, or any combination of these types of immune response, as methods for characterizing these immune responses are well known in the art. For example, the ability of a vaccine compound or formulation to induce an innate immune response through TLR5 can be determined using methods described herein as well as other methods. Such methods for detecting an innate immune response can be generally performed within hours of vaccine administration. The ability of a vaccine compound or formulation to induce a humoral response can be determined by measuring the titer of antigen-specific antibodies in an animal primed with the vaccine and boosted with the antigen, or determining the presence of antibodies cross-reactive with an antigen by ELISA, Western blotting or other well-known methods. Cell-mediated immune responses can be determined, for example, by measuring cytotoxic T cell response to antigen using a variety of methods well known in the art. Methods of detecting humoral and cell-medicated immune responses can be generally performed days or weeks after vaccine administration.

A combination of an antigen or immunomodulatory molecule and an immunomodulatory flagellin peptide, polypeptide or modification thereof, can be tested in a variety of preclinical toxicological and safety studies well known in the art. For example, such a combination can be evaluated in an animal model in which the antigen has been found to be immunogenic and that can be reproducibly immunized by the same route proposed for human clinical testing. A combination of an antigen or immunomodulatory molecule and an immunomodulatory flagellin peptide or modification thereof can be tested, for example, by an approach set forth by the Center for Biologics Evaluation and Research/Food and Drug Administration and National Institute of Allergy and Infectious Diseases (Goldenthal, K L et al. *AID Res Hum Retroviruses*, 9:S45-9 (1993)).

Those skilled in the art will know how to determine for a particular combination of antigen or immunomodulatory molecule and immunomodulatory flagellin polypeptide modification thereof, the appropriate antigen payload, route of immunization, volume of dose, purity of antigen, and vaccination regimen useful to treat a particular pathological condition in a particular animal species.

The invention provides a method of inducing a TLR5-mediated response. The method involves administering to a TLR5-containing cell an effective amount of an immunomodulatory flagellin peptide having at least about 10 amino acids of substantially the amino acid sequence of SEQ ID NO:2, or a modification thereof.

A TLR5-mediated response can be assessed in a cell or animal because TLR5 stimulates cellular activities that stimulate the immune response that occurs in an animal. For example, flagellin binding to TLR5 induces cellular events such as an increase in the amount or activity of cytokines, such as TNFα, IL-1 and IL-6. These cytokines in turn regulate the activities of immune system cells. Therefore a TLR5-mediated response can be determined by examining an immune responses in an animal and by observing particular immune system cell activities. Determination of immune responses in an animal is discussed below. Determination of immune system cell activities can be performed, for example, by observing or measuring the amount of activity of immunomodulatory molecules produced by specific types of immune cells. Cytokine production by macrophages is an exemplary immune cell activity that can be conveniently measured using methods well known in the art and those described herein. A biological activity of a cytokine can also be assessed using methods well known in the art. TNFα activities include, for example, inducing the production of IL-1 and IL-6, activation of neutrophils and endothelial cells in inflammation, inducing acute phase reactants in liver, inducing fever. IL-1 activities include, for example, activating of endothelial cells in inflammation and coagulation, inducing acute phage reactants in liver, inducing fever and stimulating T cell proliferation. IL-6 activities include, for example, stimulating proliferation of mature B cells and inducing their final maturation into antibody-producing plasma cells, inducing IL-2 receptor expression, inducing acute phase reactants in liver, and co-stimulation of thymocytes in vitro. A regulatory effect of IL-6 is inhibition of TNFα production, providing negative feedback for limiting the acute inflammatory response (Feghali, C. A. and Wright, T. M., *Frontiers in Bioscience*, 2, d12-26 (1997) provides a summary of cytokine activities).

The invention provides a method of inducing an immune response in an individual having a pathological condition. The method involves administering to said individual an immunogenic amount of an immunomodulatory flagellin peptide having at least about 10 amino acids of substantially the amino acid sequence of SEQ ID NO:2, or a modification thereof.

As described above, an immunomodulatory flagellin peptide can be used to beneficially boost a general immune response in an individual having a pathological condition by stimulating an innate immune response. An increased immune response can ameliorate a pathological condition as well as prevent a pathological condition in a healthy individual, or individual not having a pathological condition. Therefore, an immunomodulatory flagellin peptide can be administered prophylactically to an individual not having a pathological condition, if desired.

The invention provides another method of modulating an immune response in an individual having a pathological condition. The method involves administering to the individual a combination of an immunogenic amount of an immunomodulatory flagellin peptide having at least about 10 amino acids of substantially the amino acid sequence of SEQ ID NO:2, or a modification thereof, and another immunomodulatory molecule.

As described above, a combination of an immunomodulatory flagellin peptide with another immunomodulatory molecule can be used to advantageously induce or modulate an immune response. An immune response can be induced by combining an immunomodulatory flagellin peptide with another immunomodulatory molecule that induces an immune response in a general manner, such as an adjuvant, or can be combined with an immunomodulatory molecule that induces a particular alteration in an immune cell activity. Such immunomodulatory molecules are described herein.

Modulating an immune response is useful for promoting a more effective or more normal immune response in an individual having a pathological condition. As described above, alterations in normal cytokine levels are associated with various pathological conditions. An immunomodulatory flagellin peptide or combination with another immunomodulatory molecule can be used to modulate cytokine levels in an individual by inducing the production of immunomodulatory molecules, such as cytokines including TNFα, IL-1, and IL-6 through TLR5, and inducing the production of suppression of the same or different immunomodulatory molecules through the activity of the administered immunomodulatory molecule.

Therefore, the immunomodulatory flagellin peptides of the invention can be combined with immunomodulatory molecules that alter an immune response by stimulating or inhibiting the cellular functions of immune system cells.

A variety of immunomodulatory molecules can be used in combination with an immunomodulatory flagellin peptide or modification thereof of the invention to alter an immune response in an individual. The type of alteration desired will determine the type of immunomodulatory molecule selected to be combined with an immunomodulatory flagellin peptide. For example, to promote an innate immune response, a immunomodulatory flagellin peptide can be combined with another immunomodulatory molecule that promotes an innate immune response, such as a PAMP or conserved region known or suspected of inducing an innate immune response. A variety of PAMPs are known to stimulate the activities of different members of the toll-like family of receptors. Such PAMPs can be combined to stimulate a particular combination of toll-like receptors that induce a beneficial cytokine profile. For example, PAMPs can be combined to stimulate a cytokine profile that induces a TH1 or TH2 immune response.

Other types of immunomodulatory molecules that promote humoral or cell-mediated immune responses can be combined with a flagellin molecule of the invention. For example, cytokines can be administered to alter the balance of TH1 and TH2 immune responses. Those skilled in the art will know how to determine the appropriate cytokines useful for obtaining a beneficial alteration in immune response for a particular pathological condition.

Immunomodulatory molecules that target antigens and cells displaying antigens for destruction can be combined with a flagellin molecule of the invention. For example, the effectiveness of monoclonal antibodies and ADCC targeting molecules that recognize a particular antigen on an unwanted cell, such as a pathologically aberrant cell can be increased when administered with a flagellin molecule of the invention. Immunomodulatory molecules that stimulate or suppress cellular activities such as proliferation, migration, activation, interaction and differentiation can be combined with a flagellin molecule of the invention. For example, IL-2 can be used to stimulate proliferation of immune system cells, certain interferons can be used to interfere with the rapid growth of cancer cells or to interfere with angiogenesis, and ganulocyte-colony stimulating factor can be used to increase production of certain types of immune system cells and blood cells. A variety of immunostimulating and immunosupressing molecules and modalities are well known in the art and can be used in combination with a flagellin polypeptide, peptide or modification thereof, of the invention. A flagellin molecule of the invention increases the beneficial effect of an immunomodulatory molecule by inducing TLR5-mediated production of immunomodulatory molecules that function in concert with a selected immunomodulatory molecule to produce a desired cytokine profile or cellular activity, or prime the adaptive immune response to respond to the selected immunomodulatory molecule.

The methods of the invention for using immunomodulatory flagellin peptides to induce an immune response are also applicable to a flagellin polypeptide, or a modification thereof. Accordingly, the invention provides a method of inducing an immune response in an individual, including a human, having a pathological condition. The method involves administering to the individual an immunogenic amount of an immunomodulatory flagellin polypeptide, or modification thereof, when the flagellin polypeptide induces an immune response.

An immunomodulatory flagellin peptide of the invention binds to TLR5 and stimulates a TLR5 activity. The ability of an immunomodulatory flagellin peptide or modification thereof to bind to TLR5 or stimulate a TLR5 activity can be determined using methods known in the art. Methods of determining specific binding interactions of flagellin peptides and modifications thereof with TLR5 can be determined using well known methods in the art such as methods of trapping ligand-receptor complexes using chemical cross-linking, and competitive inhibition of reagents specific for TLR5 such as specific flagellin peptides or modifications, antibodies or other TLR-5 specific reagents.

Methods of determining TLR5 functional activities in response to an immunomodulatory flagellin peptide or modification thereof include methods described herein, in Examples I through IV, as well as methods known in the art. A variety of methods well known in the art can be used for determining transcription factor activities. For example, fos, jun, and NF-κB activation in response to TLR5 binding to a flagellin molecule can be detected by electrophoretic mobility shift assays well known in the art that detect NF-κB binding to specific polynucleic acid sequences, and promoter-reporter nucleic acid constructs such that, for example, β-lactamase, luciferase, green fluorescent protein or β-galactosidase will be expressed in response to contacting a TLR5 with a flagellin polypeptide, peptide or equivalent thereof. For example, a luciferase reporter plasmid in which luciferase protein expression is driven by one or more NF-κB binding sites can be transfected into a cell, as described in Examples I-IV. Activation of NF-κB results in activation of luciferase reporter expression, resulting in production of luciferase enzyme able to catalyze the generation of a molecule that can be detected by colorimetric, fluorescence, chemiluminescence or radiometric assay.

An amount or activity of a polypeptide, including a cytokine such as TNFα, IL-1 or IL-6, can be a read-out for activation of a TLR5 in response to binding an immunomodulatory flagellin peptide or modification thereof. A variety of methods well known in the art can be used to measure cytokine amounts, such as, for example, flow cytometry methods, immunoassays such as ELISA and RIA, and cytokine RNA protection assays. Commercially available cytokine assay kits, such as ELISA assay formats, can be conveniently used to determine the amount of a variety of cytokines in a sample. Those skilled in the art will determine the particular cytokines to be measured when assessing an immune response in a cell or animal. For example, to determine whether a particular response is characterized as a TH1 or TH2 immune response, those skilled in the art will be able to select appropriate cytokines within the TH1 and TH2 categories, which are well known in the art.

A sample used for determining a TLR5-mediated response or immune response can include, for example, a fluid or tissue obtained from an animal, a cell obtained from an animal fluid or tissue, cultured cells including in vitro and ex vivo cultured cells, and lysates or fractions thereof and cultured cells that express TLR5.

An immune response in an animal is determined by the collective responses of the cells of the immune system. An immune response can be detected by observing various indicators of immune response in an animal. Such indicators include, for example, visible signs of inflammation of tissues, such as swelling, production of antibodies, such as levels of IgA, IgG and IgM in blood and levels of IgA in saliva, alterations in immune cell numbers, such as increased or decreased proliferation of particular immune cells, and in immune cell activities, such as production of immunomodulatory molecules and second messenger molecules. For example, an immune response to a particular antigen can be observed in a animal using methods well known in the art such as delayed hypersensitivity skin tests. An immune response can be determined by the presence of antibodies cross reactive with an antigen, such as by ELISA and Western blotting, lymphocyte activation tests employing mitogen or antigen stimulation, mixed lymphocyte culture tests, assays for human T and B lymphocytes, flow cytometry and cell sorting to characterize populations of immune system cells obtained from an individual, soluble antigen uptake by macrophages, and tests of neutrophil functions (Stites et al. *Basic and Clinical Immunology*, 4th edition, Lange Medical Publications, Los Altos, Calif. (1982)). An immune response can also be assessed by examining amounts or activities of immune system mediators, such as cytokines and chemokines, in cells collected from fluids or tissues of animals. A variety of methods are well known in the art for qualitative and quantitative measurement of cytokine amount and bioassay of cytokine activity.

The methods of the invention for inducing an immune response can be used to treat any animal species having an immune response upon treatment with flagellin polypeptide, peptide, or modification thereof, and for which a stimulation of an immune response is desired. Such animals include avian species such as chicken, and mammalian species such as rodent, canine, feline, bovine, porcine and human subjects. Methods for using adjuvants with vaccines and vaccinating animals are well known in the art and are routinely used in laboratory animals. Those skilled in the art will be able to determine if a particular animal species has a flagellin-stimulated TLR5-mediated innate immune response.

A vaccine to be used in the methods of the invention for inducing an immune response can be administered as a solution or suspension together with a pharmaceutically acceptable medium. Such a pharmaceutically acceptable medium can be, for example, water, phosphate buffered saline, normal saline or other physiologically buffered saline, or other solvent or vehicle such as glycol, glycerol, and oil such as olive oil or an injectable organic ester. A pharmaceutically acceptable medium can also contain liposomes or micelles, and can contain immunostimulating complexes prepared by mixing polypeptide or peptide antigens with detergent and a glycoside, such as Quil A. Further methods for preparing and administering an immunomodulatory flagellin polypeptide or peptide, or modification in a pharmaceutically acceptable medium are presented below, in reference to compounds that induce a TLR-mediated response.

The immunomodulatory flagellin polypeptides, peptides and modifications thereof used in the methods of the invention can be administered by a variety of routes to stimulate an immune response. For example, these immunomodulatory molecules can be delivered intranasally, subcutaneously, intradermally, intralymphatically, intra-muscularly, intratumorally, orally, intravesically, intraperitoneally and intracerebrally. Oral administration is convenient and relatively safe. Oral vaccination protocols can be useful for inducing the state of immunological tolerance which normally occurs in response to most soluble antigens and the proteolytic degradation of antigen preparations in the digestive tract. Nasal delivery routes may be useful for inducing both mucosal and systemic immune responses. A variety of devices are under development for convenient and effective delivery of formulations to the nasal cavity and pulmonary tissues. Those skilled in the art will know how to select appropriate delivery routes for particular formulations of flagellin polypeptides, peptides and modifications thereof.

The invention provides a screening composition consisting of an immunomodulatory flagellin peptide comprising at least about 10 amino acids of substantially the amino acid sequence GAVQNRFNSAIT (SEQ ID NO:2), or a modification thereof, and having toll-like receptor 5 (TLR5) binding, and a TLR5. The composition is useful for identifying agonists, antagonists and ligands for TLR5. The characteristics of an immunomodulatory flagellin peptide comprising at least about 10 amino acids of substantially the amino acid sequence GAVQNRFNSAIT (SEQ ID NO:2), or a modification thereof, and having toll-like receptor 5 (TLR5) binding, and preparation of a flagellin peptide are described herein. Similarly, the characteristics of a TLR5 polypeptide and modifications thereof that have a TLR5 activity, and methods for preparing a TLR5 polypeptide to be used in the methods of the invention are described herein. Chimeric TLR5s, such as the CD4-TLR5 described herein in Example I, are included in the screening compositions of the invention.

The screening composition of the invention includes, for example, cells, cell extracts and artificial signaling systems that contain a TLR5 polypeptide or modification thereof. The cell compositions of the invention include any cell in which TLR5 can couple to a signal transduction pathway to produce a detectable signal in response to an agonist, such as flagellin or a flagellin peptide. Such cells include insect cells such as *Drosophila* cells, yeast cells such as *S. cerevisiae*, prokaryotic cells such as *E. coli*, amphibian cells such as *Xenopus* oocytes, and vertebrate cells such as mammalian primary cells, such as macrophages. Primary cells such as macrophages and other lymphocytes can be conveniently isolated from blood using methods well known in the art. Cells obtained from transgenic animals, such as transgenic mice that have been engineered by known methods of express recombinant TLR5 or TLR5 signal transduction components are also included in the screening compositions of the invention. Cell lines prepared from any of theses cell types, such as S2, CHO, NIH-3T3, 293 and HeLa cells are also included in a screening composition of the invention.

The screening compositions of the invention can include crude or partially purified lysates or extracts of the cell compositions of the invention, and reconstituted signaling systems. Artificial signaling systems include, for example, natural or artificial lipid bilayers, such as a liposome or micelle, which promote an active conformation of a TLR5. The compositions can further contain cellular fractions or isolated components necessary for producing and detecting the desired predetermined signal.

The invention provides a method of screening for a TLR5 ligand, agonist or antagonist. The method involves, (a) contacting a TLR5 with a candidate compound in the presence of a flagellin polypeptide or immunomodulatory flagellin peptide under conditions wherein binding of the flagellin polypeptide or immunomodulatory flagellin peptide to the TLR5 produces a predetermined signal; (b) determining the production of the predetermined signal in the presence of the candidate compound; and (c) comparing the predetermined signal in the presence of the candidate compound with a predetermined signal in the absence of the candidate compound, wherein a difference between the predetermined signals in the presence and absence of the candidate compound indicates that the compound is a TLR5 ligand, agonist or antagonist.

TLR5 can produce a variety of predetermined signals useful in the methods of the invention for identifying a TLR5 ligand, agonist or antagonist. TLR5 has an extracellular domain that participates in ligand recognition and intracellular domain that contain a conserved region called the Toll/IL-1R homology (TIR) domain that, upon activation, recruits an adaptor protein, MyD88. Through an amino terminal death domain, MyD88 recruits the serine kinase IRAK to propagate a pro-inflammatory signal through binding to TRAF6, which then binds to other molecules that participate in the TLR5 signaling cascade. Immunomodulatory flagellin peptides and modifications binding to TLR5 induces signal transduction events which result in, for example, stimulating NF-κB activity and inducing production of gene products of NF-κB-regulated genes, such as TNFα, IL-1 and IL-6, as well as stimulating AP-1 transcription factors fos and jun. Therefore, a predetermined signal can include a signal produced by an immunomodulatory flagellin polypeptide or peptide or modification binding to TLR5, a signal produced by a TLR5 intracellular signal transduction even, such as kinase or phosphatase activity or protein-protein interactions, by activation of fos, jun or NF-κB, and by an amount or activity of a fos-, jun- or NF-κB-regulated gene or gene product, such as TNFα, IL-1 and IL-6.

A variety of low- and high-throughput assays suitable for detecting selective binding interactions between a receptor and a ligand are known in the art. Both direct and competitive assays can be performed, including, for example, fluorescence correlation spectroscopy (FCS) and scintillation proximity assays (SAP) reviewed in Major, *J. Receptor and Signal Transduction Res.* 15:595-607 (1995); and in Sterrer et al., *J. Receptor and Signal Transduction Res.* 17:511-520 (1997)). Other assays for detecting binding interactions include, for example, ELISA assays, FACS analysis, and affinity separation methods. Such assays can involve labeling a TLR5 ligand, such as flagellin or a flagellin peptide, with a detectable moiety such as a radiolabel, fluorochrome, ferromagnetic substance, or luminescent substance. A detectably labeled flagellin polypeptide or peptide can be prepared using methods well known in the art. Receptor binding assays, including high-throughput automated binding assays, and methods of determining binding affinity from such assays, are well known in the art, and any suitable direct or competitive binding assay can be used. Exemplary high-throughput receptor binding assays are described, for example, in Mellentin-Micelotti et al., *Anal. Biochem.* 272:P 182-190 (1999); Zuck et al., *Proc. Natl. Acad. Sci. USA* 96:11122-11127 (1999); and Zhang et al., *Anal. Biochem.* 268; 134-142 (1999).

A variety of methods well known in the art can be used to detect activation of transcription factors, such as NF-κB, in low- or high-throughput formats. The methods described herein and in the Examples can be adapted to formats suitable for candidate compound screening.

A variety of low- and high-throughput assays suitable for detecting amounts and activities of polypeptides such as cytokines are known in the art. Methods for detecting polypeptides, include, for example, flow cytometric measurements as described herein, immunodetection methods such as radioimmune assay (RIA), ELISA, immunoprecipitation and Western blotting. Assay of the activity of a cytokine include function bioassays and detection of amounts of polypeptides regulated by a particular cytokine. Those skilled in the art can determine an appropriate method for detecting an activity of a particular cytokine.

Suitable conditions under which TLR5 produces a predetermined signal in response to a flagellin polypeptide, peptide or modification can be determined by those skilled in the art, and will depend on the particular predetermined signal selected. Exemplary conditions for determining the production of a predetermined signal are provided herein in Examples I-IV. Any known or predicted TLR5-mediated cellular event, such as elicitation of second messengers, induction of gene expression or altered cellular proliferation, differentiation or viability can be a predetermined signal that is an indication of activation of signal transduction through TLR5.

Assays for detecting a predetermined signal produced by binding of flagellin or flagellin peptide to TLR5 can be performed, for example, with whole cells that express TLR5, membrane fractions, or artificial systems, as described herein, or with isolated TLR5 polypeptide, either in solution, in an artificial membrane, or bound to a solid support.

A method of identifying TLR5 agonists and antagonists can be performed either in the presence of a predetermined concentration of a known TLR5 agonist, such as flagellin, flagellin peptide, or modifications thereof, or in the absence of agonist. The agonist can be added either prior to, simultaneously with, or after, addition of the test compound. When present, the agonist concentration is preferably within 10-fold of its EC50 under the assay conditions to allow the identification of a compound that competes with a known agonist for signaling through TLR5, or indirectly augments signaling through the receptor. Likewise, a compound that reduces binding between a known agonist and its receptor, or indirectly decreases signaling through the receptor, can also be identified.

The method of screening to identify a ligand, agonist or antagonist of TLR5 involve testing a candidate compound. A candidate compound can be any substance, molecule, compound, mixture of molecules or compounds, or any other composition. The candidate compounds can be small molecules or macromolecules, such as biological polymers, including proteins, polysaccharides and nucleic acids. Sources of candidate compounds which can be screened for a ligand, agonist or antagonist of TLR5 include, for example, libraries of small molecules, peptides and polypeptides.

Additionally, candidate compounds can be preselected based on a variety of criteria. For example, suitable candidate compounds can be selected as having known ligand, agonist or antagonist activity. Alternatively, candidate compounds can be selected randomly. Candidate compounds can be administered to the reaction system at a single concentration or, alternatively, at a range of concentrations to determine, for example, an EC50 or IC50 of a candidate compound.

The method of screening for TLR5 ligands, agonists or antagonists can involve groups or libraries of compounds. Methods for preparing large libraries of compounds, including simple or complex organic molecules, carbohydrates, peptides, peptidomimetics, polypeptides, nucleic acids, antibodies, and the like, are well known in the art. Libraries containing large numbers of natural and synthetic compounds can be obtained from commercial sources.

The number of different candidate compounds to examine using the methods of the invention will depend on the application of the method. It is generally understood that the larger the number of candidate compounds, the greater the likelihood of identifying a compound having the desired activity in a screening assay. Large numbers of compounds can be processed in a high-throughput automated format.

The TLR5 agonists, antagonists and ligands identified using the methods and compositions described herein, are potential therapeutic compounds that can be administered to an individual, such as a human or other mammal, in an effective amount to increase or decrease signaling through TLR5, for example, to alter an immune response or treat a TLR5-associated condition. Such compounds can be used analogously to immunomodulatory compounds useful for augmenting and altering an immune response, as described above. For example, a compound can be used to induce a general immune response and to induce a specific immune response in the presence of an antigen and to alter the level of a particular cytokine in an individual having a pathological condition.

The TLR5 agonists and antagonists, immunomodulatory flagellin peptides, polypeptides and modifications thereof, are useful for ameliorating, or reducing the severity of a pathological condition. Reduction in severity includes, for example, an arrest or decrease in clinical symptoms, physiological indicators, biochemical markers or metabolic indicators of disease. Those skilled in the art will know, or will be able to determine the appropriate clinical symptoms, physiological indicators, biochemical markers or metabolic indicators to observe for a particular pathological condition. To prevent a disease means to preclude the occurrence of a disease or restoring a diseased individual to their state of health prior to disease.

In addition to applications described herein for agonists and antagonists, a TLR5 ligand can be used, for example, to specifically target a diagnostic moiety to cells and tissues that express TLR5, such as monocytes, immature dendritic cells, epithelial cells, and other cells involved in an immune response. Thus, a TLR5 ligand can be labeled with a detectable moiety, such as a radiolabel, fluorochrome, ferromagnetic substance, or luminescent substance, and used to detect normal or abnormal expression of TLR5 polypeptide in an isolated sample or in vivo diagnostic imaging procedures.

A heterologous amino acid sequence can be advantageously used to provide a tag for detection or purification or to impart an activity to a reference polypeptide or peptide, such as an enzyme activity, a biological activity, an immunological activity or stability. An immunomodulatory flagellin peptide, polypeptide or modification thereof, or TLR5 polypeptide can contain a heterologous amino acid sequence, or amino acid sequence not present in the native amino acid sequence of a reference polypeptide or peptide and not represented by a modification of a reference polypeptide or peptide. A heterologous amino acid sequence can be of any size in relation to the reference amino acid sequence. A TLR5 polypeptide containing the heterologous sequence of CD4 is a specific example of such a modification and is described further in Example I. The described CD4-TLR5 chimera is identified by the amino acid sequence of SEQ ID NO:10, encoded by the nucleic acid sequence of SEQ ID NO:9. A chimeric TLR5 can be prepared using cloning methods well known in the art. For example, a chimeric polypeptide can be produced by amplifying by PCR a nucleotide sequence encoding a portion of a selected polypeptide using sequence specific primers. Primers useful for amplifying a TLR5 include, for example, huTLR5-A6: TTAAAGTGGTAC-CAGTTCTCCCTTTTCATTGT ATGCACT (SEQ ID NO:35) and huTLR5DNS: CGGGATCCCGTTAGGAG ATGGTTGCTACAGTTTGC (SEQ ID NO:36). A portion of a TLR5 nucleotide sequence, such as a sequence amplified using such primers can be fused to a nucleotide sequence encoding a heterologous amino acid sequence. A variety of methods for generating nucleic acid sequences encoding chimeric polypeptides are well known to those skilled in the art.

The polypeptides and peptides described herein, including immunomodulatory flagellin peptides, flagellin polypeptide, TLR5 polypeptides and fragments thereof can be prepared using a variety of protein expression systems well known in the art, including prokaryotic and eukaryotic expression systems. Prokaryotic expression systems are advantageous due to their ease in manipulation, low complexity growth media, low cost of growth media, rapid growth rates and relatively high yields. Well known prokaryotic expression systems include, for example, *E. coli* bacterial expression systems based on bacteriophage T7 RNA polymerase, the trc promoter, the araB promoter and *bacillus* expression. Eukaryotic expression systems are advantageous because expressed polypeptides can contain eukaryotic post-translational modifications such as O-linked glycosylation, phosphorylation and acetylation and can have improved protein folding. Well known eukaryotic expression systems include, for example, expression in yeast, such as *Pichia pastoris* and *Pichia methanolica*, expression in insect systems such as the *Drosophila* S2 system and baculovirus expression systems and expression in mammalian cells using adenoviral vectors and cytomegalovirus promoter-containing vectors.

An immunomodulatory flagellin peptide, polypeptide, TLR5 or fragments thereof can be purified using a variety of methods of protein purification well known in the art. Biochemical purification can include, for example, steps such as solubilization of the polypeptide or peptide-expressing cell, isolation of the desired subcellular fractions, chromatography, such as ion exchange, size, or affinity-based chromatographies, electrophoresis, and immunoaffinity procedures. Other well-known methods are described in Deutscher et al., *Guide to Protein Purification: Methods in Enzymology* Vol. 182, (Academic Press, (1990)). An exemplary method for purifying a flagellin peptide is provided in Example III. The methods and conditions for biochemical purification of a polypeptide of the invention can be chosen by those skilled in the art, and the purification monitored, for example, by staining SDS-PAGE gels containing protein samples, by immunodetection methods such as Western blotting and ELISA, and by functional assay of immunogenic activity of flagellin or a TLR5 activity of TLR5.

An immunomodulatory flagellin peptide, polypeptide, TLR5 or fragments thereof can be modified, for example, to increase polypeptide stability, alter an activity, facilitate detection or purification, or render the enzyme better suited for a particular application, such as by altering substrate specificity. Computer programs known in the art can be used to determine which amino acid residues of a immunomodulatory flagellin peptide, flagellin polypeptide or TLR5 can be modified as described above without abolishing a corresponding activity (see, for example, Eroshkin et al., *Comput. Appl. Biosci.* 9:491-497 (1993)). In addition, structural and sequence information can be used to determine the amino acid residues important for activity. For example, a comparisons of flagellin amino acid sequences, such as that shown in FIG. 7 can provide guidance in determining amino acid residues that can be altered without abolishing flagellin or flagellin peptide activity by indicating amino acid residues that are conserved across species. Conserved regions of flagellin are well known in the art and have been described, for example, in Mimori-Kiyosue, et al., *J. Mol. Viol.* 270:222-237, (1997). A crystal structure of flagellin can also provide guidance for making flagellin modifications (Samatey et al. *Nature,* 410: 331-337 (2001)). Similarly, amino acid sequence comparisons between the disclosed murine TLR5, TLR5s of other species, and other toll-like receptor family members can provide guidance for determining amino acid residues important for activity.

An isolated TLR5 is a TLR5 removed from one or more components with which it is naturally associated. Therefore, an isolated TLR5 can be a cell lysate, cell fraction, such as a membrane fraction, or a purified TLR5 polypeptide. An isolated TLR5 can include a liposome or other compound or matrix that stabilizes or promotes an active conformation of the receptor.

For treating or reducing the severity of a pathological condition a TLR5 agonist or antagonist, immunomodulatory flagellin peptide, polypeptide or modification thereof, including a vaccine, can be formulated and administered in a manner and in an amount appropriate for the condition to be treated; the weight, gender, age and health of the individual; the biochemical nature, bioactivity, bioavailability and side effects of the particular compound; and in a manner compatible with concurrent treatment regimens. An appropriate amount and formulation for a particular therapeutic application in humans can be extrapolated based on the activity of the compound in recognized animal models of the particular disorder.

Animal models of aberrantly proliferative diseases can be used to assess a formulation of compound, including a vaccine or adjuvant containing an immunomodulatory flagellin peptide, polypeptide or modification thereof, for an amount sufficient to induce an immune response or ameliorate disease symptoms. Animal models of such pathological conditions well known in the art which are reliable predictors of treatments in human individuals for include, for example, animal models for tumor growth and metastasis, infectious diseases and autoimmune disease.

There are numerous animal tumor models predictive of therapeutic treatment which are well known in the art. These models generally include the inoculation or implantation of a laboratory animal with heterologous tumor cells followed by simultaneous or subsequent administration of a therapeutic treatment. The efficacy of the treatment is determined by measuring the extent of tumor growth or metastasis. Measurement of clinical or physiological indicators can alternatively or additionally be assessed as an indicator of treatment efficacy. Exemplary animal tumor models can be found described in, for example, Brugge et al., *Origins of Human Cancer*, Cold Spring Harbor Laboratory Press, Plain View, N.Y., (1991).

Similarly, animal models predictive for infectious disease also follow a similar approach. Briefly, laboratory animals are inoculated with an infectious agent and the progression of the infection is monitored by, for example, clinical symptoms, growth culture of the agent from an infected tissue sample or biopsy in the presence or absence of the therapeutic treatment. The reduction in severity of the diagnostic indicator is indicative of the efficacy of the treatment. A variety of animal models for infectious diseases are well known to those skilled in the art.

One animal model predictive for autoimmune diseases is Experimental allergic encephalomyelitis (EAE), also called experimental autoimmune encephalomyelitis. Although originally characterized as a model for neurological autoimmune disease such as human multiple sclerosis, the use of this model to predict treatments of other autoimmune diseases has been widely accepted. EAE is induced in susceptible animals by active immunization with myelin basic protein (MPB) or by passive transfer of MBP-specific T helper lymphocytes. Progression of the disease is characterized by chronic relapsing paralysis and central nervous system demyelination, which can be monitored by observation or by immunological determinants such as delayed-type hypersensitivity (DTH; a measure of cell mediated immunity) response to the immunogen. Efficacy of a therapeutic treatment is compared to progression of the disease in the absence of treatment. A reduction in severity of EAE symptoms or immunological determinants in treated animals is indicative of the efficacy of the therapeutic treatment. For a review of autoimmune disease models see, for example, Urban et al., *Cell*, 54:577-592 (1988); Brostoff et al., *Immunol. Ser.* 59:203-218 (1993) and U.S. Pat. Nos. 5,614,192 and 5,612,035.

A growing number of human diseases have been classified as autoimmune and include, for example, rheumatoid arthritis, myasthenia gravis, multiple sclerosis, psoriasis, systemic lupus erythematosis, autoimmune thyroiditis, Graves' disease, inflammatory bowel disease, autoimmune uveoretinitis, polymyositis and diabetes. Animal models for many of these have been developed and can be employed analogously as the EAE model described above predictive assessment of therapeutic treatments using the compounds, vaccines and adjuvants in the methods of the invention.

Other reliable and predictive animal models are well known in the art and similarly can be used to assess a compound formulation, including vaccine and adjuvant formulations containing an immunomodulatory flagellin peptide, polypeptide or modification thereof.

The total amount of a compound including an immunomodulatory flagellin peptide, polypeptide or modification thereof, that modulates a TLR5-mediated immune response can be administered as a single dose or by infusion over a relatively short period of time, or can be administered in multiple doses administered over a more prolonged period of time. Additionally, a compound can be administered in a slow-release matrix, which can be implanted for systemic delivery at or near the site of the target tissue.

A compound that modulates a TLR5-mediated immune response can be administered to an individual using a variety of methods known in the art including, for example, intravenously, intramuscularly, subcutaneously, intraorbitally, intracapsularly, intraperitoneally, intracisternally, intra-articularly, intracerebrally, orally, intravaginally, rectally, topically, intranasally, or transdermally.

A compound that modulates a TLR5-mediated immune response can be administered to a subject as a pharmaceutical composition comprising the compound and a pharmaceutically acceptable carrier. The choice of pharmaceutically acceptable carrier depends on the route of administration of the compound and on its particular physical and chemical characteristics. Pharmaceutically acceptable carriers are well known in the art and include sterile aqueous solvents such as physiologically buffered saline, and other solvents or vehicles such as glycols, glycerol, oils such as olive oil and injectable organic esters. A pharmaceutically acceptable carrier can further contain physiologically acceptable compounds that stabilize the compound, increase its solubility, or increase its absorption. Such physiologically acceptable compounds include carbohydrates such as glucose, sucrose or dextrans; antioxidants, such as ascorbic acid or glutathione; chelating agents; and low molecular weight proteins. As described above in reference to vaccines, such routes of administration are also applicable to administration of an immunomodulatory flagellin peptide, polypeptide or modification thereof.

In addition, a formulation of a compound that modulates a TLR5-mediated immune response can be incorporated into biodegradable polymers allowing for sustained release of the compound, the polymers being implanted in the vicinity of where drug delivery is desired, for example, at the site of a tumor or implanted so that the compound is released systemically over time. Osmotic minipumps also can be used to provide controlled delivery of specific concentrations of a compound through cannulae to the site of interest, such as directly into a tumor growth or other site of a pathology involving a perturbation state. The biodegradable polymers and their use are described, for example, in detail in Brem et al., *J. Neurosurg.* 74:441-446 (1991). These methods, in addition to those described above in reference to vaccines, are applicable to administering an immunomodulatory flagellin peptide, polypeptide or modification thereof to induce an immune response.

The methods of treating a pathological condition additionally can be practiced in conjunction with other therapies. For example, for treating cancer, the methods of the invention can be practiced prior to, during, or subsequent to conventional cancer treatments such as surgery, chemotherapy, including administration of cytokines and growth factors, radiation or other methods known in the art. Similarly, for treating pathological conditions which include infectious disease, the methods of the invention can be practiced prior to, during, or subsequent to conventional treatments, such as antibiotic administration, against infectious agents or other methods known in the art. Treatment of pathological conditions of autoimmune disorders also can be accomplished by combining the methods of the invention for inducing an immune response with conventional treatments for the particular autoimmune diseases. Conventional treatments include, for example, chemotherapy, steroid therapy, insulin and other growth factor and cytokine therapy, passive immunity and inhibitors of T cell receptor binding. The methods of the invention can be administered in conjunction with these or other methods known in the art and at various times prior, during or subsequent to initiation of conventional treatments. For a description of treatments for pathological conditions characterized by aberrant cell growth see, for example, *The Merck Manual*, Sixteenth Ed, (Berkow, R., Editor) Rahway, N.J., 1992.

As described above, administration of a compound, immunomodulatory flagellin peptide, flagellin polypeptide or modification thereof can be, for example, simultaneous with or delivered in alternative administrations with the conventional therapy, including multiple administrations. Simultaneous administration can be, for example, together in the same formulation or in different formulations delivered at about the same time or immediately in sequence. Alternating administrations can be, for example, delivering an immunomodulatory flagellin peptide or polypeptide formulation and a conventional therapeutic treatment in temporally separate administrations. As described previously, the temporally separate administrations of a compound, immunomodulatory flagellin peptide, polypeptide or modification thereof, and conventional therapy can similarly use different modes of delivery and routes.

The invention provides a method of using a signal produced in response to flagellin binding to TLR5 to detect bacterial contamination in a sample. The method can be used to detect picogram amounts of flagellin in a sample.

Food-born diseases resulting from the presence of harmful bacteria account for 325,000 hospitalizations and 5,000 deaths each year in the United States (National Institutes of Health, Foodborne Diseases NIAID Fact Sheet). The U.S. Centers for Disease Control and Prevention (CDC) estimates that 1.4 million people in the United States are infected each year with *Salmonella*. Other bacterial pathogens that cause pathological conditions characterized by symptoms ranging from intestinal discomfort to severe dehydration, bloody diarrhea and even death, include enterohemorrhagic *E. coli*, such as strains designated O157:H7 and O26:H11, *Campylobacter* strains such as *C. jejuni*, and *Shigella* strains such as *S. flexneri*.

All of these bacterial strains are flagellated, and therefore express flagellin polypeptides. For example, the amino acid sequences of flagellins from *Salmonella, E. coli, Campylobacter, Shigella* strains are shown in FIG. 7. The methods of the invention for detecting flagellin polypeptides contained in samples suspected of bacterial contamination can be applied to quality assurance protocols for preparation of foods and numerous other applications.

The invention also provides a bioassay for detecting bacterial contamination in a sample. The method involves, (a) contacting the sample with a TLR5 under conditions wherein binding of a flagellin polypeptide or fragment thereof in the sample to the TLR5 produces a predetermined signal, (b) determining the production of the predetermined signal in the presence and absence of the sample, and (c) comparing the predetermined signal in the presence of the sample with a predetermined signal in the absence of the sample, wherein a difference between the predetermined signals in the presence and absence of the sample indicates that the sample contains flagellin.

The methods of the invention for detecting bacterial contamination are based on the finding disclosed herein that flagellin is a ligand for TLR5. Therefore, a flagellin molecule in a sample can bind to a TLR5 and elicit the production of a predetermined signal. A predetermined signal produced by TLR5 in a particular assay system is compared in the presence and absence of a sample known or suspected of containing a bacterial contaminant. A sample known to be free of flagellin can be used as a negative control, while a sample containing a known concentration of flagellin, flagella or bacteria having flagella can be used as a positive control.

A sample to be tested for the presence of flagellin can be any material that is suspected of being contaminated with a gram-positive or gram-negative flagellated bacterium. For example, the method for determining the presence of flagellin can be performed using a sample of a biological fluid, cell, tissue, organ or portion thereof, such as a sample of a tissue to be used for preparing a product, a product for human or animal consumption, such as a food or pharmaceutical preparation, and a product for external application or administration by any route to an animal.

A variety of predetermined signals produced by a TLR5, as discussed above and in the Examples herein, can be used to detect the binding and activation of a TLR5 by a flagellin molecule present in a sample. A variety of methods known in the art, including those described herein can be used to detect a predetermined signal produced by a TLR5.

It is understood that modifications which do not substantially affect the activity of the various embodiments of this invention are also included within the definition of the invention provided herein. Accordingly, the following examples are intended to illustrate but not limit the present invention.

EXAMPLE I

Constitutively Active TLR5 Activates NF-κB and TNFα Production

This example shows activation of NF-κB and TNFα production in CHO cells in response to constitutively active TLR5.

To determine if TLR5 activates NF-κB and TNFα production, the activity of a constitutively active form of TLR5 was examined in CHO cells. Constitutively active forms of TLR4 and TLR5 were generated by fusing the extracellular domain of CD4 to the transmembrane and TIR domain of TLR4 or TLR5 (Medzihitov, R. et al. *Nature* 388, 394-7 (1997); Ozinsky, A. et al., *Proc. Natl. Acad. Sci.* 97, 13766-13881 (2000)). CD4-TLR5 was constructed by fusing the murine CD4 extracellular domain (amino acids 1-391) to the putative transmembrane and cytoplasmic domains of human TLR5 (amino acids 639-859) and cloning into pEF6-TOPO (pEF6-mCD4-hTLR5). These chimeras, referred to as CD4-TLR4 and CD4-TLR5 were expressed in CHO cells.

For determining NF-κB activity in response to TLR5, CHO cells were transiently transfected with expression vectors for CD4-TLR4, CD4-TLR5, or empty expression vector (control) together with an NF-κB luciferase reporter. NF-κB-induced luciferase activity was measured. CHO cells (CHO-K1) were obtained from ATCC (no. CRL.-9618) and grown in Ham's F-12 medium supplemented with 10% FBS, L-glutamine, penicillin, and streptomycin. CHO cells were transfected by electroporation as described previously (Underhill, D. M. et al., *Nature*, 401, 811-5 (1999)), with 1 μg of the indicated TLR expression vector, 1 μg of ELAM-firefly luciferase, 0.1 μg of TK-renilla luciferase (Promega). Cells were plated on 96-well plates at 100,000 cells/well, and incubated overnight at 37° C., 5% $CO_2$. Firefly and renilla luciferase activities were measured using the Dual Luciferase Assay System (Promega, Madison, Wis.). Luciferase activity is expressed as a ratio of NF-κB-dependent ELAM-firefly luciferase activity divided by control thymidine kinase-renilla luciferase activity (relative luciferase units).

For determining TNFα production in response to TLR5, RAW-TTIO Macrophage cells were transfected with a CD4-TLR5 expression vector, and the production of TNFα was measured by flow cytometry, as described previously (Ozinsky, A. et al. *Proc. Natl. Acad. Sci.* 97, 13766-13771 (2000)). Transfections were performed by electroporation using 10 μg of pEF6-mCD4-hTLR5, and 18 hours later the cells were incubated with 5 μg/ml of brefeldin A for 4 hours to accumulate intracellular pools of newly synthesized TNFα. Cells were fixed, permeabilized, stained for the expression of CD4 (anti-CD4-FITC, Pharmingen) and TNFα (anti-murine TNFα-PE, Pharmingen), and analyzed on a FACscan (Beckton-Dickenson). FACS data were analyzed with WinMDI (Joseph Trotter, Scripps Research Institute, La Jolla, Calif.). Cells were gated to exclude dead cells and for expression of CD4.

Figure 1B:
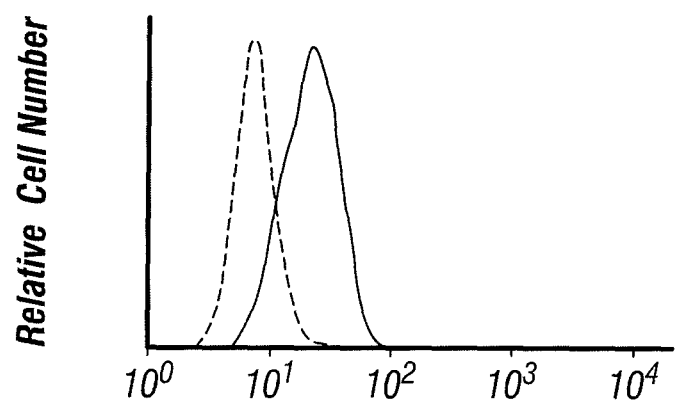

FIG. 1 shows that expression of CD4-TLR5 induced NF-κB activation-mediated luciferase production in CHO cells (FIG. 1a) and TNFα production in mouse macrophages (FIG. 1b). In FIG. 1b, the dotted line indicates TNFα produced in cells not expressing CD4-TLR5, and the solid line indicates TNFα produced in cells expressing CD4-TLR5.

Thus, homo-oligomerization of the TLR5 signaling domain induces a cellular signal characterized by the induction of NF-κB activity and production of TNFα.

EXAMPLE II

Bacterial Culture Supernatants Contain TLR5-Stimulating Activity

This Example shows that bacterial culture supernatants contain TLR5-stimulating activity.

CHO cells expressing human TLR5 and a luciferase-linked reporter were used to screen for PAMPs recognized by the receptor. PAMPS tested included LPS, lipopeptide, yeast, and extracts from *E. coli, Pseudomonas*, and *Listeria*. CHO cells were transiently transfected with TLR2, TLR5, or empty expression vectors together with a NF-κB luciferase reporter. The cells were treated with 100 ng/ml LPS, 100 ng/ml lipopeptide, $10^7$ yeast particles/ml, or untreated (control), and luciferase activity was measured. The cells were treated with 67 μg/ml of supernatant from the indicated saturated bacterial cultures, or LB alone (control), and the luciferase activity was measured. Data are representative of 3 independent experiments.

Human TLR5 and TLR2 were generated by PCR from cDNA derived from human peripheral blood mononuclear cells and cloned into pEF6-TOPO (Invitrogen) (pEF6-hTLR5 and pEF6-hTLR2). Murine TLR5 was generated by PCR using cDNA derived from RAW-TTlO cells and cloned into pEF6 (pEF6-mTLR5).

For luciferase assays, CHO cells were transfected by electroporation as described above, with 1 μg of the indicated TLR expression vector, 1 μg of ELAM-firefly luciferase, 0.1 μg of TK-renilla luciferase (Promega, Madison, Wis.). The medium was replaced with medium containing the stimuli at the indicated concentration/dilution. Bacterial lipopeptide and $PAM_3CSK_4$, were obtained from Roche, LPS (*Salmonella minnesota* R595) was from List, and yeast particles (zymosan) were from Molecular Probes (Eugene, Oreg.). Cells were stimulated for 5 hours at 37° C., and firefly and renilla luciferase activities were measured using the Dual Luciferase Assay System (Promega).

For preparation of bacterial supernatants, bacteria were grown either in Luria broth (LB) (*Escherichia coli* TOP 10 (Invitrogen), *Salmonella minnesota* (ATCC#49284), mutant *Salmonella typhimurium* (TH4778 fliB– fliC+), TH2795 (fliB– fliC–), (Dr. Kelly Hughes, University of Washington), or grown in trypticase soy broth (TSB) (*Listeria monocytogenes* (10403, gift of Dr. Daniel Portnoy, UCSF), *Listeria innocua* (ATCC#33090), *Bacillus subtilis*, and *Pseudomonas aeruginosa* (Susan R. Swanzy, University of Washington)). Bacteria were grown to saturation (about 16 hours, 37° C. with vigorous aeration). The bacterial culture supernatants were centrifuged for 30 minutes at 2000×g, filtered. (0.2 μM), and stored at 4° C. prior to use. For flaA transfections, *E. coli* TOP10 containing pTrcHis2-flaA or pTrcHis2-flaArev were selected from bacterial plates and grown to $OD_{600}$ of 0.6 in LB with 100 μg/ml ampicillin and 1% w/v glucose. The bacteria were centrifuged for 30 minutes at 2000×g, and split into two LB cultures, one containing 100 μg/ml ampicillin and 1% w/v glucose (to repress flaA) and the other containing 100 μg/ml ampicillin and 1 mM IPTG (to induce flaA). Samples were taken at 4 hours after induction, centrifuged 5 min at 10,000×g, and the supernatants stored at 4° C. before use.

Figure 2A:
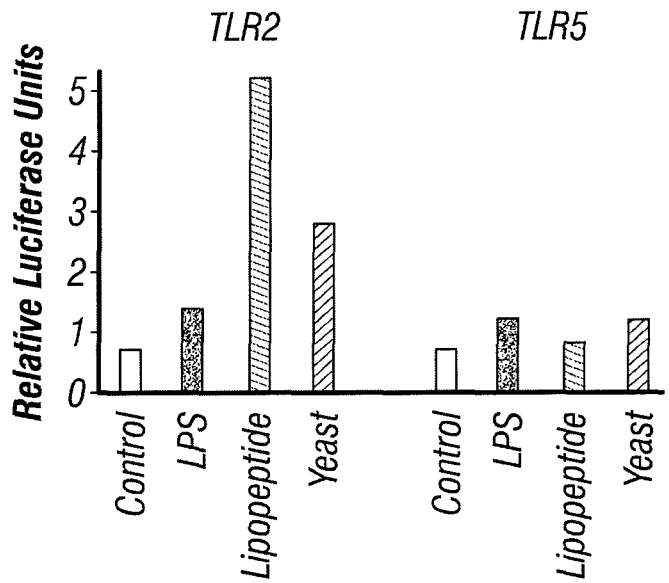
FIGS. 2A-B show selective induction of TLR5-stimulated activation of NF-kB by *P. aeruginosa* and *L. monocytogenes* cultures compared to LPS and lipopeptide.
Figure 2B:
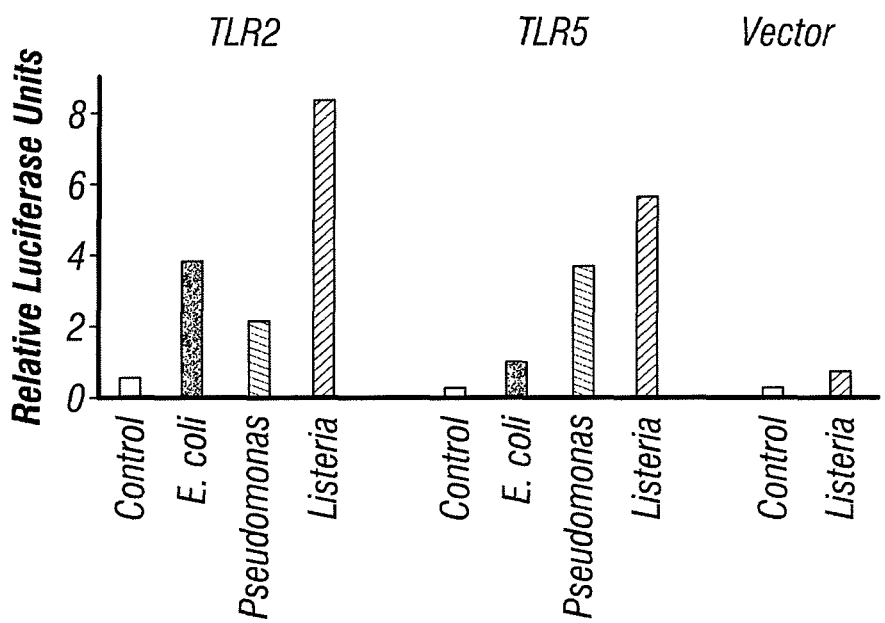

TLR5 did not respond to any of the PAMPs known to stimulate TLR pathways, such as LPS, lipopeptide, yeast cell wall, or peptidoglycan, while CHO cells transfected with TLR2 were stimulated by lipopeptide, yeast cell wall, and peptidoglycan (FIG. 2a). However, TLR5-stimulating activity was detected in culture supernatants of a variety of Gram-positive and Gram-negative bacteria (FIG. 2b). The TLR5-stimulating activity of Gram-positive bacteria was not enhanced by co-expression of CD14. Interestingly, the TOP10 strain of *E. coli* had very little TLR5 activity (FIG. 2b), and was used in subsequent reconstitution experiments (see below). Experiments using murine TLR5 yielded similar results.

Thus, the activity of TLR5 was stimulated by a component of bacterial culture supernatants, but not by PAMPs known to stimulate other toll like receptor family members.

EXAMPLE III

Purification of TLR5-Stimulating Activity from *L. monocytogenes* Culture Supernatant This Example shows the purification of TLR5-simulating activity from *L. monocytogenes* culture supernatant.

The biological activity recognized by TLR5 was determined to be TCA precipitable, phenol soluble, and sensitive to proteinase K and trypsin digestion. To identify the bacterial components that stimulate TLR5, the supernatant from a saturated *L. monocytogenes* culture was concentrated, fractionated by reverse-phase chromatography, and each fraction was assessed for TLR5-stimulating activity in CHO cells (FIG. 3a).

For assessing the TLR-stimulating activity of FPLC fractions, CHO cells were transfected as described in Example I with the addition of 0.1 μg of pNeo/Tak (Underhill et al., Nature 401, 811-5 (1999)), and stable populations of cells expressing the indicated TLR with the luciferase reporters were selected in 100 μg/ml G418. These cells were plated on 96-well plates at 100,000 cells/well and incubated overnight.

For the purification of the TLR5-stimulating activity, saturated *L. monocytogenes* culture (200 ml of TSB) was centrifuged, and the supernatant was enriched for molecules larger than 30 kDa by ultrafiltration (Ultrafree-15 filter unit with Biomax-30 membrane, Millipore). The buffer was changed to 100 mM Tris pH 7.5, and the volume was adjusted to 5 ml. The sample was loaded onto a HR5/10 reverse-phase chromatography column (AP Biotech) and run at 0.3 ml/min. Reverse-phase chromatography was performed with the indicated elution profile using the following buffers: (A) initial buffer, 0.1% TFA in water, (B) final buffer, 0.1% TFA in acetonitrile. Fractions were collected at 3-minute intervals. FPLC fractions (50 μl) were separated on a 10% SDS-PAGE gel.

Figure 3A:
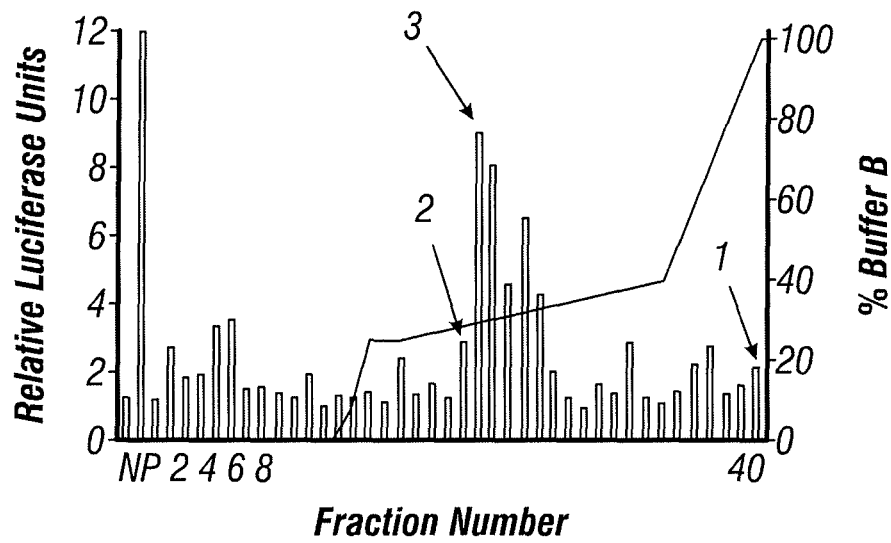
FIGS. 3A-C show the purification of a TRL5-stimulating activity from *L. monocytogenes* culture supernatant.
Figure 3B:
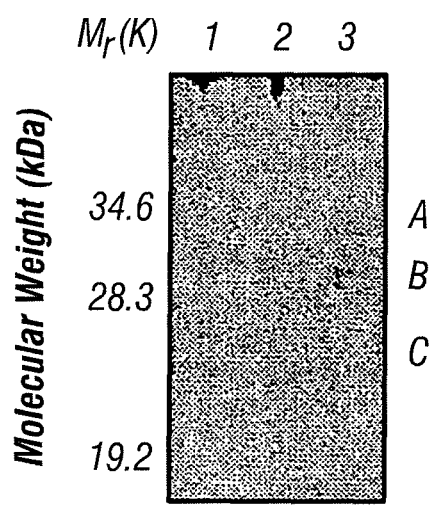
Figure 3C:
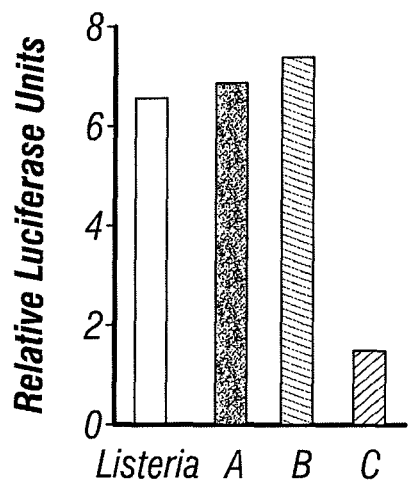
Figures 4A, 4B:
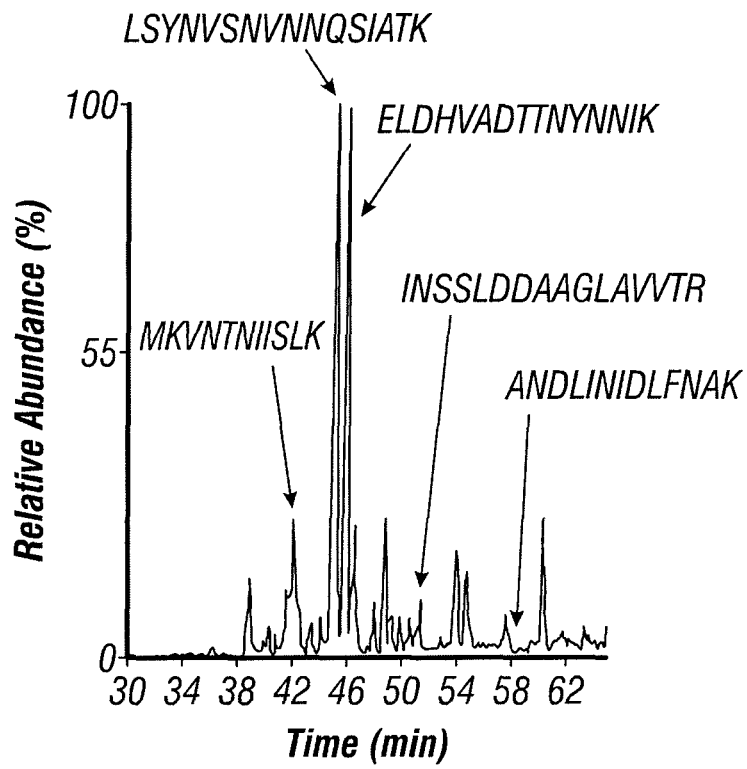
FIGS. 4A-C (portions of SEQ ID NO:32 (including amino acids 1-11, amino acids 36-51, amino acids 120-134, amino acids 155-168, amino acids 224-240) and SEQ ID NO:32) show the identification by mass spectrometry of flagellin as a TLR5-stimulating activity.

As shown in FIG. 3a, CHO cells expressing an NF-κB luciferase reporter and TLR5 were stimulated with reverse-phase FPLC fractions, and TLR5-mediated NF-κB luciferase activity was measured. The fraction numbers correspond to 3 minute fractions of reverse-phase FPLC eluted with a non-linear gradient of buffer B as shown. Fraction number "N" is control LB growth medium and "P" is the *L. monocytogenes* culture supernatant prior to chromatography. Fractions containing background activity (1), low activity (2) and high activity (3) as indicated in FIG. 3a were analyzed by SDS-PAGE and silver stain. Silver staining was performed according to established methods. Two bands with apparent molecular masses of 30-34 kDa were clearly enriched in the fraction containing the highest level of TLR5-stimulating activity (FIG. 3b, Lane 3). Proteins eluted from regions A, B, and C of the SDS-PAGE gel, as indicated in FIG. 3b were assayed for TLR5-mediated NF-κB activation in CHO cells. In FIG. 3c, "*Listeria*" indicates *L. monocytogenes* culture supernatant. One of these bands, (FIG. 3b, band A), was trypsin-treated, subject to microcapillary HPLC-tandem mass spectrometry, and identified by comparison of peptide tandem mass spectra to sequences in a non redundant protein database using the computer program, SEQUEST27 (FIG. 4a). TLR5-stimulating activity was not recovered from any other section of the gel.

Thus, a TLR5-stimulating activity was purified from culture supernatants from *L. monocytogenes*.

EXAMPLE IV

Flagellin is a TLR5 Stimulus

This example shows that flagellin is a TLR5 stimulus purified from culture supernatants from *L. monocytogenes*.

As described above, a TLR5-stimulating activity was purified from *L. monocytogenes* culture supernatants using HPLC. The isolated polypeptide of band A in FIG. 3b was trypsinized and identified by microcapillary HPLC-tandem mass spectrometry. Peaks corresponding to *L. monocytogenes* flagellin peptides are indicated in FIG. 4a. Five sequences were identified (FIG. 4a) that correspond to flagellin, the product of the flaA gene of *L. monocytogenes* (Genbank Q02551). The location of these sequences within the protein is indicated in FIG. 4b. Band B of FIG. 3b also is flagellin, which migrates as a doublet of approximately 30 kDa on SDS-PAGE (FIG. 3b).

For analysis, bands A and B were excised from SDS-PAGE gels, dehydrated with acetonitrile, dried under reduced vacuum, and trypsin (12.5 ng/μL) was infused into the gel. The gel slice was allowed to incubate on ice for 45 min in the presence of trypsin and then excess trypsin removed and replaced with 50 mM ammonium bicarbonate and the gel slice incubated overnight at 37° C. Peptides were extracted by 3 washes with 5% acetic acid in 50% aqueous acetonitrile. The extractions were pooled and concentrated by vacuum centrifugation. The peptides were injected onto a C18 peptide trap cartridge (Michrom BioResources, Inc. Auburn, Calif.), desalted, and then injected onto a 75 μm (internal diameter)× 10 cm micro-capillary HPLC column (Magic C18; 5-μm packing; 100 A pore size; Michrom BioResources, Inc. Auburn, Calif.). The sample injection was made using a FAMOS autosampler (LCPackings, San Francisco, Calif.) coupled with an Agilent HP1100 Pump. Peptides were separated by a linear gradient of acetonitrile, and subjected to collision induced dissociation using an electrospray ionization-ion trap mass spectrometer (ESI-ITMS; ThermoQuest, San Jose, Calif.) in data-dependent mode with dynamic exclusion (Goodlett, et al. *Anal. Chem.* 72, 1112-1118 (2000)). Protein identification was accomplished by use of the SEQUEST computer program (Eng et al. *J. Am. Soc. Mass. Spectrom.* 5, 976-989 (1994)).

Figure 4C:
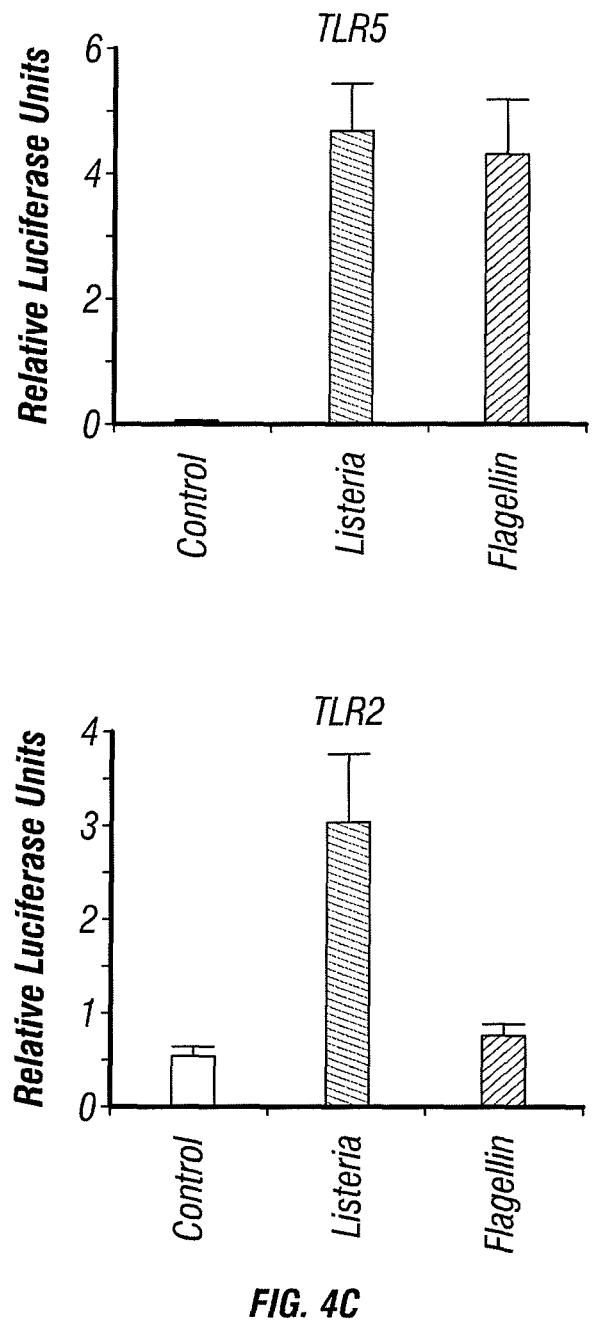

CHO cells expressing an NF-κB luciferase reporter and TLR5 or TLR2 were stimulated with 100 μl/ml *Listeria* supernatant or 33 μg/ml purified *Salmonella* flagellin. Flagellin was purified from *Salmonella typhimurium* (TH4778 fliB− fliC+) by the procedure of Ibrahim et al., *J. Clin. Microbiol.* 22, 1040-1044 (1985). As shown in FIG. 4c, flagellin stimulated TLR5-expressing CHO cells, but not TLR2-expressing CHO cells. The mean and standard deviation of quadruplicate samples are indicated. CHO cells were transfected as described in above Examples with the addition of 0.1 μg of pNeo/Tak, and stable populations of cells expressing the indicated TLR with the luciferase reporters were selected in 100 μg/ml G418. These cells were plated on 96-well plates at 100,000 cells/well, incubated overnight, and processed in luciferase assays as described above.

The observation that flagellin is the TLR5 ligand also is supported by the finding that the flagellated bacteria, *L. monocytogenes* and *P. aeruginosa*, stimulate TLR5, while the TOP10 strain of *E. coli*, that has lost its flagella, does not (FIG. 2b).

Similarly, TLR5-stimulating activity was found in *B. subtilis, L. innocua, S. typhimurium* and *S. minnesota*, all flagellated bacteria, while non-flagellated bacteria such as *H. influenza*, did not activate TLR5.

Thus, the TLR5-stimulating activity purified from *L. monocytogenes* culture supernatants was identified as flagellin by tandem mass spectrometry.

EXAMPLE V

Flagellin Expression in Bacteria Reconstitutes TLR5-Stimulating Activity

This Example shows that flagellin expression in bacteria reconstitutes TLR-stimulating activity, and deletion of flagellin genes abrogates TLR5-stimulating activity.

Figure 5A:
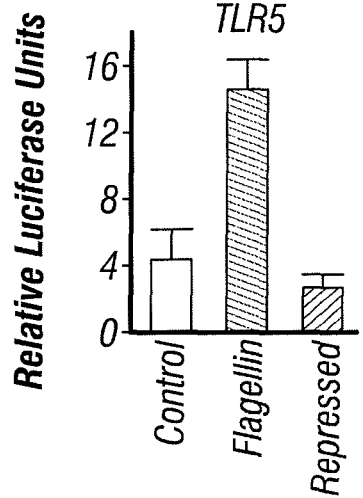
FIGS. 5A-D show that flagellin expression in bacteria reconstitutes TLR5-stimulating activity.
Figure 5B:
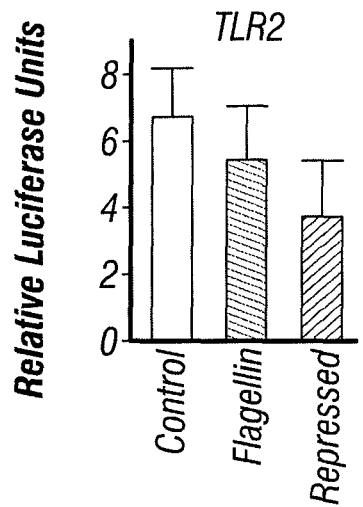

To confirm that flagellin is the sole TLR5 ligand in bacteria, *E. coli* (TOP10) that secrete little TLR5 activity (FIG. 2b) were transformed with the cDNA of *L. monocytogenes* flagellin (flaA) under the control of an inducible promoter. TLR-expressing CHO cells were stimulated for 5 hours with *E. coli* culture supernatants (67 μl/ml) in which expression of *L. monocytogenes* flagellin was induced or repressed. In the control sample, CHO cells were stimulated with supernatants from induced *E. coli* containing the *L. monocytogenes* flagellin gene cloned in the reverse orientation. Supernatants of *E. coli* that were induced to express *L. monocytogenes* flaA contained substantial TLR5-stimulating activity (FIG. 5a), whereas supernatants from *E. coli* in which expression was repressed, or from *E. coli* expressing flaA in the reverse orientation, contained little TLR5 activity in CHO cells expressing an NF-κB luciferase reporter and TLR5 (FIG. 5a) or TLR2 (FIG. 5b). CHO cells expressing an NF-κB luciferase reporter and TLR5 (c) or TLR2 (d) were stimulated for 5 hours with culture supernatants (100 µl/ml) from *S. typhimurium* lacking one copy of flagellin (FliB– fliC+) or both copies of flagellin (FliB+ FliC+). Control is stimulation with LB medium. The mean and standard deviation of quadruplicate samples are indicated.

CHO cells were transfected with TLR2 and TLR5 expression plasmids as described above with the addition of 0.1 µg of pNeo/Tak, and stable populations of cells expressing the indicated TLR with the luciferase reporters were selected in 100 µg/ml G418. These cells were plated on 96-well plates at 100,000 cells/well, incubated overnight, and processed in luciferase assays as described above.

Figure 5C:
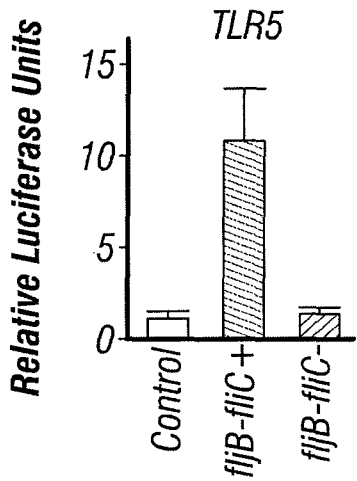
Figure 5D:
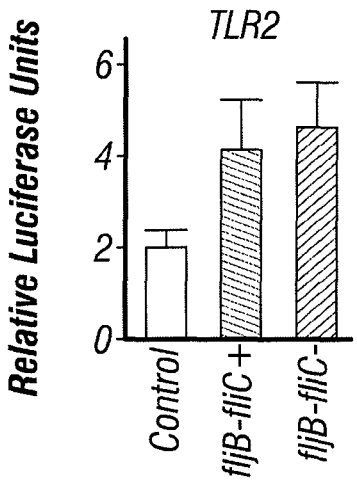

*L. monocytogenes* flagellin is not recognized by TLR2, since supernatants from *E. coli* expressing flaA did not show enhanced TLR2-dependent stimulation of CHO cells relative to supernatants from *E. coli* with repressed flaA expression (FIG. 5b). In addition to the experiments that demonstrate reconstitution of TLR5-stimulating activity by the expression of flagellin, a bacterium from which flagellin had been deleted was tested. It was observed that TLR5-stimulating activity was abrogated in the flagellin deleted strain. *S. typhimurium* possess two genes for flagellin, fliB and fliC (Fujita, J., *J. Gen Microbiol.* 76, 127-34 (1973)). Culture supernatants of fliB– fliC+ *S. typhimurium* contained TLR5-stimulating activity, while culture supernatants from *S. typhimurium* lacking both flagellins (fliB– fliC–) expressed no TLR5-stimulating activity (FIG. 5c). The lack of both flagellin genes had no effect on TLR2-stimulating activity (FIG. 5d). The observed TLR2-stimulating activity found in *S. typhimurium* supernatants most likely was due to bacterial lipoproteins (Underhill, et al. *Nature* 401, 811-5 (1999); Brightbill et al., *Science* 285, 732-6 (1999)). These results indicate that flagellin is the sole TLR5-stimulating activity present in *S. typhimurium* culture supernatant.

Thus, TLR5-stimulating activity was elicited by introducing the flagellin gene into a non-flagellated bacterium, and abrogated by deleting the flagellin genes from a flagellated bacterium.

EXAMPLE VI

Flagellin-Induced System IL-6 Production in Mice

This example shows that TLR signaling is required for the in vivo immune response to flagellin.

To determine if TLR signaling is required for the in vivo immune response to flagellin, wild type mice and mice lacking a component of the TLR5 signal transduction pathway, MyD88, were injected with flagellin and systemic IL-6 production was monitored. MyD88 is an adaptor protein required for TLR5-mediated signal transduction (Aderem A. and Ulevitch, R. J., *Nature* 406:782-787, (2000); Brightbill, H. D. and Modlin. R. L., *Immunology* 101:1-10, (2000)).

MyD88$^{-/-}$ mice (129/SvJ×C57Bl/6 background) were backcrossed for three generations with C57Bl/6 mice (Adachi, O. et al. *Immunity*, 9:143-150 (1998)). Mice from the F$_3$ generation (MyD88$^{-/-}$, n=5) and littermate controls (MyD88$^{+/+}$, n=5) were injected i.p. with 30 µg purified flagellin in 0.5 cc of saline. Blood was sampled at 0, 1, 2, 4 and 8 hours after injection, and IL-6 levels were determined by ELISA (Duoset, R&D Systems, Minneapolis, Minn.).

Figure 6:
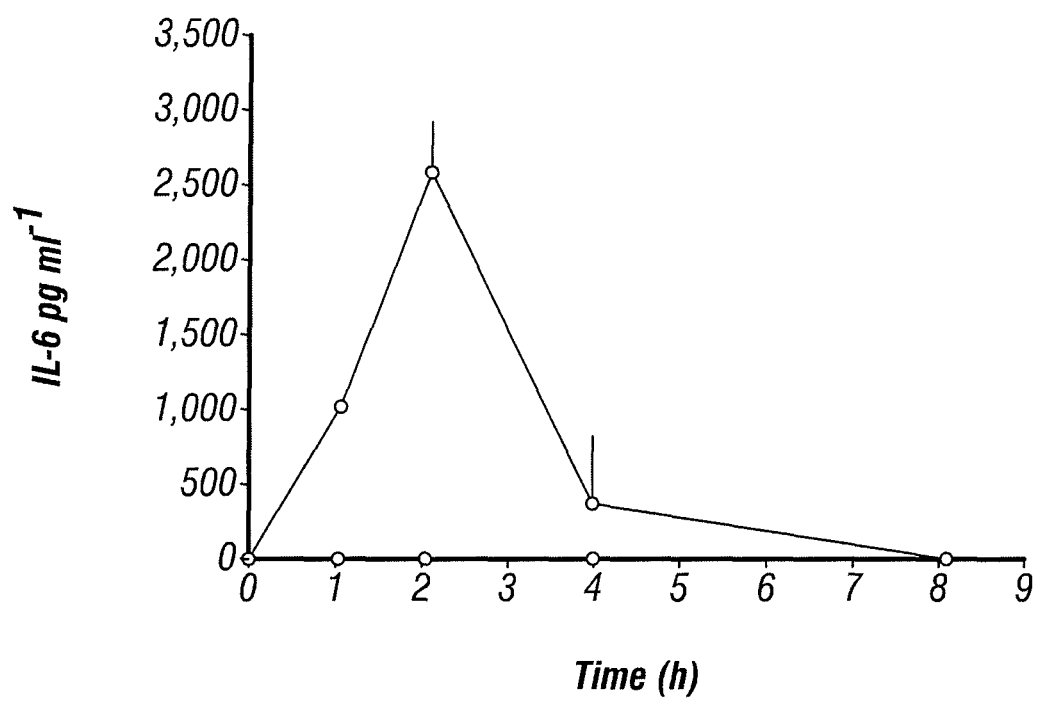
FIG. 6 shows systemic induction of IL-6 in wild type mice treated with purified flagellin.

FIG. 6 shows that flagellin induced systemic IL-6 within 2 h in wile type mice. By contrast, mice deficient in MyD88 were completely unresponsive to flagellin.

Therefore, flagellin stimulates TLR5-mediated responses in vivo.

Throughout this application various publications have been referenced. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention.

The invention claimed is:

1. A method to stimulate a TLR5-mediated enhancement of an antigen specific immune response in subject which method comprises administering to said subject said antigen along with a flagellin polypeptide comprising an amino acid sequence selected from the group consisting of SEQ ID NO:11-SEQ ID NO:34, and
 wherein said flagellin polypeptide does not contain said antigen.

2. The method of claim 1 wherein said flagellin polypeptide consists of an amino acid sequence selected from the group consisting of SEQ ID NO:11- SEQ ID NO:34.

3. The method of claim 1 wherein the flagellin polypeptide further comprises an ADCC targeting molecule.

4. The method of claim 1 wherein said antigen is selected from the group consisting of polypeptides, polysaccharides, pathologically aberrant cells, inactivated and attenuated viruses or bacteria, nucleic acids and toxoids.

5. The method of claim 1 wherein the flagellin polypeptide comprises an amino acid sequence selected from the group consisting of SEQ ID NO:13 - SEQ ID NO:33.

6. The method of claim 5 wherein the flagellin polypeptide further comprises an ADCC targeting molecule.

7. The method of claim 5 wherein said antigen is selected from the group consisting of polypeptides, polysaccharides, pathologically aberrant cells, inactivated and attenuated viruses or bacteria, nucleic acids and toxoids.

8. The method of claim 1 wherein the flagellin polypeptide consists of an amino acid sequence selected from the group consisting of SEQ ID NO:13 - SEQ ID NO:33.

* * * * *

SEQUENCE LISTING

```
<160> NUMBER OF SEQ ID NOS: 43

<210> SEQ ID NO 1
<211> LENGTH: 36
<212> TYPE: DNA
<213> ORGANISM: Salmonella typhimurium flagellin

<400> SEQUENCE: 1
ggtgcggtac agaaccgttt caactccgct attacc                              36

<210> SEQ ID NO 2
<211> LENGTH: 12
<212> TYPE: PRT
<213> ORGANISM: Salmonella typhimurium flagellin

<400> SEQUENCE: 2

Gly Ala Val Gln Asn Arg Phe Asn Ser Ala Ile Thr
 1               5                   10

<210> SEQ ID NO 3
<211> LENGTH: 12
```

```
<212> TYPE: PRT
<213> ORGANISM: Artificial Sequence
<220> FEATURE:
<223> OTHER INFORMATION: synthetic construct

<400> SEQUENCE: 3

Gly Ala Val Ala Asn Arg Phe Asn Ser Ala Ile Thr
 1               5                   10

<210> SEQ ID NO 4
<211> LENGTH: 12
<212> TYPE: PRT
<213> ORGANISM: Artificial Sequence
<220> FEATURE:
<223> OTHER INFORMATION: synthetic construct

<400> SEQUENCE: 4

Gly Ala Val Gln Asn Ala Phe Asn Ser Ala Ile Thr
 1               5                   10

<210> SEQ ID NO 5
<211> LENGTH: 4286
<212> TYPE: DNA
<213> ORGANISM: Mus musculus
<220> FEATURE:
<221> NAME/KEY: CDS
<222> LOCATION: (999)...(3575)

<400> SEQUENCE: 5
```

| | |
|---|---:|
| ttgaaatctc acagcccggt tggttgcagt gacccacttc gttgaacata ttcttcctaa | 60 |
| tcctagtact ttcaatttgc tctattccct ggtgtctatg catttaaatc gactatgggg | 120 |
| ccattcttcc ttgaaccacc acagaagaca ttagctctct gggatccttg ttaattttt | 180 |
| ctcctcttac atagcaccta cgcttggaac atatgccaga cacatctgtg agacacccct | 240 |
| tgccgctgca gctcatggat ggatgctgag ttcccccacg caccacactt cagcaggtgg | 300 |
| gtgtatttct gcttcacatt atactcccac acggccatgc atgtcaggca tggagcaggc | 360 |
| tcataaccca cttaattaag gtgatcatat cagatccttt atcaagatgc atagagtgct | 420 |
| cagtgcctgt actatgatct cggatctttg ggagatgggc tagatagagt ctgggacaga | 480 |
| atacagcaga gaaaccgata tgtttattgt ccgatcatca gctaagcttc tgggagctag | 540 |
| gaatggggct cctggatga acagaagtaa aaatgcctcg tctttatgac tttcaacttc | 600 |
| cctcagcagg tctggaatgg gtgaacaaac actgcctgcg tgggtgataa atagcctctt | 660 |
| tttgctgctt gtttgctgct tttatggttc tgggagggaa cctagaacct agcacatgct | 720 |
| agacaagtcc tctagcactg agctatctcc ccagcttgga tgaaatatct gtaaagtact | 780 |
| ggtgcccgtg tgtaaaatat gcaccattaa gtgttcaaga agaaaagact gggcatttct | 840 |
| gttccaccaa gacaagaaga atctgccagc agaatgtttg cgcagtcatt tgagcaaagg | 900 |
| ggtccaaggg acagtaccct ccagtgctgg ggacccatgt gccgagcctc aggctgtgat | 960 |
| gtggtgttgt ttttaattct ctcttttccc ataggatc atg gca tgt caa ctt gac | 1016 |

|  |  |
|---|---:|
|                                                                         Met Ala Cys Gln Leu Asp | |
|                                                                            1              5 | |
| ttg ctc ata ggt gtg atc ttc atg gcc agc ccc gtg ttg gta ata tct | 1064 |
| Leu Leu Ile Gly Val Ile Phe Met Ala Ser Pro Val Leu Val Ile Ser | |
|           10               15                  20 | |
| ccc tgt tct tca gac ggc agg ata gcc ttt ttc cga ggc tgt aac ctc | 1112 |
| Pro Cys Ser Ser Asp Gly Arg Ile Ala Phe Phe Arg Gly Cys Asn Leu | |
|      25               30                  35 | |
| acc cag att ccc tgg atc ctc aat act acc act gag agg ctc ctg ctc | 1160 |

|  |  |  |  |  |  |  |  |  |  |  |  |  |
|---|---|---|---|---|---|---|---|---|---|---|---|---|
| Thr | Gln | Ile | Pro | Trp | Ile | Leu | Asn | Thr | Thr | Thr | Glu | Arg Leu Leu Leu |
|  | 40 |  |  |  | 45 |  |  |  |  | 50 |  |  |

```
agc ttc aac tat atc agt atg gtg gtt gcc aca tca ttt cca ctc ctg      1208
Ser Phe Asn Tyr Ile Ser Met Val Val Ala Thr Ser Phe Pro Leu Leu
 55                  60                  65                  70 gag cgg ctc cag ttg ctg gag ctg ggg acc cag tat gct aac ttg acc      1256
Glu Arg Leu Gln Leu Leu Glu Leu Gly Thr Gln Tyr Ala Asn Leu Thr
                 75                  80                  85 att ggt cca ggg gct ttc aga aac ctg ccc aat ctt agg atc ttg gac      1304
Ile Gly Pro Gly Ala Phe Arg Asn Leu Pro Asn Leu Arg Ile Leu Asp
             90                  95                 100 ttg ggc caa agc cag atc gaa gtc ttg aat cga gat gcc ttt caa ggt      1352
Leu Gly Gln Ser Gln Ile Glu Val Leu Asn Arg Asp Ala Phe Gln Gly
        105                 110                 115 ctg ccc cat ctc ttg gaa ctt cgg ctg ttt tcc tgt gga ctc tcc agt      1400
Leu Pro His Leu Leu Glu Leu Arg Leu Phe Ser Cys Gly Leu Ser Ser
    120                 125                 130 gct gtg tta agt gac ggt tac ttc aga aat cta tat tca tta gct cgc      1448
Ala Val Leu Ser Asp Gly Tyr Phe Arg Asn Leu Tyr Ser Leu Ala Arg
135                 140                 145                 150 tta gac cta tct ggc aac cag att cac agc ctc cgc ctc cat tct tca      1496
Leu Asp Leu Ser Gly Asn Gln Ile His Ser Leu Arg Leu His Ser Ser
                155                 160                 165 ttc cgg gaa ctg aat tcc tta agc gac gta aat ttt gct ttc aac caa      1544
Phe Arg Glu Leu Asn Ser Leu Ser Asp Val Asn Phe Ala Phe Asn Gln
            170                 175                 180 ata ttc act ata tgt gaa gat gaa ctc gag cct ctg cag ggc aaa aca      1592
Ile Phe Thr Ile Cys Glu Asp Glu Leu Glu Pro Leu Gln Gly Lys Thr
        185                 190                 195 ctg tct ttc ttt ggc ctc aaa tta act aag ctg ttc agc aga gtc tct      1640
Leu Ser Phe Phe Gly Leu Lys Leu Thr Lys Leu Phe Ser Arg Val Ser
    200                 205                 210 gtg ggc tgg gag aca tgc agg aac ccc ttc aga ggc gtg agg cta gaa      1688
Val Gly Trp Glu Thr Cys Arg Asn Pro Phe Arg Gly Val Arg Leu Glu
215                 220                 225                 230 act cta gat ctt tct gaa aat ggc tgg acg gtg gac atc aca agg aac      1736
Thr Leu Asp Leu Ser Glu Asn Gly Trp Thr Val Asp Ile Thr Arg Asn
                235                 240                 245 ttc agc aac atc atc cag gga agc cag att tcc tct ttg att ctt aaa      1784
Phe Ser Asn Ile Ile Gln Gly Ser Gln Ile Ser Ser Leu Ile Leu Lys
            250                 255                 260 cac cac atc atg ggt cct ggc ttt ggc ttc cag aac atc aga gat cct      1832
His His Ile Met Gly Pro Gly Phe Gly Phe Gln Asn Ile Arg Asp Pro
        265                 270                 275 gac cag agc aca ttt gcc agc ctg gcc aga agt tcg gtg ctg caa ctg      1880
Asp Gln Ser Thr Phe Ala Ser Leu Ala Arg Ser Ser Val Leu Gln Leu
    280                 285                 290 gac ctt tcg cac ggc ttt atc ttc tcc ttg aat cct cga ctg ttt ggg      1928
Asp Leu Ser His Gly Phe Ile Phe Ser Leu Asn Pro Arg Leu Phe Gly
295                 300                 305                 310 aca ctg aag gat ttg aag atg ctg aac ctt gcc ttc aac aag ata aac      1976
Thr Leu Lys Asp Leu Lys Met Leu Asn Leu Ala Phe Asn Lys Ile Asn
                315                 320                 325 aag att gga gag aat gcc ttt tat ggg ctt gac agc ctc cag gtt ctc      2024
Lys Ile Gly Glu Asn Ala Phe Tyr Gly Leu Asp Ser Leu Gln Val Leu
            330                 335                 340 aat cta tcc tat aat ctt ttg ggg gaa ctc tat aat tcc aac ttc tat      2072
Asn Leu Ser Tyr Asn Leu Leu Gly Glu Leu Tyr Asn Ser Asn Phe Tyr
        345                 350                 355
```

-continued

| | | |
|---|---|---|
| ggg ctt cct aga gta gcc tac gtt gac ctt caa agg aac cac att ggg<br>Gly Leu Pro Arg Val Ala Tyr Val Asp Leu Gln Arg Asn His Ile Gly<br>360                        365                       370 | 2120 | |
| atc att caa gac caa aca ttc aga tta tta aaa acg tta caa acc tta<br>Ile Ile Gln Asp Gln Thr Phe Arg Leu Leu Lys Thr Leu Gln Thr Leu<br>375                     380                        385                   390 | 2168 | |
| gat ctc cgt gac aat gct ctt aag gcc att ggt ttt att cca agc ata<br>Asp Leu Arg Asp Asn Ala Leu Lys Ala Ile Gly Phe Ile Pro Ser Ile<br>               395                    400                    405 | 2216 | |
| cag atg gtc ctc ctg gga ggc aat aag ctg gtc cat ttg cca cac atc<br>Gln Met Val Leu Leu Gly Gly Asn Lys Leu Val His Leu Pro His Ile<br>          410                   415                  420 | 2264 | |
| cac ttt act gcc aac ttc cta gag tta tct gaa aac agg cta gaa aac<br>His Phe Thr Ala Asn Phe Leu Glu Leu Ser Glu Asn Arg Leu Glu Asn<br>        425                    430                    435 | 2312 | |
| ctg tcc gac ctc tac ttc ctc cga gtc ccc cag ctc cag ttt ctc<br>Leu Ser Asp Leu Tyr Phe Leu Arg Val Pro Gln Leu Gln Phe Leu<br>440                      445                      450 | 2360 | |
| atc ttg aat cag aat cgc ctt tcg tca tgc aag gca gcc cac act ccc<br>Ile Leu Asn Gln Asn Arg Leu Ser Ser Cys Lys Ala Ala His Thr Pro<br>455                   460                    465                    470 | 2408 | |
| tcg gag aac cca agc tta gaa cag ctt ttc ctt aca gag aat atg ctg<br>Ser Glu Asn Pro Ser Leu Glu Gln Leu Phe Leu Thr Glu Asn Met Leu<br>               475                    480                    485 | 2456 | |
| cag ctg gcc tgg gag acc ggc ctc tgt tgg gat gtt ttt caa ggc ctt<br>Gln Leu Ala Trp Glu Thr Gly Leu Cys Trp Asp Val Phe Gln Gly Leu<br>          490                   495                  500 | 2504 | |
| tcc cgc ctc cag att ctt tac ctg agt aat aac tac ctt aat ttc ctt<br>Ser Arg Leu Gln Ile Leu Tyr Leu Ser Asn Asn Tyr Leu Asn Phe Leu<br>        505                    510                    515 | 2552 | |
| cca cct ggg ata ttt aac gac ctg gtt gca tta cgg atg ctt agt ctt<br>Pro Pro Gly Ile Phe Asn Asp Leu Val Ala Leu Arg Met Leu Ser Leu<br>520                      525                      530 | 2600 | |
| agt gct aac aag ctg acc gtg ctc tct ccg ggc agt tta cct gct aat<br>Ser Ala Asn Lys Leu Thr Val Leu Ser Pro Gly Ser Leu Pro Ala Asn<br>535                     540                    545                    550 | 2648 | |
| tta gag att ctc gac ata tct aga aat cag ctt ttg tgt cct gac cct<br>Leu Glu Ile Leu Asp Ile Ser Arg Asn Gln Leu Leu Cys Pro Asp Pro<br>               555                    560                    565 | 2696 | |
| gct ttg ttt tct tcg ctt cgt gtt ttg gac ata act cat aac gag ttc<br>Ala Leu Phe Ser Ser Leu Arg Val Leu Asp Ile Thr His Asn Glu Phe<br>            570                    575                    580 | 2744 | |
| gtc tgc aac tgt gaa ctt agc act ttt atc tcc tgg ctc aac caa acc<br>Val Cys Asn Cys Glu Leu Ser Thr Phe Ile Ser Trp Leu Asn Gln Thr<br>          585                    590                    595 | 2792 | |
| aac gtc acc ctg ttc ggc tct cct gca gac gtg tat tgc atg tac cct<br>Asn Val Thr Leu Phe Gly Ser Pro Ala Asp Val Tyr Cys Met Tyr Pro<br>600                      605                      610 | 2840 | |
| aac tca ctg cta ggg ggc tcc ctc tac aac ata tcc acc gaa gac tgc<br>Asn Ser Leu Leu Gly Gly Ser Leu Tyr Asn Ile Ser Thr Glu Asp Cys<br>615                   620                    625                    630 | 2888 | |
| gat gaa gag gaa gcc atg cgg tcc cta aag ttt tcc ctt ttc atc ctg<br>Asp Glu Glu Glu Ala Met Arg Ser Leu Lys Phe Ser Leu Phe Ile Leu<br>               635                    640                    645 | 2936 | |
| tgc acg gtc act ttg act cta ttc ctc gtc atc acc ctt gta gtc ata<br>Cys Thr Val Thr Leu Thr Leu Phe Leu Val Ile Thr Leu Val Val Ile<br>          650                    655                    660 | 2984 | |
| aag ttc cgg gga atc tgt ttc ctg tgc tat aag acc atc cag aag ctg<br>Lys Phe Arg Gly Ile Cys Phe Leu Cys Tyr Lys Thr Ile Gln Lys Leu<br>665                      670                    675 | 3032 | |

-continued

| | | |
|---|---|---|
| gtg ttc aag gac aag gtc tgg agt ttg gaa cct ggt gca tat aga tat<br>Val Phe Lys Asp Lys Val Trp Ser Leu Glu Pro Gly Ala Tyr Arg Tyr<br>680                685                690 | 3080 | |
| gat gcc tac ttc tgc ttc agc agc aaa gac ttt gaa tgg gca cag aat<br>Asp Ala Tyr Phe Cys Phe Ser Ser Lys Asp Phe Glu Trp Ala Gln Asn<br>695                    700                705                710 | 3128 | |
| gct ttg ctc aaa cac ctg gat gct cac tac agt tcc cga aac agg ctc<br>Ala Leu Leu Lys His Leu Asp Ala His Tyr Ser Ser Arg Asn Arg Leu<br>            715                720                725 | 3176 | |
| agg cta tgc ttt gaa gaa aga gac ttc att ccg ggg gaa aac cat atc<br>Arg Leu Cys Phe Glu Glu Arg Asp Phe Ile Pro Gly Glu Asn His Ile<br>                730                735                740 | 3224 | |
| tcc aac atc cag gcg gct gtc tgg ggc agc agg aag acg gtg tgt cta<br>Ser Asn Ile Gln Ala Ala Val Trp Gly Ser Arg Lys Thr Val Cys Leu<br>            745                750                755 | 3272 | |
| gtg agc aga cac ttc ctg aag gat ggt tgg tgc ctg gag gcc ttc agg<br>Val Ser Arg His Phe Leu Lys Asp Gly Trp Cys Leu Glu Ala Phe Arg<br>760                765                770 | 3320 | |
| tat gcc cag agc cgg agt ctg tct gac ctc aag agc att ctc atc gtg<br>Tyr Ala Gln Ser Arg Ser Leu Ser Asp Leu Lys Ser Ile Leu Ile Val<br>775                780                785                790 | 3368 | |
| gtg gtg gtg gga tcg ctg tcc cag tat cag ctg atg aga cat gag acc<br>Val Val Val Gly Ser Leu Ser Gln Tyr Gln Leu Met Arg His Glu Thr<br>            795                800                805 | 3416 | |
| atc aga ggg ttt ctg caa aag caa cag tac ttg agg tgg cct gaa gac<br>Ile Arg Gly Phe Leu Gln Lys Gln Gln Tyr Leu Arg Trp Pro Glu Asp<br>                810                815                820 | 3464 | |
| ctc cag gat gtt ggc tgg ttt ctc gat aaa ctc tcc gga tgc att cta<br>Leu Gln Asp Val Gly Trp Phe Leu Asp Lys Leu Ser Gly Cys Ile Leu<br>            825                830                835 | 3512 | |
| aag gaa gaa aaa gga aag aaa aga agc agt tcc atc cag ttg cga acc<br>Lys Glu Glu Lys Gly Lys Lys Arg Ser Ser Ser Ile Gln Leu Arg Thr<br>840                845                850 | 3560 | |
| ata gca acc att tcc tagcaggagc gcctcctagc agaagtgcaa gcatcgtaga<br>Ile Ala Thr Ile Ser<br>855 | 3615 | |
| taactctcca cgctttatcc gcacagccgc tgggggtcct tccctggagt cattttctg | 3675 | |
| acaatgaaaa caacaccaat ctcttgattt ttcatgtcaa cagggagctt tgtcttcact | 3735 | |
| gttttccaaa tggaaagtaa gaggtccaga aagctgcctc taagggctct cacctgccat | 3795 | |
| tgatgtcctt tcaggcccaa tgacatggtt tccctccatc ctattgcgta ctgtctgcta | 3855 | |
| cccaggtggc aagagcacct tgggagaagt tacaggcagc ttcatgcttt ctgtgctgtt | 3915 | |
| cagttcaaaa gcaggtgcct tgagaatcct gaattcaagc actctgtaga acatggacag | 3975 | |
| acaagatggg tccttctctg gccataggca tgagggccag ttgctgagga ctgctctcac | 4035 | |
| tacacctaag tgcacaagtg ataagaagtt ggacagatag acagatagca gcagtcccat | 4095 | |
| tgctgtagcc agaatgcact tatttcctgt tctgaccctg caggcccagc ttttggggac | 4155 | |
| cacagccatg ttctgcacgg gacctctcaa cctggcattc atgcccttte acgacttagc | 4215 | |
| accggcctgc ccttctttct tccccacaac tatacaagag ctgttgcaac cactgaaaaa | 4275 | |
| aaaaaaaaaa a | 4286 | |

<210> SEQ ID NO 6
<211> LENGTH: 859
<212> TYPE: PRT
<213> ORGANISM: Mus musculus

<400> SEQUENCE: 6

```
Met Ala Cys Gln Leu Asp Leu Leu Ile Gly Val Ile Phe Met Ala Ser
 1               5                  10                  15

Pro Val Leu Val Ile Ser Pro Cys Ser Ser Asp Gly Arg Ile Ala Phe
            20                  25                  30

Phe Arg Gly Cys Asn Leu Thr Gln Ile Pro Trp Ile Leu Asn Thr Thr
        35                  40                  45

Thr Glu Arg Leu Leu Leu Ser Phe Asn Tyr Ile Ser Met Val Val Ala
    50                  55                  60

Thr Ser Phe Pro Leu Leu Glu Arg Leu Gln Leu Leu Glu Leu Gly Thr
65                  70                  75                  80

Gln Tyr Ala Asn Leu Thr Ile Gly Pro Gly Ala Phe Arg Asn Leu Pro
                85                  90                  95

Asn Leu Arg Ile Leu Asp Leu Gly Gln Ser Gln Ile Glu Val Leu Asn
            100                 105                 110

Arg Asp Ala Phe Gln Gly Leu Pro His Leu Leu Glu Leu Arg Leu Phe
        115                 120                 125

Ser Cys Gly Leu Ser Ser Ala Val Leu Ser Asp Gly Tyr Phe Arg Asn
    130                 135                 140

Leu Tyr Ser Leu Ala Arg Leu Asp Leu Ser Gly Asn Gln Ile His Ser
145                 150                 155                 160

Leu Arg Leu His Ser Ser Phe Arg Glu Leu Asn Ser Leu Ser Asp Val
                165                 170                 175

Asn Phe Ala Phe Asn Gln Ile Phe Thr Ile Cys Glu Asp Glu Leu Glu
            180                 185                 190

Pro Leu Gln Gly Lys Thr Leu Ser Phe Phe Gly Leu Lys Leu Thr Lys
        195                 200                 205

Leu Phe Ser Arg Val Ser Val Gly Trp Glu Thr Cys Arg Asn Pro Phe
    210                 215                 220

Arg Gly Val Arg Leu Glu Thr Leu Asp Leu Ser Glu Asn Gly Trp Thr
225                 230                 235                 240

Val Asp Ile Thr Arg Asn Phe Ser Asn Ile Ile Gln Gly Ser Gln Ile
                245                 250                 255

Ser Ser Leu Ile Leu Lys His His Ile Met Gly Pro Gly Phe Gly Phe
            260                 265                 270

Gln Asn Ile Arg Asp Pro Asp Gln Ser Thr Phe Ala Ser Leu Ala Arg
        275                 280                 285

Ser Ser Val Leu Gln Leu Asp Leu Ser His Gly Phe Ile Phe Ser Leu
    290                 295                 300

Asn Pro Arg Leu Phe Gly Thr Leu Lys Asp Leu Lys Met Leu Asn Leu
305                 310                 315                 320

Ala Phe Asn Lys Ile Asn Lys Ile Gly Glu Asn Ala Phe Tyr Gly Leu
                325                 330                 335

Asp Ser Leu Gln Val Leu Asn Leu Ser Tyr Asn Leu Leu Gly Glu Leu
            340                 345                 350

Tyr Asn Ser Asn Phe Tyr Gly Leu Pro Arg Val Ala Tyr Val Asp Leu
        355                 360                 365

Gln Arg Asn His Ile Gly Ile Ile Gln Asp Gln Thr Phe Arg Leu Leu
    370                 375                 380

Lys Thr Leu Gln Thr Leu Asp Leu Arg Asp Asn Ala Leu Lys Ala Ile
385                 390                 395                 400

Gly Phe Ile Pro Ser Ile Gln Met Val Leu Leu Gly Gly Asn Lys Leu
                405                 410                 415
```

```
Val His Leu Pro His Ile His Phe Thr Ala Asn Phe Leu Glu Leu Ser
            420                 425                 430

Glu Asn Arg Leu Glu Asn Leu Ser Asp Leu Tyr Phe Leu Arg Val
        435                 440                 445

Pro Gln Leu Gln Phe Leu Ile Leu Asn Gln Asn Arg Leu Ser Ser Cys
    450                 455                 460

Lys Ala Ala His Thr Pro Ser Glu Asn Pro Ser Leu Glu Gln Leu Phe
465                 470                 475                 480

Leu Thr Glu Asn Met Leu Gln Leu Ala Trp Glu Thr Gly Leu Cys Trp
                485                 490                 495

Asp Val Phe Gln Gly Leu Ser Arg Leu Gln Ile Leu Tyr Leu Ser Asn
            500                 505                 510

Asn Tyr Leu Asn Phe Leu Pro Pro Gly Ile Phe Asn Asp Leu Val Ala
        515                 520                 525

Leu Arg Met Leu Ser Leu Ser Ala Asn Lys Leu Thr Val Leu Ser Pro
    530                 535                 540

Gly Ser Leu Pro Ala Asn Leu Glu Ile Leu Asp Ile Ser Arg Asn Gln
545                 550                 555                 560

Leu Leu Cys Pro Asp Pro Ala Leu Phe Ser Ser Leu Arg Val Leu Asp
                565                 570                 575

Ile Thr His Asn Glu Phe Val Cys Asn Cys Glu Leu Ser Thr Phe Ile
            580                 585                 590

Ser Trp Leu Asn Gln Thr Asn Val Thr Leu Phe Gly Ser Pro Ala Asp
        595                 600                 605

Val Tyr Cys Met Tyr Pro Asn Ser Leu Leu Gly Gly Ser Leu Tyr Asn
    610                 615                 620

Ile Ser Thr Glu Asp Cys Asp Glu Glu Ala Met Arg Ser Leu Lys
625                 630                 635                 640

Phe Ser Leu Phe Ile Leu Cys Thr Val Thr Leu Thr Leu Phe Leu Val
                645                 650                 655

Ile Thr Leu Val Val Ile Lys Phe Arg Gly Ile Cys Phe Leu Cys Tyr
            660                 665                 670

Lys Thr Ile Gln Lys Leu Val Phe Lys Asp Lys Val Trp Ser Leu Glu
        675                 680                 685

Pro Gly Ala Tyr Arg Tyr Asp Ala Tyr Phe Cys Phe Ser Ser Lys Asp
    690                 695                 700

Phe Glu Trp Ala Gln Asn Ala Leu Leu Lys His Leu Asp Ala His Tyr
705                 710                 715                 720

Ser Ser Arg Asn Arg Leu Arg Leu Cys Phe Glu Glu Arg Asp Phe Ile
                725                 730                 735

Pro Gly Glu Asn His Ile Ser Asn Ile Gln Ala Ala Val Trp Gly Ser
            740                 745                 750

Arg Lys Thr Val Cys Leu Val Ser Arg His Phe Leu Lys Asp Gly Trp
        755                 760                 765

Cys Leu Glu Ala Phe Arg Tyr Ala Gln Ser Arg Ser Leu Ser Asp Leu
    770                 775                 780

Lys Ser Ile Leu Ile Val Val Val Val Gly Ser Leu Ser Gln Tyr Gln
785                 790                 795                 800

Leu Met Arg His Glu Thr Ile Arg Gly Phe Leu Gln Lys Gln Gln Tyr
                805                 810                 815

Leu Arg Trp Pro Glu Asp Leu Gln Asp Val Gly Trp Phe Leu Asp Lys
            820                 825                 830
```

```
Leu Ser Gly Cys Ile Leu Lys Glu Glu Lys Gly Lys Lys Arg Ser Ser
            835                 840                 845

Ser Ile Gln Leu Arg Thr Ile Ala Thr Ile Ser
    850                 855

<210> SEQ ID NO 7
<211> LENGTH: 3431
<212> TYPE: DNA
<213> ORGANISM: Homo sapiens
<220> FEATURE:
<221> NAME/KEY: CDS
<222> LOCATION: (704)...(3277)

<400> SEQUENCE: 7
ggcttatagg gctcgagcgg ccgcccgggc aggtatagaa ttcagcggcc gctgaattct      60
agggttttca ggagcccgag cgagggcgcc gcttttgcgt ccgggaggag ccaaccgtgg     120
cgcaggcggc gcggggaggc gtcccagagt ctcactctgc cgcccaggct ggactgcagt     180
gacacaatct cggctgactg caaccactgc ctccagggtt caagcgattc tcttgcctca     240
gcctcccaag tagctgggat tacagattga tgttcatgtt cctggcacta ctacaagatt     300
catactcctg atgctactga caacgtggct ctctccacagt caccaaaacca gggatgctat     360 actggacttc cctactctca tctgctccag ccccctgacc ttatagttgc ccagctttcc     420
tggcaattga ctttgcccat caatacacag gatttagcat ccagggaaga tgtcggagcc     480
tcagatgtta attttctaat tgagaatgtt ggcgctgtcc gaacctggag acagaaaaac     540
aaaaagtcct ttctcctgat tcaccaaaaa ataaaatact gactaccatc actgtgatga     600
gattcctata gtctcaggaa ctgaagtctt taaacaacca gggaccctct gcccctagaa     660
taagaacata ctagaagtcc cttctgctag gacaacgagg atc atg gga gac cac      715
                                              Met Gly Asp His
                                                1 ctg gac ctt ctc cta gga gtg gtg ctc atg gcc ggt cct gtg ttt gga      763
Leu Asp Leu Leu Leu Gly Val Val Leu Met Ala Gly Pro Val Phe Gly
  5                  10                  15                  20 att cct tcc tgc tcc ttt gat ggc cga ata gcc ttt tat cgt ttc tgc      811
Ile Pro Ser Cys Ser Phe Asp Gly Arg Ile Ala Phe Tyr Arg Phe Cys
             25                  30                  35 aac ctc acc cag gtc ccc cag gtc ctc aac acc act gag agg ctc ctg      859
Asn Leu Thr Gln Val Pro Gln Val Leu Asn Thr Thr Glu Arg Leu Leu
         40                  45                  50 ctg agc ttc aac tat atc agg aca gtc act gct tca tcc ttc ccc ttt      907
Leu Ser Phe Asn Tyr Ile Arg Thr Val Thr Ala Ser Ser Phe Pro Phe
     55                  60                  65 ctg gaa cag ctg cag ctg ctg gag ctc ggg agc cag tat acc ccc ttg      955
Leu Glu Gln Leu Gln Leu Leu Glu Leu Gly Ser Gln Tyr Thr Pro Leu
 70                  75                  80 act att gac aag gag gcc ttc aga aac ctg ccc aac ctt aga atc ttg     1003
Thr Ile Asp Lys Glu Ala Phe Arg Asn Leu Pro Asn Leu Arg Ile Leu
 85                  90                  95                 100 gac ctg gga agt agt aag ata tac ttc ttg cat cca gat gct ttt cag     1051
Asp Leu Gly Ser Ser Lys Ile Tyr Phe Leu His Pro Asp Ala Phe Gln
                105                 110                 115 gga ctg ttc cat ctg ttt gaa ctt aga ctg tat ttc tgt ggt ctc tct     1099
Gly Leu Phe His Leu Phe Glu Leu Arg Leu Tyr Phe Cys Gly Leu Ser
            120                 125                 130 gat gct gta ttg aaa gat ggt tat ttc aga aat tta aag gct tta act     1147
Asp Ala Val Leu Lys Asp Gly Tyr Phe Arg Asn Leu Lys Ala Leu Thr
        135                 140                 145
```

```
cgc ttg gat cta tcc aaa aat cag att cgt agc ctt tac ctt cat cct    1195
Arg Leu Asp Leu Ser Lys Asn Gln Ile Arg Ser Leu Tyr Leu His Pro
    150                 155                 160 tca ttt ggg aag ttg aat tcc tta aag tcc ata gat ttt tcc tcc aac    1243
Ser Phe Gly Lys Leu Asn Ser Leu Lys Ser Ile Asp Phe Ser Ser Asn
165                 170                 175                 180 caa ata ttc ctt gta tgt gaa cat gag ctc gag ccc cta caa ggg aaa    1291
Gln Ile Phe Leu Val Cys Glu His Glu Leu Glu Pro Leu Gln Gly Lys
            185                 190                 195 acg ctc tcc ttt ttt agc ctc gca gct aat agc ttg tat agc aga gtc    1339
Thr Leu Ser Phe Phe Ser Leu Ala Ala Asn Ser Leu Tyr Ser Arg Val
        200                 205                 210 tca gtg gac tgg gga aaa tgt atg aac cca ttc aga aac atg gtg ctg    1387
Ser Val Asp Trp Gly Lys Cys Met Asn Pro Phe Arg Asn Met Val Leu
    215                 220                 225 gag ata gta gat gtt tct gga aat ggc tgg aca gtg gac atc aca gga    1435
Glu Ile Val Asp Val Ser Gly Asn Gly Trp Thr Val Asp Ile Thr Gly
230                 235                 240 aac ttt agc aat gcc atc agc aaa agc cag gcc ttc tct ttg att ctt    1483
Asn Phe Ser Asn Ala Ile Ser Lys Ser Gln Ala Phe Ser Leu Ile Leu
245                 250                 255                 260 gcc cac cac atc atg ggt gcc ggg ttt ggc ttc cat aac atc aaa gat    1531
Ala His His Ile Met Gly Ala Gly Phe Gly Phe His Asn Ile Lys Asp
            265                 270                 275 cct gac cag aac aca ttt gct ggc ctg gcc aga agt tca gtg aga cac    1579
Pro Asp Gln Asn Thr Phe Ala Gly Leu Ala Arg Ser Ser Val Arg His
        280                 285                 290 ctg gac ctt tca cat ggg ttt gtc ttc tcc ctg aac tcg cga gtc ttt    1627
Leu Asp Leu Ser His Gly Phe Val Phe Ser Leu Asn Ser Arg Val Phe
    295                 300                 305 gag aca ctc aag gat ttg aag gtt ctg aac ctt gcc tac aac aag ata    1675
Glu Thr Leu Lys Asp Leu Lys Val Leu Asn Leu Ala Tyr Asn Lys Ile
310                 315                 320 aat aag att gca gat gaa gca ttt tac gga ctt gac aac ctc caa gtt    1723
Asn Lys Ile Ala Asp Glu Ala Phe Tyr Gly Leu Asp Asn Leu Gln Val
325                 330                 335                 340 ctc aat ttg tca tat aac ctt ctg ggg gaa ctt tgc agt tcg aat ttc    1771
Leu Asn Leu Ser Tyr Asn Leu Leu Gly Glu Leu Cys Ser Ser Asn Phe
            345                 350                 355 tat gga cta cct aag gta gcc tac att gat ttg caa aag aat cac att    1819
Tyr Gly Leu Pro Lys Val Ala Tyr Ile Asp Leu Gln Lys Asn His Ile
        360                 365                 370 gca ata att caa gac caa aca ttc aaa ttc ctg gaa aaa tta cag acc    1867
Ala Ile Ile Gln Asp Gln Thr Phe Lys Phe Leu Glu Lys Leu Gln Thr
    375                 380                 385 ttg gat ctc cga gac aat gct ctt aca acc att cat ttt att cca agc    1915
Leu Asp Leu Arg Asp Asn Ala Leu Thr Thr Ile His Phe Ile Pro Ser
390                 395                 400 ata ccc gat atc ttc ttg agt ggc aat aaa cta gtg act ttg cca aag    1963
Ile Pro Asp Ile Phe Leu Ser Gly Asn Lys Leu Val Thr Leu Pro Lys
405                 410                 415                 420 atc aac ctt aca gcg aac ctc atc cac tta tca gaa aac agg cta gaa    2011
Ile Asn Leu Thr Ala Asn Leu Ile His Leu Ser Glu Asn Arg Leu Glu
            425                 430                 435 aat cta gat att ctc tac ttt ctc cta cgg gta cct cat ctc cag att    2059
Asn Leu Asp Ile Leu Tyr Phe Leu Leu Arg Val Pro His Leu Gln Ile
        440                 445                 450 ctc att tta aat caa aat cgc ttc tcc tcc tgt agt gga gat caa acc    2107
Leu Ile Leu Asn Gln Asn Arg Phe Ser Ser Cys Ser Gly Asp Gln Thr
    455                 460                 465
```

```
cct tca gag aat ccc agc tta gaa cag ctt ttc ctt gga gaa aat atg    2155
Pro Ser Glu Asn Pro Ser Leu Glu Gln Leu Phe Leu Gly Glu Asn Met
    470             475                 480 ttg caa ctt gcc tgg gaa act gag ctc tgt tgg gat gtt ttt gag gga    2203
Leu Gln Leu Ala Trp Glu Thr Glu Leu Cys Trp Asp Val Phe Glu Gly
485             490                 495                 500 ctt tct cat ctt caa gtt ctg tat ttg aat cat aac tat ctt aat tcc    2251
Leu Ser His Leu Gln Val Leu Tyr Leu Asn His Asn Tyr Leu Asn Ser
                505                 510                 515 ctt cca cca gga gta ttt agc cat ctg act gca tta agg gga cta agc    2299
Leu Pro Pro Gly Val Phe Ser His Leu Thr Ala Leu Arg Gly Leu Ser
            520                 525                 530 ctc aac tcc aac agg ctg aca gtt ctt tct cac aat gat tta cct gct    2347
Leu Asn Ser Asn Arg Leu Thr Val Leu Ser His Asn Asp Leu Pro Ala
        535                 540                 545 aat tta gag atc ctg gac ata tcc agg aac cag ctc cta gct cct aat    2395
Asn Leu Glu Ile Leu Asp Ile Ser Arg Asn Gln Leu Leu Ala Pro Asn
    550                 555                 560 cct gat gta ttt gta tca ctt agt gtc ttg gat ata act cat aac aag    2443
Pro Asp Val Phe Val Ser Leu Ser Val Leu Asp Ile Thr His Asn Lys
565             570                 575                 580 ttc att tgt gaa tgt gaa ctt agc act ttt atc aat tgg ctt aat cac    2491
Phe Ile Cys Glu Cys Glu Leu Ser Thr Phe Ile Asn Trp Leu Asn His
                585                 590                 595 acc aat gtc act ata gct ggg cct cct gca gac ata tat tgt gtg tac    2539
Thr Asn Val Thr Ile Ala Gly Pro Pro Ala Asp Ile Tyr Cys Val Tyr
                600                 605                 610 cct gac tcg ctc tct ggg gtt tcc ctc ttc tct ctt tcc acg gaa ggt    2587
Pro Asp Ser Leu Ser Gly Val Ser Leu Phe Ser Leu Ser Thr Glu Gly
            615                 620                 625 tgt gat gaa gag gaa gtc tta aag tcc cta aag ttc tcc ctt ttc att    2635
Cys Asp Glu Glu Glu Val Leu Lys Ser Leu Lys Phe Ser Leu Phe Ile
        630                 635                 640 gta tgc act gtc act ctg act ctg ttc ctc atg acc atc ctc aca gtc    2683
Val Cys Thr Val Thr Leu Thr Leu Phe Leu Met Thr Ile Leu Thr Val
645             650                 655                 660 aca aag ttc cgg ggc ttc tgt ttt atc tgt tat aag aca gcc cag aga    2731
Thr Lys Phe Arg Gly Phe Cys Phe Ile Cys Tyr Lys Thr Ala Gln Arg
                665                 670                 675 ctg gtg ttc aag gac cat ccc cag ggc aca gaa cct gat atg tac aaa    2779
Leu Val Phe Lys Asp His Pro Gln Gly Thr Glu Pro Asp Met Tyr Lys
                680                 685                 690 tat gat gcc tat ttg tgc ttc agc agc aaa gac ttc aca tgg gtg cag    2827
Tyr Asp Ala Tyr Leu Cys Phe Ser Ser Lys Asp Phe Thr Trp Val Gln
            695                 700                 705 aat gct ttg ctc aaa cac ctg gac act caa tac agt gac caa aac aga    2875
Asn Ala Leu Leu Lys His Leu Asp Thr Gln Tyr Ser Asp Gln Asn Arg
        710                 715                 720 ttc aac ctg tgc ttt gaa gaa aga gac ttt gtc cca gga gaa aac cgc    2923
Phe Asn Leu Cys Phe Glu Glu Arg Asp Phe Val Pro Gly Glu Asn Arg
725             730                 735                 740 att gcc aat atc cag gat gcc atc tgg aac agt aga aag atc gtt tgt    2971
Ile Ala Asn Ile Gln Asp Ala Ile Trp Asn Ser Arg Lys Ile Val Cys
                745                 750                 755 ctt gtg agc aga cac ttc ctt aga gat ggc tgg tgc ctt gaa gcc ttc    3019
Leu Val Ser Arg His Phe Leu Arg Asp Gly Trp Cys Leu Glu Ala Phe
                760                 765                 770 agt tat gcc cag ggc agg tgc tta tct gac ctt aac agt gct ctc atc    3067
Ser Tyr Ala Gln Gly Arg Cys Leu Ser Asp Leu Asn Ser Ala Leu Ile
```

```
                    775                 780                 785
atg gtg gtg gtt ggg tcc ttg tcc cag tac cag ttg atg aaa cat caa    3115
Met Val Val Gly Ser Leu Ser Gln Tyr Gln Leu Met Lys His Gln
        790                 795                 800 tcc atc aga ggc ttt gta cag aaa cag cag tat ttg agg tgg cct gag    3163
Ser Ile Arg Gly Phe Val Gln Lys Gln Gln Tyr Leu Arg Trp Pro Glu
805                 810                 815                 820 gat ctc cag gat gtt ggc tgg ttt ctt cat aaa ctc tct caa cag ata    3211
Asp Leu Gln Asp Val Gly Trp Phe Leu His Lys Leu Ser Gln Gln Ile
                825                 830                 835 cta aag aaa gaa aaa gaa aag aag aaa gac aat aac att ccg ttg caa    3259
Leu Lys Lys Glu Lys Glu Lys Lys Lys Asp Asn Asn Ile Pro Leu Gln
            840                 845                 850 act gta gca acc atc tcc taatcaaagg agcaatttcc aacttatctc          3307
Thr Val Ala Thr Ile Ser
            855 aagccacaaa taactcttca ctttgtattt gcaccaagtt atcatttggg ggtcctctct  3367 ggaggttttt tttttctttt tgctactatg aaaacaacat aaatctctca attttcgtat  3427 caaa                                                              3431
```

<210> SEQ ID NO 8
<211> LENGTH: 858
<212> TYPE: PRT
<213> ORGANISM: Homo sapiens

<400> SEQUENCE: 8

```
Met Gly Asp His Leu Asp Leu Leu Gly Val Val Leu Met Ala Gly
  1               5                   10                  15

Pro Val Phe Gly Ile Pro Ser Cys Ser Phe Asp Gly Arg Ile Ala Phe
                 20                  25                  30

Tyr Arg Phe Cys Asn Leu Thr Gln Val Pro Gln Val Leu Asn Thr Thr
             35                  40                  45

Glu Arg Leu Leu Leu Ser Phe Asn Tyr Ile Arg Thr Val Thr Ala Ser
         50                  55                  60

Ser Phe Pro Phe Leu Glu Gln Leu Gln Leu Leu Glu Leu Gly Ser Gln
65                  70                  75                  80

Tyr Thr Pro Leu Thr Ile Asp Lys Glu Ala Phe Arg Asn Leu Pro Asn
                 85                  90                  95

Leu Arg Ile Leu Asp Leu Gly Ser Ser Lys Ile Tyr Phe Leu His Pro
            100                 105                 110

Asp Ala Phe Gln Gly Leu Phe His Leu Phe Glu Leu Arg Leu Tyr Phe
        115                 120                 125

Cys Gly Leu Ser Asp Ala Val Leu Lys Asp Gly Tyr Phe Arg Asn Leu
    130                 135                 140

Lys Ala Leu Thr Arg Leu Asp Leu Ser Lys Asn Gln Ile Arg Ser Leu
145                 150                 155                 160

Tyr Leu His Pro Ser Phe Gly Lys Leu Asn Ser Leu Lys Ser Ile Asp
                165                 170                 175

Phe Ser Ser Asn Gln Ile Phe Leu Val Cys Glu His Glu Leu Glu Pro
            180                 185                 190

Leu Gln Gly Lys Thr Leu Ser Phe Phe Ser Leu Ala Ala Asn Ser Leu
        195                 200                 205

Tyr Ser Arg Val Ser Val Asp Trp Gly Lys Cys Met Asn Pro Phe Arg
    210                 215                 220

Asn Met Val Leu Glu Ile Val Asp Val Ser Gly Asn Gly Trp Thr Val
```

```
            225                 230                 235                 240
Asp Ile Thr Gly Asn Phe Ser Asn Ala Ile Ser Lys Ser Gln Ala Phe
                245                 250                 255
Ser Leu Ile Leu Ala His His Ile Met Gly Ala Gly Phe Gly Phe His
                260                 265                 270
Asn Ile Lys Asp Pro Asp Gln Asn Thr Phe Ala Gly Leu Ala Arg Ser
                275                 280                 285
Ser Val Arg His Leu Asp Leu Ser His Gly Phe Val Phe Ser Leu Asn
                290                 295                 300
Ser Arg Val Phe Glu Thr Leu Lys Asp Leu Lys Val Leu Asn Leu Ala
305                 310                 315                 320
Tyr Asn Lys Ile Asn Lys Ile Ala Asp Glu Ala Phe Tyr Gly Leu Asp
                325                 330                 335
Asn Leu Gln Val Leu Asn Leu Ser Tyr Asn Leu Gly Glu Leu Cys
                340                 345                 350
Ser Ser Asn Phe Tyr Gly Leu Pro Lys Val Ala Tyr Ile Asp Leu Gln
                355                 360                 365
Lys Asn His Ile Ala Ile Ile Gln Asp Gln Thr Phe Lys Phe Leu Glu
                370                 375                 380
Lys Leu Gln Thr Leu Asp Leu Arg Asp Asn Ala Leu Thr Thr Ile His
385                 390                 395                 400
Phe Ile Pro Ser Ile Pro Asp Ile Phe Leu Ser Gly Asn Lys Leu Val
                405                 410                 415
Thr Leu Pro Lys Ile Asn Leu Thr Ala Asn Leu Ile His Leu Ser Glu
                420                 425                 430
Asn Arg Leu Glu Asn Leu Asp Ile Leu Tyr Phe Leu Leu Arg Val Pro
                435                 440                 445
His Leu Gln Ile Leu Ile Leu Asn Gln Asn Arg Phe Ser Ser Cys Ser
                450                 455                 460
Gly Asp Gln Thr Pro Ser Glu Asn Pro Ser Leu Glu Gln Leu Phe Leu
465                 470                 475                 480
Gly Glu Asn Met Leu Gln Leu Ala Trp Glu Thr Glu Leu Cys Trp Asp
                485                 490                 495
Val Phe Glu Gly Leu Ser His Leu Gln Val Leu Tyr Leu Asn His Asn
                500                 505                 510
Tyr Leu Asn Ser Leu Pro Pro Gly Val Phe Ser His Leu Thr Ala Leu
                515                 520                 525
Arg Gly Leu Ser Leu Asn Ser Asn Arg Leu Thr Val Leu Ser His Asn
                530                 535                 540
Asp Leu Pro Ala Asn Leu Glu Ile Leu Asp Ile Ser Arg Asn Gln Leu
545                 550                 555                 560
Leu Ala Pro Asn Pro Asp Val Phe Val Ser Leu Ser Val Leu Asp Ile
                565                 570                 575
Thr His Asn Lys Phe Ile Cys Glu Cys Glu Leu Ser Thr Phe Ile Asn
                580                 585                 590
Trp Leu Asn His Thr Asn Val Thr Ile Ala Gly Pro Pro Ala Asp Ile
                595                 600                 605
Tyr Cys Val Tyr Pro Asp Ser Leu Ser Gly Val Ser Leu Phe Ser Leu
                610                 615                 620
Ser Thr Glu Gly Cys Asp Glu Glu Val Leu Lys Ser Leu Lys Phe
625                 630                 635                 640
Ser Leu Phe Ile Val Cys Thr Val Thr Leu Thr Leu Phe Leu Met Thr
                645                 650                 655
```

-continued

```
Ile Leu Thr Val Thr Lys Phe Arg Gly Phe Cys Phe Ile Cys Tyr Lys
            660                 665                 670
Thr Ala Gln Arg Leu Val Phe Lys Asp His Pro Gln Gly Thr Glu Pro
        675                 680                 685
Asp Met Tyr Lys Tyr Asp Ala Tyr Leu Cys Phe Ser Ser Lys Asp Phe
    690                 695                 700
Thr Trp Val Gln Asn Ala Leu Leu Lys His Leu Asp Thr Gln Tyr Ser
705                 710                 715                 720
Asp Gln Asn Arg Phe Asn Leu Cys Phe Glu Glu Arg Asp Phe Val Pro
                725                 730                 735
Gly Glu Asn Arg Ile Ala Asn Ile Gln Asp Ala Ile Trp Asn Ser Arg
            740                 745                 750
Lys Ile Val Cys Leu Val Ser Arg His Phe Leu Arg Asp Gly Trp Cys
        755                 760                 765
Leu Glu Ala Phe Ser Tyr Ala Gln Gly Arg Cys Leu Ser Asp Leu Asn
    770                 775                 780
Ser Ala Leu Ile Met Val Val Gly Ser Leu Ser Gln Tyr Gln Leu
785                 790                 795                 800
Met Lys His Gln Ser Ile Arg Gly Phe Val Gln Lys Gln Tyr Leu
                805                 810                 815
Arg Trp Pro Glu Asp Leu Gln Asp Val Gly Trp Phe Leu His Lys Leu
            820                 825                 830
Ser Gln Gln Ile Leu Lys Lys Glu Lys Lys Lys Asp Asn Asn
        835                 840                 845
Ile Pro Leu Gln Thr Val Ala Thr Ile Ser
    850                 855

<210> SEQ ID NO 9
<211> LENGTH: 1839
<212> TYPE: DNA
<213> ORGANISM: Homo sapiens
<220> FEATURE:
<221> NAME/KEY: CDS
<222> LOCATION: (1)...(1839)

<400> SEQUENCE: 9 atg tgc cga gcc atc tct ctt agg cgc ttg ctg ctg ctg ctg ctg cag    48
Met Cys Arg Ala Ile Ser Leu Arg Arg Leu Leu Leu Leu Leu Leu Gln
  1               5                  10                  15 ctg tca caa ctc cta gct gtc act caa ggg aag acg ctg gtg ctg ggg    96
Leu Ser Gln Leu Leu Ala Val Thr Gln Gly Lys Thr Leu Val Leu Gly
             20                  25                  30 aag gaa ggg gaa tca gca gaa ctg ccc tgc gag agt tcc cag aag aag   144
Lys Glu Gly Glu Ser Ala Glu Leu Pro Cys Glu Ser Ser Gln Lys Lys
         35                  40                  45 atc aca gtc ttc acc tgg aag ttc tct gac cag agg aag att ctg ggg   192
Ile Thr Val Phe Thr Trp Lys Phe Ser Asp Gln Arg Lys Ile Leu Gly
     50                  55                  60 cag cat ggc aaa ggt gta tta att aga gga ggt tcg cct tcg cag ttt   240
Gln His Gly Lys Gly Val Leu Ile Arg Gly Gly Ser Pro Ser Gln Phe
 65                  70                  75                  80 gat cgt ttt gat tcc aaa aaa ggg gca tgg gag aaa gga tcg ttt cct   288
Asp Arg Phe Asp Ser Lys Lys Gly Ala Trp Glu Lys Gly Ser Phe Pro
                 85                  90                  95 ctc atc atc aat aaa ctt aag atg gaa gac tct cag act tat atc tgt   336
Leu Ile Ile Asn Lys Leu Lys Met Glu Asp Ser Gln Thr Tyr Ile Cys
            100                 105                 110
```

```
gag ctg gag aac agg aaa gag gag gtg gag ttg tgg gtg ttc aaa gtg      384
Glu Leu Glu Asn Arg Lys Glu Glu Val Glu Leu Trp Val Phe Lys Val
        115                 120                 125 acc ttc agt ccg ggt acc agc ctg ttg caa ggg cag agc ctg acc ctg      432
Thr Phe Ser Pro Gly Thr Ser Leu Leu Gln Gly Gln Ser Leu Thr Leu
    130                 135                 140 acc ttg gat agc aac tct aag gtc tct aac ccc ttg aca gag tgc aaa      480
Thr Leu Asp Ser Asn Ser Lys Val Ser Asn Pro Leu Thr Glu Cys Lys
145                 150                 155                 160 cac aaa aag ggt aaa gtt gtc agt ggt tcc aaa gtt ctc tcc atg tcc      528
His Lys Lys Gly Lys Val Val Ser Gly Ser Lys Val Leu Ser Met Ser
                165                 170                 175 aac cta agg gtt cag gac agc gac ttc tgg aac tgc acc gtg acc ctg      576
Asn Leu Arg Val Gln Asp Ser Asp Phe Trp Asn Cys Thr Val Thr Leu
            180                 185                 190 gac cag aaa aag aac tgg ttc ggc atg aca ctc tca gtg ctg ggt ttt      624
Asp Gln Lys Lys Asn Trp Phe Gly Met Thr Leu Ser Val Leu Gly Phe
        195                 200                 205 cag agc aca gct atc acg gcc tat aag agt gag gga gag tca gcg gag      672
Gln Ser Thr Ala Ile Thr Ala Tyr Lys Ser Glu Gly Glu Ser Ala Glu
    210                 215                 220 ttc tcc ttc cca ctc aac ttt gca gag gaa aac ggg tgg gga gag ctg      720
Phe Ser Phe Pro Leu Asn Phe Ala Glu Glu Asn Gly Trp Gly Glu Leu
225                 230                 235                 240 atg tgg aag gca gag aag gat tct ttc ttc cag ccc tgg atc tcc ttc      768
Met Trp Lys Ala Glu Lys Asp Ser Phe Phe Gln Pro Trp Ile Ser Phe
                245                 250                 255 tcc ata aag aac aaa gag gtg tcc gta caa aag tcc acc aaa gac ctc      816
Ser Ile Lys Asn Lys Glu Val Ser Val Gln Lys Ser Thr Lys Asp Leu
            260                 265                 270 aag ctc cag ctg aag gaa acg ctc cca ctc acc ctc aag ata ccc cag      864
Lys Leu Gln Leu Lys Glu Thr Leu Pro Leu Thr Leu Lys Ile Pro Gln
        275                 280                 285 gtc tcg ctt cag ttt gct ggt tct ggc aac ctg act ctg act ctg gac      912
Val Ser Leu Gln Phe Ala Gly Ser Gly Asn Leu Thr Leu Thr Leu Asp
    290                 295                 300 aaa ggg aca ctg cat cag gaa gtg aac ctg gtg gtg atg aaa gtg gct      960
Lys Gly Thr Leu His Gln Glu Val Asn Leu Val Val Met Lys Val Ala
305                 310                 315                 320 cag ctc aac aat act ttg acc tgt gag gtg atg gga cct acc tct ccc     1008
Gln Leu Asn Asn Thr Leu Thr Cys Glu Val Met Gly Pro Thr Ser Pro
                325                 330                 335 aag atg aga ctg acc ctg aag cag gag aac cag gag gcc agg gtc tct     1056
Lys Met Arg Leu Thr Leu Lys Gln Glu Asn Gln Glu Ala Arg Val Ser
            340                 345                 350 gag gag cag aaa gta gtt caa gtg gtg gcc cct gag aca ggg ctg tgg     1104
Glu Glu Gln Lys Val Val Gln Val Val Ala Pro Glu Thr Gly Leu Trp
        355                 360                 365 cag tgt cta ctg agt gaa ggt gat aag gtc aag atg gac tcc agg atc     1152
Gln Cys Leu Leu Ser Glu Gly Asp Lys Val Lys Met Asp Ser Arg Ile
    370                 375                 380 cag gtt tta tcc aga ggg gtg tac cag ttc tcc ctt ttc att gta tgc     1200
Gln Val Leu Ser Arg Gly Val Tyr Gln Phe Ser Leu Phe Ile Val Cys
385                 390                 395                 400 act gtc act ctg act ctg ttc ctc atg acc atc ctc aca gtc aca aag     1248
Thr Val Thr Leu Thr Leu Phe Leu Met Thr Ile Leu Thr Val Thr Lys
                405                 410                 415 ttc cgg ggc ttc tgt ttt atc tgt tat aag aca gcc cag aga ctg gtg     1296
Phe Arg Gly Phe Cys Phe Ile Cys Tyr Lys Thr Ala Gln Arg Leu Val
            420                 425                 430
```

```
ttc aag gac cat ccc cag ggc aca gaa cct gat atg tac aaa tat gat       1344
Phe Lys Asp His Pro Gln Gly Thr Glu Pro Asp Met Tyr Lys Tyr Asp
        435                 440                 445 gcc tat ttg tgc ttc agc agc aaa gac ttc aca tgg gtg cag aat gct       1392
Ala Tyr Leu Cys Phe Ser Ser Lys Asp Phe Thr Trp Val Gln Asn Ala
    450                 455                 460 ttg ctc aaa cac ctg gac act caa tac agt gac caa aac aga ttc aac       1440
Leu Leu Lys His Leu Asp Thr Gln Tyr Ser Asp Gln Asn Arg Phe Asn
465                 470                 475                 480 ctg tgc ttt gaa gaa aga gac ttt gtc cca gga gaa aac cgc att gcc       1488
Leu Cys Phe Glu Glu Arg Asp Phe Val Pro Gly Glu Asn Arg Ile Ala
                485                 490                 495 aat atc cag gat gcc atc tgg aac agt aga aag atc gtt tgt ctt gtg       1536
Asn Ile Gln Asp Ala Ile Trp Asn Ser Arg Lys Ile Val Cys Leu Val
            500                 505                 510 agc aga cac ttc ctt aga gat ggc tgg tgc ctt gaa gcc ttc agt tat       1584
Ser Arg His Phe Leu Arg Asp Gly Trp Cys Leu Glu Ala Phe Ser Tyr
        515                 520                 525 gcc cag ggc agg tgc tta tct gac ctt aac agt gct ctc atc atg gtg       1632
Ala Gln Gly Arg Cys Leu Ser Asp Leu Asn Ser Ala Leu Ile Met Val
    530                 535                 540 gtg gtt ggg tcc ttg tcc cag tac cag ttg atg aaa cat caa tcc atc       1680
Val Val Gly Ser Leu Ser Gln Tyr Gln Leu Met Lys His Gln Ser Ile
545                 550                 555                 560 aga ggc ttt gta cag aaa cag cag tat ttg agg tgg cct gag gat ctc       1728
Arg Gly Phe Val Gln Lys Gln Gln Tyr Leu Arg Trp Pro Glu Asp Leu
                565                 570                 575 cag gat gtt ggc tgg ttt ctt cat aaa ctc tct caa cag ata cta aag       1776
Gln Asp Val Gly Trp Phe Leu His Lys Leu Ser Gln Gln Ile Leu Lys
            580                 585                 590 aaa gaa aaa gaa aag aag aaa gac aat aac att ccg ttg caa act gta       1824
Lys Glu Lys Glu Lys Lys Lys Asp Asn Asn Ile Pro Leu Gln Thr Val
        595                 600                 605 gca acc atc tcc taa                                                   1839
Ala Thr Ile Ser *
    610

<210> SEQ ID NO 10
<211> LENGTH: 612
<212> TYPE: PRT
<213> ORGANISM: Homo sapiens

<400> SEQUENCE: 10

Met Cys Arg Ala Ile Ser Leu Arg Arg Leu Leu Leu Leu Leu Leu Gln
1               5                   10                  15

Leu Ser Gln Leu Leu Ala Val Thr Gln Gly Lys Thr Leu Val Leu Gly
            20                  25                  30

Lys Glu Gly Glu Ser Ala Glu Leu Pro Cys Glu Ser Ser Gln Lys Lys
        35                  40                  45

Ile Thr Val Phe Thr Trp Lys Phe Ser Asp Gln Arg Lys Ile Leu Gly
    50                  55                  60

Gln His Gly Lys Gly Val Leu Ile Arg Gly Gly Ser Pro Ser Gln Phe
65                  70                  75                  80

Asp Arg Phe Asp Ser Lys Lys Gly Ala Trp Glu Lys Gly Ser Phe Pro
                85                  90                  95

Leu Ile Ile Asn Lys Leu Lys Met Glu Asp Ser Gln Thr Tyr Ile Cys
            100                 105                 110

Glu Leu Glu Asn Arg Lys Glu Glu Val Glu Leu Trp Val Phe Lys Val
```

```
                115                 120                 125
Thr Phe Ser Pro Gly Thr Ser Leu Leu Gln Gly Gln Ser Leu Thr Leu
130                 135                 140
Thr Leu Asp Ser Asn Ser Lys Val Ser Asn Pro Leu Thr Glu Cys Lys
145                 150                 155                 160
His Lys Lys Gly Lys Val Val Ser Gly Ser Lys Val Leu Ser Met Ser
                165                 170                 175
Asn Leu Arg Val Gln Asp Ser Asp Phe Trp Asn Cys Thr Val Thr Leu
            180                 185                 190
Asp Gln Lys Lys Asn Trp Phe Gly Met Thr Leu Ser Val Leu Gly Phe
        195                 200                 205
Gln Ser Thr Ala Ile Thr Ala Tyr Lys Ser Glu Gly Glu Ser Ala Glu
210                 215                 220
Phe Ser Phe Pro Leu Asn Phe Ala Glu Glu Asn Gly Trp Gly Glu Leu
225                 230                 235                 240
Met Trp Lys Ala Glu Lys Asp Ser Phe Phe Gln Pro Trp Ile Ser Phe
                245                 250                 255
Ser Ile Lys Asn Lys Glu Val Ser Val Gln Lys Ser Thr Lys Asp Leu
            260                 265                 270
Lys Leu Gln Leu Lys Glu Thr Leu Pro Leu Thr Leu Lys Ile Pro Gln
        275                 280                 285
Val Ser Leu Gln Phe Ala Gly Ser Gly Asn Leu Thr Leu Thr Leu Asp
290                 295                 300
Lys Gly Thr Leu His Gln Glu Val Asn Leu Val Val Met Lys Val Ala
305                 310                 315                 320
Gln Leu Asn Asn Thr Leu Thr Cys Glu Val Met Gly Pro Thr Ser Pro
                325                 330                 335
Lys Met Arg Leu Thr Leu Lys Gln Glu Asn Gln Glu Ala Arg Val Ser
            340                 345                 350
Glu Glu Gln Lys Val Val Gln Val Val Ala Pro Glu Thr Gly Leu Trp
        355                 360                 365
Gln Cys Leu Leu Ser Glu Gly Asp Lys Val Lys Met Asp Ser Arg Ile
370                 375                 380
Gln Val Leu Ser Arg Gly Val Tyr Gln Phe Ser Leu Phe Ile Val Cys
385                 390                 395                 400
Thr Val Thr Leu Thr Leu Phe Leu Met Thr Ile Leu Thr Val Thr Lys
                405                 410                 415
Phe Arg Gly Phe Cys Phe Ile Cys Tyr Lys Thr Ala Gln Arg Leu Val
            420                 425                 430
Phe Lys Asp His Pro Gln Gly Thr Glu Pro Asp Met Tyr Lys Tyr Asp
        435                 440                 445
Ala Tyr Leu Cys Phe Ser Ser Lys Asp Phe Thr Trp Val Gln Asn Ala
450                 455                 460
Leu Leu Lys His Leu Asp Thr Gln Tyr Ser Asp Gln Asn Arg Phe Asn
465                 470                 475                 480
Leu Cys Phe Glu Glu Arg Asp Phe Val Pro Gly Glu Asn Arg Ile Ala
                485                 490                 495
Asn Ile Gln Asp Ala Ile Trp Asn Ser Arg Lys Ile Val Cys Leu Val
            500                 505                 510
Ser Arg His Phe Leu Arg Asp Gly Trp Cys Leu Glu Ala Phe Ser Tyr
        515                 520                 525
Ala Gln Gly Arg Cys Leu Ser Asp Leu Asn Ser Ala Leu Ile Met Val
530                 535                 540
```

```
Val Val Gly Ser Leu Ser Gln Tyr Gln Leu Met Lys His Gln Ser Ile
545                 550                 555                 560

Arg Gly Phe Val Gln Lys Gln Tyr Leu Arg Trp Pro Glu Asp Leu
            565                 570                 575

Gln Asp Val Gly Trp Phe Leu His Lys Leu Ser Gln Gln Ile Leu Lys
        580                 585                 590

Lys Glu Lys Glu Lys Lys Lys Asp Asn Asn Ile Pro Leu Gln Thr Val
        595                 600                 605

Ala Thr Ile Ser
        610

<210> SEQ ID NO 11
<211> LENGTH: 572
<212> TYPE: PRT
<213> ORGANISM: C. jejuni

<400> SEQUENCE: 11

Met Gly Phe Arg Ile Asn Thr Asn Val Ala Ala Leu Asn Ala Lys Ala
1               5                   10                  15

Asn Ala Asp Leu Asn Ser Lys Ser Leu Asp Ala Ser Leu Ser Arg Leu
            20                  25                  30

Ser Ser Gly Leu Arg Ile Asn Ser Ala Ala Asp Asp Ala Ser Gly Met
        35                  40                  45

Ala Ile Ala Asp Thr Leu Arg Ser Gln Ala Asn Thr Leu Gly Gln Ala
50                  55                  60

Ile Ser Asn Gly Asn Asp Ala Ile Gly Ile Leu Gln Thr Ala Asp Lys
65                  70                  75                  80

Ala Met Asp Glu Gln Leu Lys Ile Leu Asp Thr Ile Lys Thr Lys Ala
                85                  90                  95

Thr Gln Ala Ala Gln Asp Gly Gln Ser Leu Lys Thr Arg Thr Met Leu
            100                 105                 110

Gln Ala Asp Ile Asn Arg Leu Met Glu Glu Leu Asp Asn Ile Ala Asn
        115                 120                 125

Thr Thr Ser Phe Asn Gly Lys Gln Leu Leu Ser Gly Asn Phe Ile Asn
130                 135                 140

Gln Glu Phe Gln Ile Gly Ala Ser Ser Asn Gln Thr Val Lys Ala Thr
145                 150                 155                 160

Ile Gly Ala Thr Gln Ser Ser Lys Ile Gly Leu Thr Arg Phe Glu Thr
                165                 170                 175

Gly Gly Arg Ile Ser Thr Ser Gly Glu Val Gln Phe Thr Leu Lys Asn
            180                 185                 190

Tyr Asn Gly Ile Asp Asp Phe Gln Phe Gln Lys Val Val Ile Ser Thr
        195                 200                 205

Ser Val Gly Thr Gly Leu Gly Ala Leu Ala Asp Glu Ile Asn Lys Asn
210                 215                 220

Ala Asp Lys Thr Gly Val Arg Ala Thr Phe Thr Val Glu Thr Arg Gly
225                 230                 235                 240

Ile Ala Ala Val Arg Ala Gly Ala Thr Ser Asp Thr Phe Ala Ile Asn
                245                 250                 255

Gly Val Lys Ile Gly Lys Val Asp Tyr Lys Asp Gly Asp Ala Asn Gly
            260                 265                 270

Ala Leu Val Ala Ala Ile Asn Ser Val Lys Asp Thr Thr Gly Val Glu
        275                 280                 285

Ala Ser Ile Asp Ala Asn Gly Gln Leu Leu Leu Thr Ser Arg Glu Gly
```

```
                290                 295                 300

Arg Gly Ile Lys Ile Asp Gly Asn Ile Gly Gly Ala Phe Ile Asn
305                 310                 315                 320

Ala Asp Met Lys Glu Asn Tyr Gly Arg Leu Ser Leu Val Lys Asn Asp
                325                 330                 335

Gly Lys Asp Ile Leu Ile Ser Gly Ser Asn Leu Ser Ser Ala Gly Phe
                340                 345                 350

Gly Ala Thr Gln Phe Ile Ser Gln Ala Ser Val Ser Leu Arg Glu Ser
                355                 360                 365

Lys Gly Gln Ile Asp Ala Asn Ile Ala Asp Ala Met Gly Phe Gly Ser
370                 375                 380

Ala Asn Lys Gly Val Val Leu Gly Gly Tyr Ser Ser Val Ser Ala Tyr
385                 390                 395                 400

Met Ser Ser Ala Gly Ser Gly Phe Ser Ser Gly Ser Tyr Ser Val
                405                 410                 415

Gly Ser Gly Lys Asn Tyr Ser Thr Gly Phe Ala Asn Ala Ile Ala Ile
                420                 425                 430

Ser Ala Ala Ser Gln Leu Ser Thr Val Tyr Asn Val Ser Ala Gly Ser
                435                 440                 445

Gly Phe Ser Ser Gly Ser Thr Leu Ser Gln Phe Ala Thr Met Lys Thr
450                 455                 460

Thr Ala Phe Gly Val Lys Asp Glu Thr Ala Gly Val Thr Thr Leu Lys
465                 470                 475                 480

Gly Ala Met Ala Val Met Asp Ile Ala Glu Thr Ala Thr Asn Leu
                485                 490                 495

Asp Gln Ile Arg Ala Asp Ile Gly Ser Val Gln Asn Gln Val Thr Ser
                500                 505                 510

Thr Ile Asn Asn Ile Thr Val Thr Gln Val Asn Val Lys Ala Ala Glu
                515                 520                 525

Ser Gln Ile Arg Asp Val Asp Phe Ala Ala Glu Ser Ala Asn Tyr Ser
                530                 535                 540

Lys Ala Asn Ile Leu Ala Gln Ser Gly Ser Tyr Ala Met Ala Gln Ala
545                 550                 555                 560

Asn Ser Val His Gln Asn Val Leu Arg Leu Leu Gln
                565                 570

<210> SEQ ID NO 12
<211> LENGTH: 510
<212> TYPE: PRT
<213> ORGANISM: H. pylori

<400> SEQUENCE: 12

Met Ala Phe Gln Val Asn Thr Asn Ile Asn Ala Met Asn Ala His Val
1               5                   10                  15

Gln Ser Ala Leu Thr Gln Asn Ala Leu Lys Thr Ser Leu Glu Arg Leu
                20                  25                  30

Ser Ser Gly Leu Arg Ile Asn Lys Ala Ala Asp Asp Ala Ser Gly Met
            35                  40                  45

Thr Val Ala Asp Ser Leu Arg Ser Gln Ala Ser Ser Leu Gly Gln Ala
50              55                  60

Ile Ala Asn Thr Asn Asp Gly Met Gly Ile Ile Gln Val Ala Asp Lys
65              70                  75                  80

Ala Met Asp Glu Gln Leu Lys Ile Leu Asp Thr Val Lys Val Lys Ala
                85                  90                  95
```

```
Thr Gln Ala Ala Gln Asp Gly Gln Thr Thr Glu Ser Arg Lys Ala Ile
            100                 105                 110
Gln Ser Asp Ile Val Arg Leu Ile Gln Gly Leu Asp Asn Ile Gly Asn
        115                 120                 125
Thr Thr Thr Tyr Asn Gly Gln Ala Leu Leu Ser Gly Gln Phe Thr Asn
    130                 135                 140
Lys Glu Phe Gln Val Gly Ala Tyr Ser Asn Gln Ser Ile Lys Ala Ser
145                 150                 155                 160
Ile Gly Ser Thr Thr Ser Asp Lys Ile Gly Gln Val Arg Ile Ala Thr
                165                 170                 175
Gly Ala Leu Ile Thr Ala Ser Gly Asp Ile Ser Leu Thr Phe Lys Gln
            180                 185                 190
Val Asp Gly Val Asn Asp Val Thr Leu Glu Ser Val Lys Val Ser Ser
        195                 200                 205
Ser Ala Gly Thr Gly Ile Gly Val Leu Ala Glu Val Ile Asn Lys Asn
    210                 215                 220
Ser Asn Arg Thr Gly Val Lys Ala Tyr Ala Ser Val Ile Thr Thr Ser
225                 230                 235                 240
Asp Val Ala Val Gln Ser Gly Ser Leu Ser Asn Leu Thr Leu Asn Gly
                245                 250                 255
Ile His Leu Gly Asn Ile Ala Asp Ile Lys Lys Asn Asp Ser Asp Gly
            260                 265                 270
Arg Leu Val Ala Ala Ile Asn Ala Val Thr Ser Glu Thr Gly Val Glu
        275                 280                 285
Ala Tyr Thr Asp Gln Lys Gly Arg Leu Asn Leu Arg Ser Ile Asp Gly
    290                 295                 300
Arg Gly Ile Glu Ile Lys Thr Asp Ser Val Ser Asn Gly Pro Ser Ala
305                 310                 315                 320
Leu Thr Met Val Asn Gly Gly Gln Asp Leu Thr Lys Gly Ser Thr Asn
                325                 330                 335
Tyr Gly Arg Leu Ser Leu Thr Arg Leu Asp Ala Lys Ser Ile Asn Val
            340                 345                 350
Val Ser Ala Ser Asp Ser Gln His Leu Gly Phe Thr Ala Ile Gly Phe
        355                 360                 365
Gly Glu Ser Gln Val Ala Glu Thr Thr Val Asn Leu Arg Asp Val Thr
    370                 375                 380
Gly Asn Phe Asn Ala Asn Val Lys Ser Ala Ser Gly Ala Asn Tyr Asn
385                 390                 395                 400
Ala Val Ile Ala Ser Gly Asn Gln Ser Leu Gly Ser Gly Val Thr Thr
                405                 410                 415
Leu Arg Gly Ala Met Val Val Ile Asp Ile Ala Glu Ser Ala Met Lys
            420                 425                 430
Met Leu Asp Lys Val Arg Ser Asp Leu Gly Ser Val Gln Asn Gln Met
        435                 440                 445
Ile Ser Thr Val Asn Asn Ile Ser Ile Thr Gln Val Asn Val Lys Ala
    450                 455                 460
Ala Glu Ser Gln Ile Arg Asp Val Asp Phe Ala Glu Glu Ser Ala Asn
465                 470                 475                 480
Phe Asn Lys Asn Asn Ile Leu Ala Gln Ser Gly Ser Tyr Ala Met Ser
                485                 490                 495
Gln Ala Asn Thr Val Gln Gln Asn Ile Leu Arg Leu Leu Thr
            500                 505                 510
```

```
<210> SEQ ID NO 13
<211> LENGTH: 379
<212> TYPE: PRT
<213> ORGANISM: V. cholerae

<400> SEQUENCE: 13

Met Thr Ile Asn Val Asn Thr Asn Val Ser Ala Met Thr Ala Gln Arg
 1               5                  10                  15

Tyr Leu Thr Lys Ala Thr Gly Glu Leu Asn Thr Ser Met Glu Arg Leu
             20                  25                  30

Ser Ser Gly Asn Arg Ile Asn Ser Ala Lys Asp Asp Ala Ala Gly Leu
         35                  40                  45

Gln Ile Ser Asn Arg Leu Thr Ala Gln Ser Arg Gly Leu Asp Val Ala
     50                  55                  60

Met Arg Asn Ala Asn Asp Gly Ile Ser Ile Ala Gln Thr Ala Glu Gly
 65                  70                  75                  80

Ala Met Asn Glu Ser Thr Ser Ile Leu Gln Arg Met Arg Asp Leu Ala
                 85                  90                  95

Leu Gln Ser Ala Asn Gly Thr Asn Ser Ala Ser Glu Arg Gln Ala Leu
            100                 105                 110

Asn Glu Glu Ser Val Ala Leu Gln Asp Glu Leu Asn Arg Ile Ala Glu
        115                 120                 125

Thr Thr Ser Phe Gly Gly Arg Lys Leu Leu Asn Gly Ser Phe Gly Glu
    130                 135                 140

Ala Ser Phe Gln Ile Gly Ser Ser Gly Glu Ala Ile Ile Met Gly
145                 150                 155                 160

Leu Thr Ser Val Arg Ala Asp Asp Phe Arg Met Gly Gly Gln Ser Phe
                165                 170                 175

Ile Ala Glu Gln Pro Lys Thr Lys Glu Trp Gly Val Pro Pro Thr Ala
            180                 185                 190

Arg Asp Leu Lys Phe Glu Phe Thr Lys Lys Asp Gly Glu Ala Val Val
        195                 200                 205

Leu Asp Ile Ile Ala Lys Asp Gly Asp Ile Glu Glu Leu Ala Thr
    210                 215                 220

Tyr Ile Asn Gly Gln Thr Asp Leu Phe Lys Ala Ser Val Asp Gln Glu
225                 230                 235                 240

Gly Lys Leu Gln Ile Phe Val Ala Glu Pro Asn Ile Glu Gly Asn Phe
                245                 250                 255

Asn Ile Ser Gly Gly Leu Ala Thr Glu Leu Gly Leu Asn Gly Gly Pro
            260                 265                 270

Gly Val Lys Thr Thr Val Gln Asp Ile Asp Ile Thr Ser Val Gly Gly
        275                 280                 285

Ser Gln Asn Ala Val Gly Ile Ile Asp Ala Ala Leu Lys Tyr Val Asp
    290                 295                 300

Ser Gln Arg Ala Asp Leu Gly Ala Lys Gln Asn Arg Leu Ser His Ser
305                 310                 315                 320

Ile Ser Asn Leu Ser Asn Ile Gln Glu Asn Val Glu Ala Ser Lys Ser
                325                 330                 335

Arg Ile Lys Asp Thr Asp Phe Ala Lys Glu Thr Thr Gln Leu Thr Lys
            340                 345                 350

Ser Gln Ile Leu Gln Gln Ala Gly Thr Ser Ile Leu Ala Gln Ala Lys
        355                 360                 365

Gln Leu Pro Asn Ser Ala Ile Ser Leu Leu Gln
    370                 375
```

<210> SEQ ID NO 14
<211> LENGTH: 394
<212> TYPE: PRT
<213> ORGANISM: P. aeruginosa

<400> SEQUENCE: 14

```
Met Ala Leu Thr Val Asn Thr Asn Ile Ala Ser Leu Asn Thr Gln Arg
 1               5                  10                  15

Asn Leu Asn Asn Ser Ser Ala Ser Leu Asn Thr Ser Leu Gln Arg Leu
             20                  25                  30

Ser Thr Gly Ser Arg Ile Asn Ser Ala Lys Asp Asp Ala Ala Gly Leu
         35                  40                  45

Gln Ile Ala Asn Arg Leu Thr Ser Gln Val Asn Gly Leu Asn Val Ala
     50                  55                  60

Thr Lys Asn Ala Asn Asp Gly Ile Ser Leu Ala Gln Thr Ala Glu Gly
 65                  70                  75                  80

Ala Leu Gln Gln Ser Thr Asn Ile Leu Gln Arg Met Arg Asp Leu Ser
                 85                  90                  95

Leu Gln Ser Ala Asn Gly Ser Asn Ser Asp Ser Glu Arg Thr Ala Leu
            100                 105                 110

Asn Gly Glu Ala Lys Gln Leu Gln Lys Glu Leu Asp Arg Ile Ser Asn
        115                 120                 125

Thr Thr Thr Phe Gly Gly Arg Lys Leu Leu Asp Gly Ser Phe Gly Val
    130                 135                 140

Ala Ser Phe Gln Val Gly Ser Ala Ala Asn Glu Ile Ile Ser Val Gly
145                 150                 155                 160

Ile Asp Glu Met Ser Ala Glu Ser Leu Asn Gly Thr Tyr Phe Lys Ala
                165                 170                 175

Asp Gly Gly Gly Ala Val Thr Ala Thr Ala Ser Gly Thr Val Asp
            180                 185                 190

Ile Ala Ile Gly Ile Thr Gly Gly Ser Ala Val Asn Val Lys Val Asp
        195                 200                 205

Met Lys Gly Asn Glu Thr Ala Glu Gln Ala Ala Lys Ile Ala Ala
    210                 215                 220

Ala Val Asn Asp Ala Asn Val Gly Ile Gly Ala Phe Ser Asp Gly Asp
225                 230                 235                 240

Thr Ile Ser Tyr Val Ser Lys Ala Gly Lys Asp Gly Ser Gly Ala Ile
                245                 250                 255

Thr Ser Ala Val Ser Gly Val Val Ile Ala Asp Thr Gly Ser Thr Gly
            260                 265                 270

Val Gly Thr Ala Ala Gly Val Ala Pro Ser Ala Thr Ala Phe Ala Lys
        275                 280                 285

Thr Asn Asp Thr Val Ala Lys Ile Asp Ile Ser Thr Ala Lys Ala Leu
    290                 295                 300

Ser Arg Arg Ala Gly Asp Arg Thr Thr Ala Ile Lys Gln Ile Asp Ala
305                 310                 315                 320

Ser Val Pro Thr Ser Val Ala Val Gln Asn Arg Phe Asp Asn Thr Ile
                325                 330                 335

Asn Asn Leu Lys Asn Ile Gly Glu Asn Val Ser Ala Ala Arg Gly Arg
            340                 345                 350

Ile Glu Asp Thr Asp Phe Ala Ala Glu Thr Ala Asn Leu Thr Lys Asn
        355                 360                 365

Gln Val Leu Gln Gln Ala Gly Thr Ala Ile Leu Ala Gln Ala Asn Gln
    370                 375                 380
```

```
Leu Pro Gln Ser Val Leu Ser Leu Arg
385                 390

<210> SEQ ID NO 15
<211> LENGTH: 170
<212> TYPE: PRT
<213> ORGANISM: R. sphaeroides

<400> SEQUENCE: 15

Met Thr Thr Ile Asn Thr Asn Ile Gly Ala Ile Ala Gln Ala Asn
  1               5                  10                  15

Met Thr Lys Val Asn Asp Gln Phe Asn Thr Ala Met Thr Arg Leu Ser
             20                  25                  30

Thr Gly Leu Arg Ile Asn Ala Ala Lys Asp Asp Ala Ala Gly Met Ala
         35                  40                  45

Ile Gly Glu Lys Met Thr Ala Gln Val Met Gly Leu Asn Gln Ala Ile
     50                  55                  60

Arg Asn Ala Gln Asp Gly Lys Asn Leu Val Asp Thr Thr Glu Gly Ala
 65                  70                  75                  80

His Val Glu Val Ser Ser Met Leu Gln Arg Leu Arg Glu Leu Ala Val
                 85                  90                  95

Gln Ser Ser Asn Asp Thr Asn Thr Ala Ala Asp Arg Gly Ser Leu Ala
            100                 105                 110

Ala Glu Gly Lys Gln Leu Ile Ala Glu Ile Asn Arg Val Ala Glu Ser
            115                 120                 125

Thr Thr Phe Asn Gly Met Lys Val Leu Asp Gly Ser Phe Thr Gly Lys
        130                 135                 140

Gln Leu Gln Ile Gly Ala Asp Ser Gly Gln Thr Met Ala Ile Asn Val
145                 150                 155                 160

Asp Ser Ala Ala Ala Thr Asp Ile Gly Ala
                165                 170

<210> SEQ ID NO 16
<211> LENGTH: 365
<212> TYPE: PRT
<213> ORGANISM: P. mirabilis1

<400> SEQUENCE: 16

Met Ala Gln Val Ile Asn Thr Asn Tyr Leu Ser Leu Val Thr Gln Asn
  1               5                  10                  15

Asn Leu Asn Lys Ser Gln Gly Thr Leu Gly Ser Ala Ile Glu Arg Leu
             20                  25                  30

Ser Ser Gly Leu Arg Ile Asn Ser Ala Lys Asp Asp Ala Ala Gly Gln
         35                  40                  45

Ala Ile Ala Asn Arg Phe Thr Ser Asn Val Asn Gly Leu Thr Gln Ala
     50                  55                  60

Ser Arg Asn Ala Asn Asp Gly Ile Ser Ile Ala Gln Thr Thr Glu Gly
 65                  70                  75                  80

Ala Leu Asn Glu Ile Asn Asn Asn Leu Gln Arg Ile Arg Glu Leu Thr
                 85                  90                  95

Val Gln Ala Lys Asn Gly Thr Asn Ser Asn Ser Asp Ile Thr Ser Ile
            100                 105                 110

Gln Asn Glu Val Lys Asn Val Leu Asp Glu Ile Asn Arg Ile Ser Glu
            115                 120                 125

Gln Thr Gln Phe Asn Gly Val Lys Val Leu Ser Gly Glu Lys Ser Glu
        130                 135                 140
```

```
Met Val Ile Gln Val Gly Thr Asn Asp Asn Glu Thr Ile Lys Phe Asn
145                 150                 155                 160

Leu Asp Lys Val Asp Asn Thr Leu Gly Val Ala Ser Asp Lys Leu
                165                 170                 175

Phe Asp Thr Lys Thr Glu Lys Lys Gly Val Thr Ala Ala Gly Ala Gly
            180                 185                 190

Val Thr Asp Ala Lys Lys Ile Asn Ala Ala Thr Leu Asp Met Met
        195                 200                 205

Val Ser Leu Val Lys Glu Phe Asn Leu Asp Gly Lys Pro Val Thr Asp
210                 215                 220

Lys Phe Ile Val Thr Lys Gly Lys Asp Tyr Val Ala Thr Lys Ser
225                 230                 235                 240

Asp Phe Glu Leu Asp Ala Thr Gly Thr Lys Leu Gly Leu Lys Ala Ser
                245                 250                 255

Ala Thr Thr Glu Phe Lys Val Asp Ala Gly Lys Asp Val Lys Thr Leu
            260                 265                 270

Asn Val Lys Asp Asp Ala Leu Ala Thr Leu Asp Lys Ala Ile Asn Thr
        275                 280                 285

Ile Asp Glu Ser Arg Ser Lys Leu Gly Ala Ile Gln Asn Arg Phe Glu
290                 295                 300

Ser Thr Ile Asn Asn Leu Asn Asn Thr Val Asn Asn Leu Ser Ala Ser
305                 310                 315                 320

Arg Ser Arg Ile Leu Asp Ala Asp Tyr Ala Thr Glu Val Ser Asn Met
                325                 330                 335

Ser Arg Gly Gln Ile Leu Gln Gln Ala Gly Thr Ser Val Leu Ala Gln
            340                 345                 350

Ala Asn Gln Val Pro Gln Thr Val Leu Ser Leu Leu Arg
        355                 360                 365

<210> SEQ ID NO 17
<211> LENGTH: 367
<212> TYPE: PRT
<213> ORGANISM: P. mirabilis2

<400> SEQUENCE: 17

Met Ala Gln Val Ile Asn Thr Asn Tyr Leu Ser Leu Val Thr Gln Asn
1               5                   10                  15

Asn Leu Asn Arg Ser Gln Ser Ala Leu Gly Asn Ala Ile Glu Arg Leu
                20                  25                  30

Ser Ser Gly Met Arg Ile Asn Ser Ala Lys Asp Asp Ala Ala Gly Gln
            35                  40                  45

Ala Ile Ala Asn Arg Phe Thr Ser Asn Ile Asn Gly Leu Thr Gln Ala
        50                  55                  60

Ser Arg Asn Ala Asn Asp Gly Ile Ser Val Ser Gln Thr Thr Glu Gly
65                  70                  75                  80

Ala Leu Asn Glu Ile Asn Asn Leu Gln Arg Ile Arg Glu Leu Thr
                85                  90                  95

Val Gln Ala Lys Asn Gly Thr Asn Ser Asn Ser Asp Ile Asn Ser Ile
            100                 105                 110

Gln Asn Glu Val Asn Gln Arg Leu Asp Glu Ile Asn Arg Val Ser Glu
        115                 120                 125

Gln Thr Gln Phe Asn Gly Val Lys Val Leu Ser Gly Glu Lys Ser Lys
    130                 135                 140

Met Thr Ile Gln Val Gly Thr Asn Asp Asn Glu Val Ile Glu Phe Asn
```

-continued

```
            145                 150                 155                 160
Leu Asp Lys Ile Asp Asn Asp Thr Leu Gly Val Ala Ser Asp Lys Leu
                165                 170                 175
Phe Asp Ala Lys Thr Glu Lys Lys Gly Val Thr Ala Ala Gly Asp Ala
            180                 185                 190
Ile Asp Ala Asn Ala Leu Gly Ile Ser Gly Ser Lys Lys Tyr Val Thr
        195                 200                 205
Gly Ile Ser Val Lys Glu Tyr Lys Val Asp Gly Lys Val Ser Ser Asp
    210                 215                 220
Lys Val Val Leu Asn Asp Gly Ser Asp Tyr Ile Val Ser Lys Ser
225                 230                 235                 240
Asp Phe Thr Leu Lys Ser Gly Thr Thr Thr Gly Glu Val Glu Phe Thr
                245                 250                 255
Gly Ser Lys Thr Thr Lys Phe Thr Ala Asp Ala Gly Lys Asp Val Lys
            260                 265                 270
Val Leu Asn Val Lys Asp Asp Ala Leu Ala Thr Leu Asp Asn Ala Ile
        275                 280                 285
Ser Lys Val Asp Glu Ser Arg Ser Lys Leu Gly Ala Ile Gln Asn Arg
    290                 295                 300
Phe Gln Ser Thr Ile Asn Asn Leu Asn Asn Thr Val Asn Asn Leu Ser
305                 310                 315                 320
Ala Ser Arg Ser Arg Ile Leu Asp Ala Asp Tyr Ala Thr Glu Val Ser
                325                 330                 335
Asn Met Ser Lys Asn Gln Ile Leu Gln Gln Ala Gly Thr Ala Val Leu
            340                 345                 350
Ala Gln Ala Asn Gln Val Pro Gln Thr Val Leu Ser Leu Leu Arg
        355                 360                 365
```

<210> SEQ ID NO 18
<211> LENGTH: 506
<212> TYPE: PRT
<213> ORGANISM: S. typhimurium2

<400> SEQUENCE: 18

```
Met Ala Gln Val Ile Asn Thr Asn Ser Leu Ser Leu Leu Thr Gln Asn
1               5                   10                  15
Asn Leu Asn Lys Ser Gln Ser Ala Leu Gly Thr Ala Ile Glu Arg Leu
                20                  25                  30
Ser Ser Gly Leu Arg Ile Asn Ser Ala Lys Asp Asp Ala Ala Gly Gln
            35                  40                  45
Ala Ile Ala Asn Arg Phe Thr Ala Asn Ile Lys Gly Leu Thr Gln Ala
        50                  55                  60
Ser Arg Asn Ala Asn Asp Gly Ile Ser Ile Ala Gln Thr Thr Glu Gly
65                  70                  75                  80
Ala Leu Asn Glu Ile Asn Asn Asn Leu Gln Arg Val Arg Glu Leu Ala
                85                  90                  95
Val Gln Ser Ala Asn Ser Thr Asn Ser Gln Ser Asp Leu Asp Ser Ile
            100                 105                 110
Gln Ala Glu Ile Thr Gln Arg Leu Asn Glu Ile Asp Arg Val Ser Gly
        115                 120                 125
Gln Thr Gln Phe Asn Gly Val Lys Val Leu Ala Gln Asp Asn Thr Leu
    130                 135                 140
Thr Ile Gln Val Gly Ala Asn Asp Gly Glu Thr Ile Asp Ile Asp Leu
145                 150                 155                 160
```

```
Lys Gln Ile Asn Ser Gln Thr Leu Gly Leu Asp Ser Leu Asn Val Gln
                165                 170                 175
Lys Ala Tyr Asp Val Lys Asp Thr Ala Val Thr Thr Lys Ala Tyr Ala
            180                 185                 190
Asn Asn Gly Thr Thr Leu Asp Val Ser Gly Leu Asp Asp Ala Ala Ile
        195                 200                 205
Lys Ala Ala Thr Gly Gly Thr Asn Gly Thr Ala Ser Val Thr Gly Gly
    210                 215                 220
Ala Val Lys Phe Asp Ala Asp Asn Lys Tyr Phe Val Thr Ile Gly
225                 230                 235                 240
Gly Phe Thr Gly Ala Asp Ala Lys Asn Gly Asp Tyr Glu Val Asn
                245                 250                 255
Val Ala Thr Asp Gly Thr Val Thr Leu Ala Ala Gly Ala Thr Lys Thr
            260                 265                 270
Thr Met Pro Ala Gly Ala Thr Thr Lys Thr Glu Val Gln Glu Leu Lys
        275                 280                 285
Asp Thr Pro Ala Val Val Ser Ala Asp Ala Lys Asn Ala Leu Ile Ala
    290                 295                 300
Gly Gly Val Asp Ala Thr Asp Ala Asn Gly Ala Glu Leu Val Lys Met
305                 310                 315                 320
Ser Tyr Thr Asp Lys Asn Gly Lys Thr Ile Glu Gly Gly Tyr Ala Leu
                325                 330                 335
Lys Ala Gly Asp Lys Tyr Tyr Ala Ala Asp Tyr Asp Glu Ala Thr Gly
            340                 345                 350
Ala Ile Lys Ala Lys Thr Thr Ser Tyr Thr Ala Ala Asp Gly Thr Thr
        355                 360                 365
Lys Thr Ala Ala Asn Gln Leu Gly Gly Val Asp Gly Lys Thr Glu Val
    370                 375                 380
Val Thr Ile Asp Gly Lys Thr Tyr Asn Ala Ser Lys Ala Ala Gly His
385                 390                 395                 400
Asp Phe Lys Ala Gln Pro Glu Leu Ala Glu Ala Ala Lys Thr Thr
                405                 410                 415
Glu Asn Pro Leu Gln Lys Ile Asp Ala Ala Leu Ala Gln Val Asp Ala
            420                 425                 430
Leu Arg Ser Asp Leu Gly Ala Val Gln Asn Arg Phe Asn Ser Ala Ile
        435                 440                 445
Thr Asn Leu Gly Asn Thr Val Asn Asn Leu Ser Glu Ala Arg Ser Arg
    450                 455                 460
Ile Glu Asp Ser Asp Tyr Ala Thr Glu Val Ser Asn Met Ser Arg Ala
465                 470                 475                 480
Gln Ile Leu Gln Gln Ala Gly Thr Ser Val Leu Ala Gln Ala Asn Gln
                485                 490                 495
Val Pro Gln Asn Val Leu Ser Leu Leu Arg
            500                 505

<210> SEQ ID NO 19
<211> LENGTH: 490
<212> TYPE: PRT
<213> ORGANISM: S. typhimurium1

<400> SEQUENCE: 19

Met Ala Gln Val Ile Asn Thr Asn Ser Leu Ser Leu Leu Thr Gln Asn
1               5                   10                  15
Asn Leu Asn Lys Ser Gln Ser Ala Leu Gly Thr Ala Ile Glu Arg Leu
            20                  25                  30
```

-continued

```
Ser Ser Gly Leu Arg Ile Asn Ser Ala Lys Asp Asp Ala Gly Gln
        35                  40                  45

Ala Ile Ala Asn Arg Phe Thr Ala Asn Ile Lys Gly Leu Thr Gln Ala
 50                  55                  60

Ser Arg Asn Ala Asn Asp Gly Ile Ser Ile Ala Gln Thr Thr Glu Gly
 65                  70                  75                  80

Ala Leu Asn Glu Ile Asn Asn Leu Gln Arg Val Arg Glu Leu Ala
                 85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Asn Gly
            115                 120                 125

Gln Thr Gln Phe Ser Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
            195                 200                 205

Gly Leu Gly Gly Thr Asp Glu Lys Ile Asp Gly Asp Leu Lys Phe Asp
    210                 215                 220

Asp Thr Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
                245                 250                 255

Val Thr Leu Ala Ala Val Thr Pro Ala Thr Val Thr Thr Ala Thr Ala
            260                 265                 270

Leu Ser Gly Lys Met Tyr Ser Ala Asn Pro Asp Ser Asp Ile Ala Lys
            275                 280                 285

Ala Ala Leu Thr Ala Ala Gly Val Thr Gly Thr Ala Ser Val Val Lys
    290                 295                 300

Met Ser Tyr Thr Asp Asn Asn Gly Lys Thr Ile Asp Gly Gly Leu Ala
305                 310                 315                 320

Val Lys Val Gly Asp Asp Tyr Tyr Ser Ala Thr Gln Asp Lys Asp Gly
                325                 330                 335

Ser Ile Ser Ile Asp Thr Thr Lys Tyr Thr Ala Asp Asn Gly Thr Ser
            340                 345                 350

Lys Thr Ala Leu Asn Lys Leu Gly Gly Ala Asp Gly Lys Thr Glu Val
            355                 360                 365

Val Thr Ile Asp Gly Lys Thr Tyr Asn Ala Ser Lys Ala Ala Gly His
    370                 375                 380

Asp Phe Lys Ala Glu Pro Glu Leu Ala Glu Gln Ala Ala Lys Thr Thr
385                 390                 395                 400

Glu Asn Pro Leu Gln Lys Ile Asp Ala Ala Leu Ala Gln Val Asp Thr
                405                 410                 415

Leu Arg Ser Asp Leu Gly Ala Val Gln Asn Arg Phe Asn Ser Ala Ile
            420                 425                 430

Thr Asn Leu Gly Asn Thr Val Asn Asn Leu Ser Ser Ala Arg Ser Arg
            435                 440                 445
```

```
Ile Glu Asp Ser Asp Tyr Ala Thr Glu Val Ser Asn Met Ser Arg Ala
    450                 455                 460

Gln Ile Leu Gln Gln Ala Gly Thr Ser Val Leu Ala Gln Ala Asn Gln
465                 470                 475                 480

Val Pro Gln Asn Val Leu Ser Leu Leu Arg
                485                 490

<210> SEQ ID NO 20
<211> LENGTH: 351
<212> TYPE: PRT
<213> ORGANISM: S. marcesens

<400> SEQUENCE: 20

Met Ala Gln Val Ile Asn Thr Asn Ser Leu Ser Leu Met Ala Gln Asn
1               5                   10                  15

Asn Leu Asn Lys Ser Gln Ser Ser Leu Gly Thr Ala Ile Glu Arg Leu
                20                  25                  30

Ser Ser Gly Leu Arg Ile Asn Ser Ala Lys Asp Asp Ala Ala Gly Gln
            35                  40                  45

Ala Ile Ser Asn Arg Phe Thr Ala Asn Ile Lys Gly Leu Thr Gln Ala
        50                  55                  60

Ser Arg Asn Ala Asn Asp Gly Ile Ser Leu Ala Gln Thr Thr Glu Gly
65                  70                  75                  80

Ala Leu Asn Glu Val Asn Asp Asn Leu Gln Asn Ile Arg Arg Leu Thr
                85                  90                  95

Val Gln Ala Gln Asn Gly Ser Asn Ser Thr Ser Asp Leu Lys Ser Ile
            100                 105                 110

Gln Asp Glu Ile Thr Gln Arg Leu Ser Glu Ile Asn Arg Ile Ser Glu
        115                 120                 125

Gln Thr Asp Phe Asn Gly Val Lys Val Leu Ser Asp Gln Lys Leu
130                 135                 140

Thr Ile Gln Val Gly Ala Asn Asp Gly Glu Thr Thr Asp Ile Asp Leu
145                 150                 155                 160

Lys Lys Ile Asp Ala Lys Gln Leu Gly Met Asp Thr Phe Asp Val Thr
                165                 170                 175

Thr Lys Ser Ala Lys Ala Gly Ala Glu Ile Ala Thr Gly Thr Lys Ile
            180                 185                 190

Thr Val Asp Ser Asp Ala Thr Lys Gln Ala Asp Ala Asp Val Thr Gly
        195                 200                 205

Leu Ala Lys Gly Gln Thr Leu Val Ser Gly Thr Asp Ala Asp Gly Lys
210                 215                 220

Ser Ala Tyr Phe Ile Ala Thr Lys Asp Asp Ala Thr Gly Asp Val Ala
225                 230                 235                 240

Tyr Thr Lys Ala Lys Val Ala Asp Asp Gly Lys Val Thr Asp Ser Gly
                245                 250                 255

Thr Asp Ala Gly Val Lys Asn Pro Leu Ala Thr Leu Asp Lys Ala Leu
            260                 265                 270

Ala Gln Val Asp Gly Leu Arg Ser Ser Leu Gly Ala Val Gln Asn Arg
        275                 280                 285

Phe Asp Ser Val Ile Asn Asn Leu Asn Ser Thr Val Asn Asn Leu Ser
290                 295                 300

Ala Ser Gln Ser Arg Ile Gln Asp Ala Asp Tyr Ala Thr Glu Val Ser
305                 310                 315                 320

Asn Met Ser Arg Ala Asn Ile Leu Gln Gln Ala Gly Thr Ser Val Leu
                325                 330                 335
```

Ala Gln Ala Asn Gln Ser Thr Gln Asn Val Leu Ser Leu Leu Arg
            340                 345                 350

<210> SEQ ID NO 21
<211> LENGTH: 554
<212> TYPE: PRT
<213> ORGANISM: E. coli

<400> SEQUENCE: 21

Met Ala Gln Val Ile Asn Thr Asn Ser Leu Ser Leu Ile Thr Gln Asn
  1               5                  10                  15

Asn Ile Asn Lys Asn Gln Ser Ala Leu Ser Ser Ser Ile Glu Arg Leu
             20                  25                  30

Ser Ser Gly Leu Arg Ile Asn Ser Ala Lys Asp Asp Ala Ala Gly Gln
         35                  40                  45

Ala Ile Ala Asn Arg Phe Thr Ser Asn Ile Lys Gly Leu Thr Gln Ala
     50                  55                  60

Ala Arg Asn Ala Asn Asp Gly Ile Ser Val Ala Gln Thr Thr Glu Gly
 65                  70                  75                  80

Ala Leu Ser Glu Ile Asn Asn Asn Leu Gln Arg Ile Arg Glu Leu Thr
                 85                  90                  95

Val Gln Ala Thr Thr Gly Thr Asn Ser Asp Ser Asp Leu Asp Ser Ile
            100                 105                 110

Gln Asp Glu Ile Lys Ser Arg Leu Asp Glu Ile Asp Arg Val Ser Gly
        115                 120                 125

Gln Thr Gln Phe Asn Gly Val Asn Val Leu Ser Lys Asp Gly Ser Met
    130                 135                 140

Lys Ile Gln Val Gly Ala Asn Asp Gly Glu Thr Ile Thr Ile Asp Leu
145                 150                 155                 160

Lys Lys Ile Asp Ser Asp Thr Leu Asn Leu Ala Gly Phe Asn Val Asn
                165                 170                 175

Gly Glu Gly Glu Thr Ala Asn Thr Ala Ala Thr Leu Lys Asp Met Val
            180                 185                 190

Gly Leu Lys Leu Asp Asn Thr Gly Val Thr Thr Ala Gly Val Asn Arg
        195                 200                 205

Tyr Ile Ala Asp Lys Ala Val Ala Ser Ser Thr Asp Ile Leu Asn Ala
    210                 215                 220

Val Ala Gly Val Asp Gly Ser Lys Val Ser Thr Glu Ala Asp Val Gly
225                 230                 235                 240

Phe Gly Ala Ala Ala Pro Gly Thr Pro Val Glu Tyr Thr Tyr His Lys
                245                 250                 255

Asp Thr Asn Thr Tyr Thr Ala Ser Ala Ser Val Asp Ala Thr Gln Leu
            260                 265                 270

Ala Ala Phe Leu Asn Pro Glu Ala Gly Gly Thr Thr Ala Ala Thr Val
        275                 280                 285

Ser Ile Gly Asn Gly Thr Thr Ala Gln Glu Gln Lys Val Ile Ile Ala
    290                 295                 300

Lys Asp Gly Ser Leu Thr Ala Ala Asp Gly Ala Ala Leu Tyr Leu
305                 310                 315                 320

Asp Asp Thr Gly Asn Leu Ser Lys Thr Asn Ala Gly Thr Asp Thr Gln
                325                 330                 335

Ala Lys Leu Ser Asp Leu Met Ala Asn Asn Ala Asn Ala Lys Thr Val
            340                 345                 350

Ile Thr Thr Asp Lys Gly Thr Phe Thr Ala Asn Thr Thr Lys Phe Asp

```
                355                 360                 365
Gly Val Asp Ile Ser Val Asp Ala Ser Thr Phe Ala Asn Ala Val Lys
        370                 375                 380

Asn Glu Thr Tyr Thr Ala Thr Val Gly Val Thr Leu Pro Ala Thr Tyr
385                 390                 395                 400

Thr Val Asn Asn Gly Thr Ala Ala Ser Ala Tyr Leu Val Asp Gly Lys
                405                 410                 415

Val Ser Lys Thr Pro Ala Glu Tyr Phe Ala Gln Ala Asp Gly Thr Ile
        420                 425                 430

Thr Ser Gly Glu Asn Ala Ala Thr Ser Lys Ala Ile Tyr Val Ser Ala
        435                 440                 445

Asn Gly Asn Leu Thr Thr Asn Thr Ser Glu Ser Glu Ala Thr Thr
    450                 455                 460

Asn Pro Leu Ala Ala Leu Asp Asp Ala Ile Ala Ser Ile Asp Lys Phe
465                 470                 475                 480

Arg Ser Ser Leu Gly Ala Ile Gln Asn Arg Leu Asp Ser Ala Val Thr
                485                 490                 495

Asn Leu Asn Asn Thr Thr Thr Asn Leu Ser Glu Ala Gln Ser Arg Ile
            500                 505                 510

Gln Asp Ala Asp Tyr Ala Thr Glu Val Ser Asn Met Ser Lys Ala Gln
        515                 520                 525

Ile Ile Gln Gln Ala Gly Asn Ser Val Leu Ala Lys Ala Asn Gln Val
    530                 535                 540

Pro Gln Gln Val Leu Ser Leu Gln Gln Gly
545                 550

<210> SEQ ID NO 22
<211> LENGTH: 550
<212> TYPE: PRT
<213> ORGANISM: S. flexneri

<400> SEQUENCE: 22

Met Ala Gln Val Ile Asn Thr Asn Ser Leu Ser Leu Ile Thr Gln Asn
1               5                   10                  15

Asn Ile Asn Lys Asn Gln Ser Ala Leu Ser Ser Ser Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ala Arg Asn Ala Asn Asp Gly Ile Ser Val Ala Gln Thr Thr Glu Gly
65                  70                  75                  80

Ala Leu Ser Glu Ile Asn Asn Asn Leu Gln Arg Ile Arg Glu Leu Thr
                85                  90                  95

Val Gln Ala Ser Thr Gly Thr Asn Ser Asp Ser Asp Leu Asp Ser Ile
            100                 105                 110

Gln Asp Glu Ile Lys Ser Arg Leu Asp Glu Ile Asp Arg Val Ser Gly
        115                 120                 125

Gln Thr Gln Phe Asn Gly Val Asn Val Leu Ala Lys Asp Gly Ser Met
    130                 135                 140

Lys Ile Gln Val Gly Ala Asn Asp Gly Gln Thr Ile Thr Ile Asp Leu
145                 150                 155                 160

Lys Lys Ile Asp Ser Asp Thr Leu Gly Leu Asn Gly Phe Asn Val Asn
                165                 170                 175
```

Gly Gly Gly Ala Val Ala Asn Thr Ala Ala Ser Lys Ala Asp Leu Val
            180                 185                 190

Ala Ala Asn Ala Thr Val Val Gly Asn Lys Tyr Thr Val Ser Ala Gly
        195                 200                 205

Tyr Asp Ala Ala Lys Ala Ser Asp Leu Leu Ala Gly Val Ser Asp Gly
    210                 215                 220

Asp Thr Val Gln Ala Thr Ile Asn Asn Gly Phe Gly Thr Ala Ala Ser
225                 230                 235                 240

Ala Thr Asn Tyr Lys Tyr Asp Ser Ala Ser Lys Ser Tyr Ser Phe Asp
            245                 250                 255

Thr Thr Thr Ala Ser Ala Ala Asp Val Gln Lys Tyr Leu Thr Pro Gly
            260                 265                 270

Val Gly Asp Thr Ala Lys Gly Thr Ile Thr Ile Asp Gly Ser Ala Gln
        275                 280                 285

Asp Val Gln Ile Ser Ser Asp Gly Lys Ile Thr Ala Ser Asn Gly Asp
    290                 295                 300

Lys Leu Tyr Ile Asp Thr Thr Gly Arg Leu Thr Lys Asn Gly Ser Gly
305                 310                 315                 320

Ala Ser Leu Thr Glu Ala Ser Leu Ser Thr Leu Ala Ala Asn Asn Thr
            325                 330                 335

Lys Ala Thr Thr Ile Asp Ile Gly Gly Thr Ser Ile Ser Phe Thr Gly
            340                 345                 350

Asn Ser Thr Thr Pro Asp Thr Ile Thr Tyr Ser Val Thr Gly Ala Lys
        355                 360                 365

Val Asp Gln Ala Ala Phe Asp Lys Ala Val Ser Thr Ser Gly Asn Asn
    370                 375                 380

Val Asp Phe Thr Thr Ala Gly Tyr Ser Val Asn Gly Thr Thr Gly Ala
385                 390                 395                 400

Val Thr Lys Gly Val Asp Ser Val Tyr Val Asp Asn Asn Glu Ala Leu
            405                 410                 415

Thr Thr Ser Asp Thr Val Asp Phe Tyr Leu Gln Asp Asp Gly Ser Val
            420                 425                 430

Thr Asn Gly Ser Gly Lys Ala Val Tyr Lys Asp Ala Asp Gly Lys Leu
        435                 440                 445

Thr Thr Asp Ala Glu Thr Lys Ala Ala Thr Thr Ala Asp Pro Leu Lys
    450                 455                 460

Ala Leu Asp Glu Ala Ile Ser Ser Ile Asp Lys Phe Arg Ser Ser Leu
465                 470                 475                 480

Gly Ala Val Gln Asn Arg Leu Asp Ser Ala Val Thr Asn Leu Asn Asn
            485                 490                 495

Thr Thr Thr Asn Leu Ser Glu Ala Gln Ser Arg Ile Gln Asp Ala Asp
            500                 505                 510

Tyr Ala Thr Glu Val Ser Asn Met Ser Lys Ala Gln Ile Ile Gln Gln
        515                 520                 525

Ala Gly Asn Ser Val Leu Ala Lys Ala Asn Gln Val Pro Gln Gln Val
    530                 535                 540

Leu Ser Leu Leu Gln Gly
545                 550

<210> SEQ ID NO 23
<211> LENGTH: 286
<212> TYPE: PRT
<213> ORGANISM: T. pallidumA

<400> SEQUENCE: 23

Met Ile Ile Asn His Asn Met Ser Ala Met Phe Ala Gln Arg Thr Leu
1               5                   10                  15

Gly His Thr Asn Val Gln Val Gly Lys Gly Ile Glu Lys Leu Ser Ser
            20                  25                  30

Gly Tyr Arg Ile Asn Arg Ala Gly Asp Asp Ala Ser Gly Leu Ala Val
        35                  40                  45

Ser Glu Lys Met Arg Ser Gln Ile Arg Gly Leu Asn Gln Ala Ser Thr
50                  55                  60

Asn Ala Ser Asn Gly Val Asn Phe Ile Gln Val Thr Glu Ala Tyr Leu
65                  70                  75                  80

Gln Glu Thr Thr Asp Ile Met Gln Arg Ile Arg Glu Leu Ala Ile Gln
                85                  90                  95

Ala Ala Asn Gly Ile Tyr Ser Ala Glu Asp Arg Met Gln Ile Gln Val
            100                 105                 110

Glu Val Ser Gln Leu Val Ala Glu Val Asp Arg Ile Ala Ser Ser Ala
        115                 120                 125

Gln Phe Asn Gly Met Asn Leu Leu Thr Gly Arg Phe Ser Arg Thr Glu
130                 135                 140

Gly Glu Asn Val Ile Gly Gly Ser Met Trp Phe His Ile Gly Ala Asn
145                 150                 155                 160

Met Asp Gln Arg Met Arg Val Tyr Ile Gly Thr Met Thr Ala Val Ala
                165                 170                 175

Leu Gly Val Arg Asn Gly Val Asp Glu Ser Ile Met Ser Ile Glu Thr
            180                 185                 190

Ala Asp Ser Ala Asn Lys Ser Ile Gly Thr Ile Asp Ala Ala Leu Lys
        195                 200                 205

Arg Ile Asn Lys Gln Arg Ala Asp Leu Gly Gly Tyr Gln Asn Arg Met
210                 215                 220

Glu Tyr Thr Val Val Gly Leu Asp Ile Ala Ala Glu Asn Leu Gln Ala
225                 230                 235                 240

Ala Glu Ser Arg Ile Arg Asp Ala Asn Ile Ala Lys Gln Met Val Glu
                245                 250                 255

Tyr Thr Lys Asn Gln Val Leu Thr Gln Ser Gly Thr Ala Met Leu Ala
            260                 265                 270

Gln Ala Asn Thr Ser Ala Gln Ser Ile Leu Ser Ile Leu Arg
        275                 280                 285

<210> SEQ ID NO 24
<211> LENGTH: 286
<212> TYPE: PRT
<213> ORGANISM: T. pallidumB

<400> SEQUENCE: 24

Met Ile Ile Asn His Asn Met Ser Ala Met Phe Ala Gln Arg Thr Leu
1               5                   10                  15

Gly Asn Thr Asn Leu Ser Val Gln Lys Asn Met Glu Lys Leu Ser Ser
            20                  25                  30

Gly Leu Arg Ile Asn Arg Ala Gly Asp Asp Ala Ser Gly Leu Ala Val
        35                  40                  45

Ser Glu Lys Met Arg Ser Gln Ile Arg Gly Leu Asn Gln Ala Ser Thr
50                  55                  60

Asn Ala Gln Asn Gly Ile Ser Phe Ile Gln Val Ala Glu Ser Tyr Leu
65                  70                  75                  80

Gln Glu Thr Thr Asp Val Ile Gln Arg Ile Arg Glu Leu Ser Val Gln

```
                85                  90                  95

Ser Ala Asn Gly Ile Tyr Ser Ala Glu Asp Arg Met Tyr Ile Gln Val
            100                 105                 110

Glu Val Ser Gln Leu Val Ala Glu Ile Asp Arg Ile Ala Ser His Ala
        115                 120                 125

Gln Phe Asn Gly Met Asn Met Leu Thr Gly Arg Phe Ala Arg Glu Thr
    130                 135                 140

Gly Glu Asn Thr Val Thr Ala Ser Met Trp Phe His Ile Gly Ala Asn
145                 150                 155                 160

Met Asp Gln Arg Thr Arg Ala Tyr Ile Gly Thr Met Thr Ala Ala Ala
                165                 170                 175

Leu Gly Val Arg Asp Val Gly Asp Glu Ser Ile Leu Asn Ile Asp Asp
            180                 185                 190

Pro Glu Lys Ala Asn Arg Ala Ile Gly Thr Leu Asp Glu Ala Ile Lys
        195                 200                 205

Lys Ile Asn Lys Gln Arg Ala Asp Leu Gly Ala Tyr Gln Asn Arg Leu
    210                 215                 220

Glu Tyr Thr Val Ile Gly Val Asn Val Ala Ala Glu Asn Leu Gln Ala
225                 230                 235                 240

Ala Glu Ser Arg Ile Arg Asp Val Asp Met Ala Lys Glu Met Val Asp
                245                 250                 255

Tyr Thr Lys Asn Gln Ile Leu Val Gln Ser Gly Thr Ala Met Leu Ala
            260                 265                 270

Gln Ala Asn Gln Ala Thr Gln Ser Val Leu Ser Leu Leu Arg
        275                 280                 285

<210> SEQ ID NO 25
<211> LENGTH: 283
<212> TYPE: PRT
<213> ORGANISM: L. pneumophila

<400> SEQUENCE: 25

Met Ile Ile Asn His Asn Leu Ser Ala Val Asn Ala His Arg Ser Leu
 1               5                  10                  15

Lys Phe Asn Glu Leu Ala Val Asp Lys Thr Met Lys Ala Leu Ser Ser
            20                  25                  30

Gly Met Arg Ile Asn Ser Ala Ala Asp Asp Ala Ser Gly Leu Ala Val
        35                  40                  45

Ser Glu Lys Leu Arg Thr Gln Val Asn Gly Leu Arg Gln Ala Glu Arg
    50                  55                  60

Asn Thr Glu Asp Gly Met Ser Phe Ile Gln Thr Ala Glu Gly Phe Leu
65                  70                  75                  80

Glu Gln Thr Ser Asn Ile Ile Gln Arg Ile Arg Val Leu Ala Ile Gln
                85                  90                  95

Thr Ser Asn Gly Ile Tyr Ser Asn Glu Asp Arg Gln Leu Val Gln Val
            100                 105                 110

Glu Val Ser Ala Leu Val Asp Glu Val Asp Arg Ile Ala Ser Gln Ala
        115                 120                 125

Glu Phe Asn Lys Phe Lys Leu Phe Glu Gly Gln Phe Ala Arg Gly Ser
    130                 135                 140

Arg Val Ala Ser Met Trp Phe His Met Gly Pro Asn Gln Asn Gln Arg
145                 150                 155                 160

Glu Arg Phe Tyr Ile Gly Thr Met Thr Ser Lys Ala Leu Lys Leu Val
                165                 170                 175
```

-continued

```
Lys Ala Asp Gly Arg Pro Ile Ala Ile Ser Ser Pro Gly Glu Ala Asn
                180                 185                 190

Asp Val Ile Gly Leu Ala Asp Ala Ala Leu Thr Lys Ile Met Lys Gln
            195                 200                 205

Arg Ala Asp Met Gly Ala Tyr Tyr Asn Arg Leu Glu Tyr Thr Ala Lys
        210                 215                 220

Gly Leu Met Gly Ala Tyr Glu Asn Met Gln Ala Ser Glu Ser Arg Ile
225                 230                 235                 240

Arg Asp Ala Asp Met Ala Glu Glu Val Val Ser Leu Thr Thr Lys Gln
                245                 250                 255

Ile Leu Val Gln Ser Gly Thr Ala Met Leu Ala Arg Ala Asn Met Lys
            260                 265                 270

Pro Asn Ser Val Leu Lys Leu Leu Gln His Ile
        275                 280

<210> SEQ ID NO 26
<211> LENGTH: 336
<212> TYPE: PRT
<213> ORGANISM: B. burgdorferei

<400> SEQUENCE: 26

Met Ile Ile Asn His Asn Thr Ser Ala Ile Asn Ala Ser Arg Asn Asn
 1               5                  10                  15

Gly Ile Asn Ala Ala Asn Leu Ser Lys Thr Gln Glu Lys Leu Ser Ser
            20                  25                  30

Gly Tyr Arg Ile Asn Arg Ala Ser Asp Asp Ala Ala Gly Met Gly Val
        35                  40                  45

Ser Gly Lys Ile Asn Ala Gln Ile Arg Gly Leu Ser Gln Ala Ser Arg
 50                 55                  60

Asn Thr Ser Lys Ala Ile Asn Phe Ile Gln Thr Thr Glu Gly Asn Leu
65                  70                  75                  80

Asn Glu Val Glu Lys Val Leu Val Arg Met Lys Glu Leu Ala Val Gln
                85                  90                  95

Ser Gly Asn Gly Thr Tyr Ser Asp Ala Asp Arg Gly Ser Ile Gln Ile
            100                 105                 110

Glu Ile Glu Gln Leu Thr Asp Glu Ile Asn Arg Ile Ala Asp Gln Ala
        115                 120                 125

Gln Tyr Asn Gln Met His Met Leu Ser Asn Lys Ser Ala Ser Gln Asn
    130                 135                 140

Val Arg Thr Ala Glu Glu Leu Gly Met Gln Pro Ala Lys Ile Asn Thr
145                 150                 155                 160

Pro Ala Ser Leu Ser Gly Ser Gln Ala Ser Trp Thr Leu Arg Val His
                165                 170                 175

Val Gly Ala Asn Gln Asp Glu Ala Ile Ala Val Asn Ile Tyr Ala Ala
            180                 185                 190

Asn Val Ala Asn Leu Phe Ser Gly Glu Gly Ala Gln Ala Ala Gln Thr
        195                 200                 205

Ala Pro Val Gln Glu Gly Ala Gln Glu Gly Ala Gln Gln Pro Ala
    210                 215                 220

Pro Val Thr Ala Pro Ser Gln Gly Gly Val Asn Ser Pro Val Asn Val
225                 230                 235                 240

Thr Thr Thr Val Asp Ala Asn Thr Ser Leu Ala Lys Ile Glu Asn Ala
                245                 250                 255

Ile Arg Met Ile Ser Asp Gln Arg Ala Asn Leu Gly Ala Phe Gln Asn
            260                 265                 270
```

Arg Leu Glu Ser Ile Lys Asp Ser Thr Glu Tyr Ala Ile Glu Asn Leu
                275                 280                 285

Lys Ala Ser Tyr Ala Gln Ile Lys Asp Ala Thr Met Thr Asp Glu Val
            290                 295                 300

Val Ala Ala Thr Thr Asn Ser Ile Leu Thr Gln Ser Ala Met Ala Met
305                 310                 315                 320

Ile Ala Gln Ala Asn Gln Val Pro Gln Tyr Val Leu Ser Leu Leu Arg
                325                 330                 335

<210> SEQ ID NO 27
<211> LENGTH: 304
<212> TYPE: PRT
<213> ORGANISM: B. subtilus

<400> SEQUENCE: 27

Met Arg Ile Asn His Asn Ile Ala Ala Leu Asn Thr Leu Asn Arg Leu
1               5                   10                  15

Ser Ser Asn Asn Ser Ala Ser Gln Lys Asn Met Glu Lys Leu Ser Ser
                20                  25                  30

Gly Leu Arg Ile Asn Arg Ala Gly Asp Asp Ala Ala Gly Leu Ala Ile
            35                  40                  45

Ser Glu Lys Met Arg Gly Gln Ile Arg Gly Leu Glu Met Ala Ser Lys
50                  55                  60

Asn Ser Gln Asp Gly Ile Ser Leu Ile Gln Thr Ala Glu Gly Ala Leu
65                  70                  75                  80

Thr Glu Thr His Ala Ile Leu Gln Arg Val Arg Glu Leu Val Val Gln
                85                  90                  95

Ala Gly Asn Thr Gly Thr Gln Asp Lys Ala Thr Asp Leu Gln Ser Ile
            100                 105                 110

Gln Asp Glu Ile Ser Ala Leu Thr Asp Glu Ile Asp Gly Ile Ser Asn
        115                 120                 125

Arg Thr Glu Phe Asn Gly Lys Lys Leu Leu Asp Gly Thr Tyr Lys Val
    130                 135                 140

Asp Thr Ala Thr Pro Ala Asn Gln Lys Asn Leu Val Phe Gln Ile Gly
145                 150                 155                 160

Ala Asn Ala Thr Gln Gln Ile Ser Val Asn Ile Glu Asp Met Gly Ala
                165                 170                 175

Asp Ala Leu Gly Ile Lys Glu Ala Asp Gly Ser Ile Ala Ala Leu His
            180                 185                 190

Ser Val Asn Asp Leu Asp Val Thr Lys Phe Ala Asp Asn Ala Ala Asp
        195                 200                 205

Thr Ala Asp Ile Gly Phe Asp Ala Gln Leu Lys Val Val Asp Glu Ala
    210                 215                 220

Ile Asn Gln Val Ser Ser Gln Arg Ala Lys Leu Gly Ala Val Gln Asn
225                 230                 235                 240

Arg Leu Glu His Thr Ile Asn Asn Leu Ser Ala Ser Gly Glu Asn Leu
                245                 250                 255

Thr Ala Ala Glu Ser Arg Ile Arg Asp Val Asp Met Ala Lys Glu Met
            260                 265                 270

Ser Glu Phe Thr Lys Asn Asn Ile Leu Ser Gln Ala Ser Gln Ala Met
        275                 280                 285

Leu Ala Gln Ala Asn Gln Gln Pro Gln Asn Val Leu Gln Leu Leu Arg
    290                 295                 300

```
<210> SEQ ID NO 28
<211> LENGTH: 281
<212> TYPE: PRT
<213> ORGANISM: C. difficile

<400> SEQUENCE: 28

Met Arg Val Asn Thr Asn Val Ser Ala Leu Ile Ala Asn Asn Gln Met
 1               5                  10                  15

Gly Arg Asn Val Ser Gly Gln Ser Lys Ser Met Glu Lys Leu Ser Ser
            20                  25                  30

Gly Leu Arg Ile Lys Arg Ala Ala Asp Asp Ala Ala Gly Leu Ala Ile
        35                  40                  45

Ser Glu Lys Met Arg Ala Gln Leu Lys Gly Leu Asp Gln Ala Gly Arg
    50                  55                  60

Asn Val Gln Asp Gly Ile Ser Val Val Gln Thr Ala Glu Gly Ala Leu
65                  70                  75                  80

Glu Glu Thr Gly Asn Ile Leu Thr Arg Met Arg Thr Leu Ala Val Gln
                85                  90                  95

Ala Ser Asn Glu Thr Asn Ser Lys Asp Glu Arg Ala Lys Ile Ala Gly
            100                 105                 110

Glu Met Glu Gln Leu Arg Ser Glu Val Asp Arg Ile Ala Asp Ser Thr
        115                 120                 125

Lys Phe Asn Gly Glu Asn Leu Leu Ser Ser Asp Lys Lys Ile Ala Leu
    130                 135                 140

Gln Val Gly Ala Glu Ala Val Ser Asn Asn Val Ile Glu Val Ser Leu
145                 150                 155                 160

Ile Asn Thr Lys Gly Val Leu Thr Thr Arg Asn Val Asn Ser Ala Asn
                165                 170                 175

Ile Asp Ala Met Ser Val Ser Gly Ser Ile Gly Thr Glu Ala Ala Ser
            180                 185                 190

Lys Met Ile Val Asn Leu Asp Ser Ser Leu Ala Asp Ile Asn Ser Ala
        195                 200                 205

Arg Ala Leu Leu Gly Ala Gln Gln Asn Arg Leu Glu Ser Thr Gln Asn
    210                 215                 220

Asn Leu Asn Asn Thr Val Glu Asn Val Thr Ala Ala Glu Ser Arg Ile
225                 230                 235                 240

Arg Asp Thr Asp Val Ala Ser Glu Met Val Asn Leu Ser Lys Met Asn
                245                 250                 255

Ile Leu Val Gln Ala Ser Gln Ser Met Leu Ser Gln Ala Asn Gln Gln
            260                 265                 270

Pro Gln Gly Val Leu Gln Leu Gly
        275                 280

<210> SEQ ID NO 29
<211> LENGTH: 394
<212> TYPE: PRT
<213> ORGANISM: R. meliloti

<400> SEQUENCE: 29

Met Thr Ser Ile Leu Thr Asn Asn Ser Ala Met Ala Ala Leu Ser Thr
 1               5                  10                  15

Leu Arg Ser Ile Ser Ser Ser Met Glu Asp Thr Gln Ser Arg Ile Ser
            20                  25                  30

Ser Gly Leu Arg Val Gly Ser Ala Ser Asp Asn Ala Ala Tyr Trp Ser
        35                  40                  45

Ile Ala Thr Thr Met Arg Ser Asp Asn Gln Ala Leu Ser Ala Val Gln
```

50                  55                  60

Asp Ala Leu Gly Leu Gly Ala Ala Lys Val Asp Thr Ala Tyr Ser Gly
 65                  70                  75                  80

Met Glu Ser Ala Ile Glu Val Val Lys Glu Ile Lys Ala Lys Leu Val
                 85                  90                  95

Ala Ala Thr Glu Asp Gly Val Asp Lys Ala Lys Ile Gln Glu Ile
            100                 105                 110

Thr Gln Leu Lys Asp Gln Leu Thr Ser Ile Ala Glu Ala Ser Phe
            115                 120                 125

Ser Gly Glu Asn Trp Leu Gln Ala Asp Leu Ser Gly Pro Val Thr
        130                 135                 140

Lys Ser Val Val Gly Gly Phe Val Arg Asp Ser Ser Gly Ala Val Ser
145                 150                 155                 160

Val Lys Lys Val Asp Tyr Ser Leu Asn Thr Asp Thr Val Leu Phe Asp
                165                 170                 175

Thr Thr Gly Asn Thr Gly Ile Leu Asp Lys Val Tyr Asn Val Ser Gln
                180                 185                 190

Ala Ser Val Thr Leu Pro Val Asn Val Asn Gly Thr Thr Ser Glu Tyr
                195                 200                 205

Thr Val Gly Ala Tyr Asn Val Asp Asp Leu Ile Asp Ala Ser Ala Thr
210                 215                 220

Phe Asp Gly Asp Tyr Ala Asn Val Gly Ala Gly Ala Leu Ala Gly Asp
225                 230                 235                 240

Tyr Val Lys Val Gln Gly Ser Trp Val Lys Ala Val Asp Val Ala Ala
                245                 250                 255

Thr Gly Gln Glu Val Val Tyr Asp Asp Gly Thr Thr Lys Trp Gly Val
            260                 265                 270

Asp Thr Thr Val Thr Gly Ala Pro Ala Thr Asn Val Ala Ala Pro Ala
            275                 280                 285

Ser Ile Ala Thr Ile Asp Ile Thr Ile Ala Ala Gln Ala Gly Asn Leu
        290                 295                 300

Asp Ala Leu Ile Ala Gly Val Asp Glu Ala Leu Thr Asp Met Thr Ser
305                 310                 315                 320

Ala Ala Ala Ser Leu Gly Ser Ile Ser Ser Arg Ile Asp Leu Gln Ser
                325                 330                 335

Asp Phe Val Asn Lys Leu Ser Asp Ser Ile Asp Ser Gly Val Gly Arg
                340                 345                 350

Leu Val Asp Ala Asp Met Asn Glu Glu Ser Thr Arg Leu Lys Ala Leu
                355                 360                 365

Gln Thr Gln Gln Gln Leu Ala Ile Gln Ala Leu Ser Ile Ala Asn Ser
            370                 375                 380

Asp Ser Gln Asn Val Leu Ser Leu Phe Arg
385                 390

<210> SEQ ID NO 30
<211> LENGTH: 306
<212> TYPE: PRT
<213> ORGANISM: A. tumefaciens

<400> SEQUENCE: 30

Met Ala Ser Ile Leu Thr Asn Asn Ala Met Ala Ala Leu Ser Thr
 1               5                  10                  15

Leu Arg Ser Ile Ala Ser Asp Leu Ser Thr Thr Gln Asp Arg Ile Ser
                20                  25                  30

```
Ser Gly Leu Lys Val Gly Ala Ser Asp Asn Ala Ala Tyr Trp Ser
         35                  40                  45

Ile Ala Thr Thr Met Arg Ser Asp Asn Lys Ala Leu Gly Ala Val Ser
 50                  55                  60

Asp Ala Leu Gly Met Gly Ala Ala Lys Val Asp Thr Ala Ser Ala Gly
 65                  70                  75                  80

Met Asp Ala Ala Ile Lys Val Thr Asp Ile Lys Ala Lys Val Val
                 85                  90                  95

Ala Ala Lys Glu Gln Gly Val Asp Lys Thr Lys Val Gln Glu Val
            100                 105                 110

Ser Gln Leu Leu Asp Gln Leu Lys Ser Ile Gly Thr Ser Ala Ser Phe
            115                 120                 125

Asn Gly Glu Asn Trp Leu Val Ser Ser Ala Asn Ala Thr Lys Thr Val
130                 135                 140

Val Ser Gly Phe Val Arg Asp Ala Gly Gly Thr Val Ser Val Lys Thr
145                 150                 155                 160

Thr Asp Tyr Ala Leu Asp Ala Asn Ser Met Leu Tyr Thr Glu Gly Thr
                165                 170                 175

Pro Gly Thr Ile Asp Ala Asn Ser Gly Ile Leu Asn Ala Thr Gly Ala
            180                 185                 190

Thr Thr Thr Val Gly Ala Lys Thr Tyr Thr Gln Ile Ser Val Leu Asp
            195                 200                 205

Met Asn Val Gly Thr Asp Asp Leu Asp Asn Ala Leu Tyr Ser Val Glu
            210                 215                 220

Thr Ala Leu Thr Lys Met Thr Ser Ala Gly Ala Lys Leu Gly Ser Leu
225                 230                 235                 240

Ser Ala Arg Ile Asp Leu Gln Ser Gly Phe Ala Asp Lys Leu Ser Asp
                245                 250                 255

Thr Ile Glu Lys Gly Val Gly Arg Leu Val Asp Ala Asp Met Asn Glu
            260                 265                 270

Glu Ser Thr Lys Leu Lys Ala Leu Gln Thr Gln Gln Leu Ala Ile
            275                 280                 285

Gln Ala Leu Ser Ile Ala Asn Ser Asp Ser Gln Asn Ile Leu Ser Leu
290                 295                 300

Phe Arg
305

<210> SEQ ID NO 31
<211> LENGTH: 410
<212> TYPE: PRT
<213> ORGANISM: R. lupini

<400> SEQUENCE: 31

Met Ala Ser Val Leu Thr Asn Ile Asn Ala Met Ser Ala Leu Gln Thr
 1               5                  10                  15

Leu Arg Ser Ile Ser Ser Asn Met Glu Asp Thr Gln Ser Arg Ile Ser
                 20                  25                  30

Ser Gly Met Arg Val Gly Ser Ala Ser Asp Asn Ala Ala Tyr Trp Ser
             35                  40                  45

Ile Ala Thr Thr Met Arg Ser Asp Asn Ala Ser Leu Ser Ala Val Gln
 50                  55                  60

Asp Ala Ile Gly Leu Gly Ala Ala Lys Val Asp Thr Ala Ser Ala Gly
 65                  70                  75                  80

Met Asp Ala Val Ile Asp Val Val Lys Gln Ile Lys Asn Lys Leu Val
                 85                  90                  95
```

Thr Ala Gln Glu Ser Ser Ala Asp Lys Thr Lys Ile Gln Gly Glu Val
                100                 105                 110

Lys Gln Leu Gln Glu Gln Leu Lys Gly Ile Val Asp Ser Ala Ser Phe
            115                 120                 125

Ser Gly Glu Asn Trp Leu Lys Gly Asp Leu Ser Thr Thr Thr Lys
            130                 135                 140

Ser Val Val Gly Ser Phe Val Arg Glu Gly Gly Thr Val Ser Val Lys
145                 150                 155                 160

Thr Ile Asp Tyr Ala Leu Asn Ala Ser Lys Val Leu Val Asp Thr Arg
                165                 170                 175

Ala Thr Gly Thr Lys Thr Gly Ile Leu Asp Thr Ala Tyr Thr Gly Leu
            180                 185                 190

Asn Ala Asn Thr Val Thr Val Asp Ile Asn Lys Gly Gly Val Ile Thr
            195                 200                 205

Gln Ala Ser Val Arg Ala Tyr Ser Thr Asp Glu Met Leu Ser Leu Gly
            210                 215                 220

Ala Lys Val Asp Gly Ala Asn Ser Asn Val Ala Val Gly Gly Gly Ser
225                 230                 235                 240

Ala Phe Val Lys Val Asp Gly Ser Trp Val Lys Gly Ser Val Asp Ala
                245                 250                 255

Ala Ala Ser Ile Thr Ala Ser Thr Pro Val Ala Gly Lys Phe Ala Ala
            260                 265                 270

Ala Tyr Thr Ala Ala Glu Ala Gly Thr Ala Ala Ala Gly Asp Ala
            275                 280                 285

Ile Ile Val Asp Glu Thr Asn Ser Gly Ala Gly Ala Val Asn Leu Thr
            290                 295                 300

Gln Ser Val Leu Thr Met Asp Val Ser Ser Met Ser Thr Asp Val
305                 310                 315                 320

Gly Ser Tyr Leu Thr Gly Val Glu Lys Ala Leu Thr Ser Leu Thr Ser
                325                 330                 335

Ala Gly Ala Glu Leu Gly Ser Ile Lys Gln Arg Ile Asp Leu Gln Val
            340                 345                 350

Asp Phe Ala Ser Lys Leu Gly Asp Ala Leu Ala Lys Gly Ile Gly Arg
            355                 360                 365

Leu Val Asp Ala Asp Met Asn Glu Glu Ser Thr Lys Leu Lys Ala Leu
370                 375                 380

Gln Thr Gln Gln Gln Leu Ala Ile Gln Ser Leu Ser Ile Ala Asn Ser
385                 390                 395                 400

Asp Ser Gln Asn Ile Leu Ser Leu Phe Arg
                405                 410

<210> SEQ ID NO 32
<211> LENGTH: 287
<212> TYPE: PRT
<213> ORGANISM: L. monocytogenes

<400> SEQUENCE: 32

Met Lys Val Asn Thr Asn Ile Ile Ser Leu Lys Thr Gln Glu Tyr Leu
1               5                   10                  15

Arg Lys Asn Asn Glu Gly Met Thr Gln Ala Gln Glu Arg Leu Ala Ser
            20                  25                  30

Gly Lys Arg Ile Asn Ser Ser Leu Asp Asp Ala Ala Gly Leu Ala Val
            35                  40                  45

Val Thr Arg Met Asn Val Lys Ser Thr Gly Leu Asp Ala Ala Ser Lys

```
                50                  55                  60
Asn Ser Ser Met Gly Ile Asp Leu Leu Gln Thr Ala Asp Ser Ala Leu
 65                  70                  75                  80

Ser Ser Met Ser Ser Ile Leu Gln Arg Met Arg Gln Leu Ala Val Gln
                 85                  90                  95

Ser Ser Asn Gly Ser Phe Ser Asp Glu Asp Arg Lys Gln Tyr Thr Ala
                100                 105                 110

Glu Phe Gly Ser Leu Ile Lys Glu Leu Asp His Val Ala Asp Thr Thr
                115                 120                 125

Asn Tyr Asn Asn Ile Lys Leu Leu Asp Gln Thr Ala Thr Gly Ala Ala
                130                 135                 140

Thr Gln Val Ser Ile Gln Ala Ser Asp Lys Ala Asn Asp Leu Ile Asn
145                 150                 155                 160

Ile Asp Leu Phe Asn Ala Lys Gly Leu Ser Ala Gly Thr Ile Thr Leu
                165                 170                 175

Gly Ser Gly Ser Thr Val Ala Gly Tyr Ser Ala Leu Ser Val Ala Asp
                180                 185                 190

Ala Asp Ser Ser Gln Glu Ala Thr Glu Ala Ile Asp Glu Leu Ile Asn
                195                 200                 205

Asn Ile Ser Asn Gly Arg Ala Leu Leu Gly Ala Gly Met Ser Arg Leu
                210                 215                 220

Ser Tyr Asn Val Ser Asn Val Asn Asn Gln Ser Ile Ala Thr Lys Ala
225                 230                 235                 240

Ser Ala Ser Ser Ile Glu Asp Ala Asp Met Ala Ala Glu Met Ser Glu
                245                 250                 255

Met Thr Lys Tyr Lys Ile Leu Thr Gln Thr Ser Ile Ser Met Leu Ser
                260                 265                 270

Gln Ala Asn Gln Thr Pro Gln Met Leu Thr Gln Leu Ile Asn Ser
                275                 280                 285

<210> SEQ ID NO 33
<211> LENGTH: 399
<212> TYPE: PRT
<213> ORGANISM: B. clarridgeiae

<400> SEQUENCE: 33

Met Gly Thr Ser Leu Leu Thr Asn Lys Ser Ala Met Thr Ala Leu Gln
 1                   5                  10                  15

Thr Leu Arg Ser Ile Asp Ala Asn Leu Asp Arg Ser Lys Asp Arg Val
                 20                  25                  30

Ser Thr Gly Leu Arg Ile Ser Asn Ala Ser Glu Asn Thr Ala Tyr Trp
                 35                  40                  45

Ser Ile Ser Ser Met Met Arg His Asp Ser Asn Thr Met Ser Ala Ile
 50                  55                  60

Val Asp Ala Ile Asn Leu Gly Lys Glu Gln Val Gly Ile Ala Asp Thr
 65                  70                  75                  80

Ala Ile Gly Leu Thr Lys Glu Ala Leu Asp Ile Gln Lys Ser Met
                 85                  90                  95

Val Ser Ala Arg Glu Lys Gly Ser Asp Asp Ile Ala Lys Ile Gln Asp
                100                 105                 110

Ser Ile Ile Gly Asn Met Lys Asn Ile Ser Asn Ala Val Gln Ser Ala
                115                 120                 125

Ser Phe Gly Gly Lys Asn Ile Leu Ser Asn Gly Gly Gln Thr Val Gly
                130                 135                 140
```

Met Ala Gly Tyr Arg Arg Glu Gly Thr Ala Val Tyr Val Asp Met
145                 150                 155                 160

Ile Asp Val Gly Gly Ser Glu Leu Asn Phe Gly Thr Ile Gly Ser Asp
                165                 170                 175

Gly Thr Ile Asp Met Ser Gln Gly Val Leu Gly Gly Ile Phe Gly Thr
            180                 185                 190

Ser Lys Gly Asp Glu Gly Glu Asp Val Val Gly Lys Gly Ile Gly Ala
        195                 200                 205

Phe Ser Ala Ala His Ala Thr Tyr Lys Gly Leu Glu Asp Thr Leu Arg
    210                 215                 220

Asn Ala Glu Ala Asp Leu Ala Lys Ala Ile Ala Lys Tyr Gly Glu Ser
225                 230                 235                 240

Pro Glu Asp Glu Pro Gly Lys Ala Ile Ile Glu Lys Ala Lys Gln Ala
                245                 250                 255

Val Glu Thr Ala Lys Thr Gly Leu Lys Asp Gly Gln Glu Ala Tyr Asn
            260                 265                 270

Lys Ala Lys Gly Glu Phe Gln Thr Val Leu Asp Gly Met Thr Leu Ala
        275                 280                 285

Asp Phe Thr Glu Leu Lys Gly Leu Gly Glu Leu His Ser Asp Ile Gln
    290                 295                 300

Arg Met Ile Met Thr Ser Val Gln Asn Thr Val Arg Asp Ala Val Asn
305                 310                 315                 320

Val Thr Leu Thr Ala Gly Ser Lys Ile Gly Ala Ala Val Asn Leu Val
                325                 330                 335

Asn Ile Gln Leu Asn Phe Val Lys Lys Leu Leu Asp Asn Val Glu Val
            340                 345                 350

Gly Ile Gly Ala Leu Val Asp Ala Asp Met Asn Ala Glu Ser Ala Lys
        355                 360                 365

Leu Ala Ala Leu Gln Val Gln Gln Leu Gly Ile Gln Ala Leu Ser
    370                 375                 380

Ile Ala Asn Gln Gly Ser Gln Asn Ile Leu Ala Leu Phe Arg Asn
385                 390                 395

<210> SEQ ID NO 34
<211> LENGTH: 181
<212> TYPE: PRT
<213> ORGANISM: Artificial Sequence
<220> FEATURE:
<223> OTHER INFORMATION: consensus sequence

<400> SEQUENCE: 34

Met Ile Asn Thr Asn Val Ala Leu Ala Gln Asn Leu Lys Gln Leu Ser
1               5                   10                  15

Leu Glu Arg Leu Ser Ser Gly Leu Arg Ile Asn Ser Ala Asp Asp Ala
            20                  25                  30

Ala Gly Met Ala Ile Ala Arg Leu Ser Gln Val Arg Gly Leu Gln Ala
        35                  40                  45

Thr Arg Asn Ala Asn Asp Gly Ile Ser Ile Leu Gln Thr Ala Glu Gly
    50                  55                  60

Ala Leu Glu Ile Leu Gln Arg Ile Arg Asp Leu Val Gln Ala Asn Gly
65                  70                  75                  80

Thr Gln Ser Asp Arg Ile Gln Glu Ile Gln Leu Met Glu Glu Ile Asp
            85                  90                  95

Arg Ile Ala Thr Phe Asn Gly Met Lys Leu Leu Gly Gln Ile Gly Val
        100                 105                 110

```
Ile Val Ile Gly Leu Leu Met Met Ile Asp Ala Met Leu Arg Ala Leu
            115                 120                 125

Gly Ala Val Gln Asn Arg Val Asp Ile Asn Leu Glu Asn Leu Ala Ala
    130                 135                 140

Ser Arg Ile Asp Ala Asp Ala Glu Val Thr Asn Leu Ser Lys Gln Ile
145                 150                 155                 160

Leu Gln Gln Gly Ser Ile Leu Ala Gln Ala Asn Gln Pro Gln Asn Val
                165                 170                 175

Leu Ser Leu Leu Arg
            180

<210> SEQ ID NO 35
<211> LENGTH: 39
<212> TYPE: DNA
<213> ORGANISM: Artificial Sequence
<220> FEATURE:
<223> OTHER INFORMATION: primer

<400> SEQUENCE: 35
ttaaagtggt accagttctc cctttcatt gtatgcact                              39

<210> SEQ ID NO 36
<211> LENGTH: 35
<212> TYPE: DNA
<213> ORGANISM: Artificial Sequence
<220> FEATURE:
<223> OTHER INFORMATION: primer

<400> SEQUENCE: 36
cgggatcccg ttaggagatg gttgctacag tttgc                                 35

<210> SEQ ID NO 37
<211> LENGTH: 18
<212> TYPE: PRT
<213> ORGANISM: Artificial Sequence
<220> FEATURE:
<223> OTHER INFORMATION: synthetic construct

<400> SEQUENCE: 37

Ala Asp Thr Arg Asp Leu Gly Ala Val Gln Asn Arg Phe Asn Ser Ala
 1               5                  10                  15

Ile Thr

<210> SEQ ID NO 38
<211> LENGTH: 18
<212> TYPE: PRT
<213> ORGANISM: Artificial Sequence
<220> FEATURE:
<223> OTHER INFORMATION: synthetic construct

<400> SEQUENCE: 38

Val Asp Ala Arg Asp Leu Gly Ala Val Gln Asn Arg Phe Asn Ser Ala
 1               5                  10                  15

Ile Thr

<210> SEQ ID NO 39
<211> LENGTH: 18
<212> TYPE: PRT
<213> ORGANISM: Artificial Sequence
<220> FEATURE:
<223> OTHER INFORMATION: synthetic construct

<400> SEQUENCE: 39
```

```
Val Asp Thr Ala Asp Leu Gly Ala Val Gln Asn Arg Phe Asn Ser Ala
1               5                   10                  15

Ile Thr

<210> SEQ ID NO 40
<211> LENGTH: 15
<212> TYPE: PRT
<213> ORGANISM: Artificial Sequence
<220> FEATURE:
<223> OTHER INFORMATION: synthetic construct

<400> SEQUENCE: 40

Arg Ser Asp Leu Gly Ala Val Gln Asn Arg Phe Asn Ser Ala Ile
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: synthetic construct

<400> SEQUENCE: 41

Asp Leu Gly Ala Val Gln Asn Arg Phe Asn Ser Ala Ile Thr Asn
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: synthetic construct

<400> SEQUENCE: 42

Gly Ala Val Gln Asn Arg Phe Asn Ser Ala Ile Thr Asn Leu Gly
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: synthetic construct

<400> SEQUENCE: 43

Val Gln Asn Arg Phe Asn Ser Ala Ile Thr Asn Leu Gly Asn Thr
1               5                   10                  15
```